(12) United States Patent
Cherkasov et al.

(10) Patent No.: US 8,637,650 B2
(45) Date of Patent: *Jan. 28, 2014

(54) MACROMOLECULAR NUCLEOTIDE COMPOUNDS AND METHODS FOR USING THE SAME

(75) Inventors: Dmitry Cherkasov, Luebeck (DE); Christian Hennig, Hannover (DE)

(73) Assignee: Genovoxx GmbH, Luebeck (DE)

(*) Notice: Subject to any disclaimer, the term of this patent is extended or adjusted under 35 U.S.C. 154(b) by 1669 days.

This patent is subject to a terminal disclaimer.

(21) Appl. No.: 10/578,313

(22) PCT Filed: Nov. 5, 2004

(86) PCT No.: PCT/EP2004/012556
§ 371 (c)(1),
(2), (4) Date: Jul. 18, 2007

(87) PCT Pub. No.: WO2005/044836
PCT Pub. Date: May 19, 2005

(65) Prior Publication Data
US 2010/0029494 A1    Feb. 4, 2010

(30) Foreign Application Priority Data

Nov. 5, 2003  (DE) .................. 103 51 636
Dec. 5, 2003  (DE) .................. 103 56 837

(51) Int. Cl.
| C07H 21/02 | (2006.01) |
| C07H 21/04 | (2006.01) |
| C07H 21/00 | (2006.01) |
| C07H 19/04 | (2006.01) |
| C12Q 1/68  | (2006.01) |
| C12P 19/34 | (2006.01) |

(52) U.S. Cl.
USPC ....... 536/23.1; 536/24.3; 536/25.3; 536/26.6; 435/6.1; 435/91.1; 422/61

(58) Field of Classification Search
USPC ......... 536/23.1, 25.3, 24.3, 26.6; 435/6, 91.1; 422/61

See application file for complete search history.

(56) References Cited

U.S. PATENT DOCUMENTS

| 5,256,535 A | 10/1993 | Ylikoski et al. |
| 2003/0054396 A1 | 3/2003 | Weiner |
| 2003/0207300 A1 | 11/2003 | Matray et al. |
| 2004/0248150 A1 | 12/2004 | Singh et al. |
| 2007/0208169 A1* | 9/2007 | Bodepudi et al. ............ 536/26.1 |

FOREIGN PATENT DOCUMENTS

| WO | WO 88/02784 | 4/1988 |
| WO | WO 03/020968 A3 | 3/2003 |
| WO | WO 03/048178 A2 | 6/2003 |
| WO | WO 2004/007773 A1 | 1/2004 |

(Continued)

OTHER PUBLICATIONS

United States Office Action issued in U.S. Appl. No. 11/886,518, mailed Dec. 8, 2010

(Continued)

*Primary Examiner* — Jezia Riley
(74) *Attorney, Agent, or Firm* — McDermott Will & Emery LLP

(57) ABSTRACT

The invention relates to novel classes of nucleotides that can be used as substrates for enzymes, e.g. for labeling nucleic acids.

47 Claims, 51 Drawing Sheets

(56) References Cited

FOREIGN PATENT DOCUMENTS

| WO | WO 2004/092331 A2 | 10/2004 |
|---|---|---|
| WO | WO 2005/044836 A2 | 5/2005 |
| WO | WO 2006/097320 A2 | 9/2006 |

OTHER PUBLICATIONS

Cherkasov, D., et al., "New Nucleotide Analogues with Enhanced Signal Properties", Bioconjugate Chem., 2010, pp. 122-129, vol. 21, American Chemical Society.

International Search Report issued in International Patent Application No. PCT/EP2007/008198, dated Apr. 17, 2009.

International Search Report, with its partial English translation, issued in International Patent Application No. PCT/EP2004/012556, dated May 19, 2005.

Lemaitre M et al., "Biological Activities of Oligonucleotides linked to Poly(L-Lysine)", Nucleosides, Nucleotides and Nucleic Acids, 1987, pp. 311-315, vol. 6, No. 1&2, Marcel Dekker, Inc, New York.

Jaeschke, A et al., "Hybridization-based affinity partitioning of nucleic acids using PEG-coupled oligonucleotides", Nucleic Acids Research, 1994, vol. 22, No. 10, pp. 1880-1884, Oxford University Press.

International Search Report issued in International Patent Application No. PCT/EP2006/002461 dated on Dec. 29, 2006.

* cited by examiner

Fig. 1
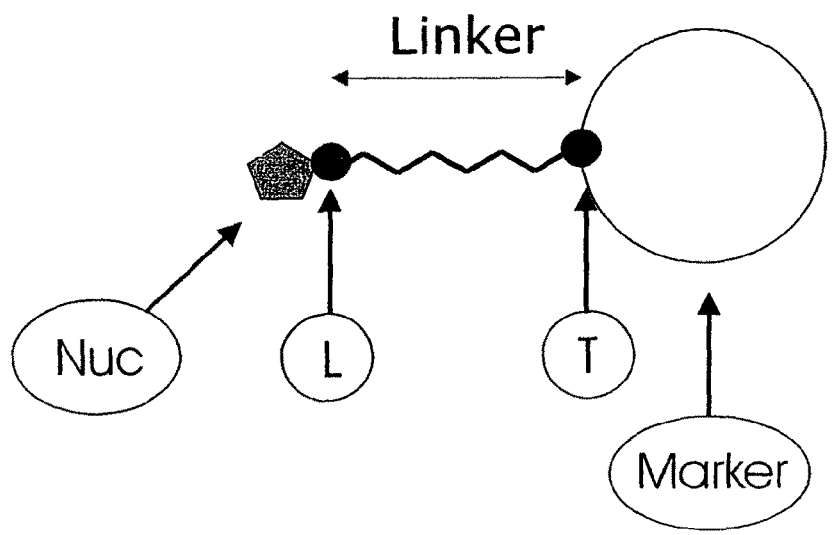
Legend:
   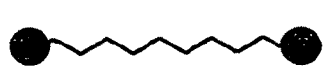   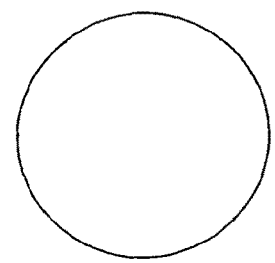
Nuc-component    Linker component    Marker component Fig. 2
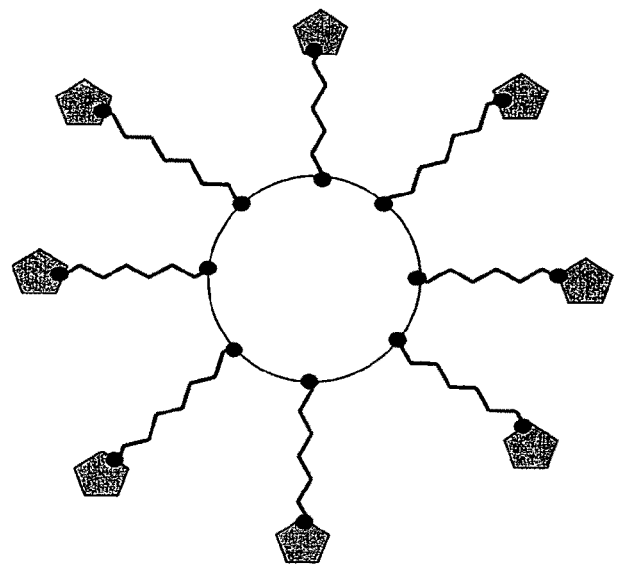
Legend:
  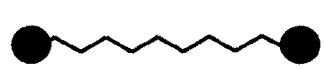  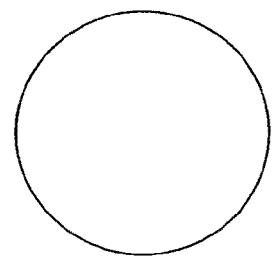
Nuc-component        Linker component        Marker component Fig. 3
A) 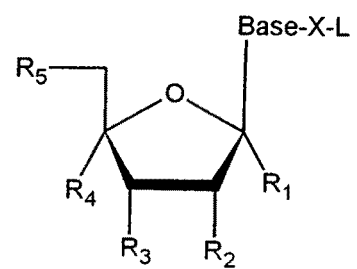
B) 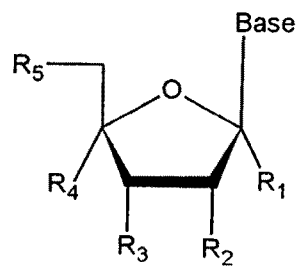

Fig. 5
A)
B)
C)
D)
Legend:
   
Nuc-component    Linker component    Core component    Marker unit with a linker Fig. 6
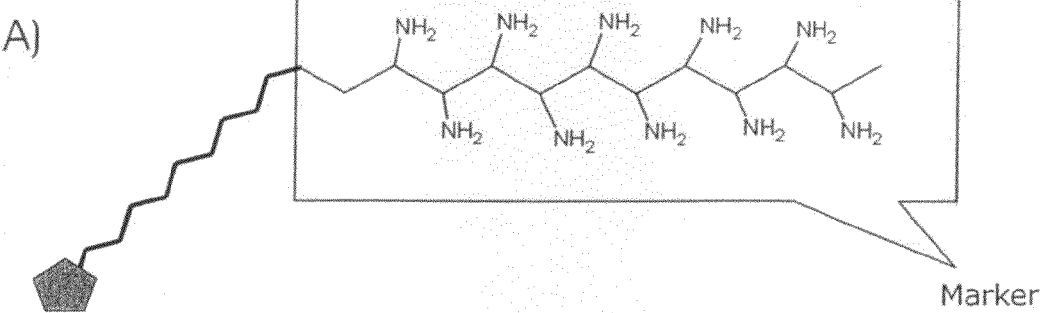
A)
Marker
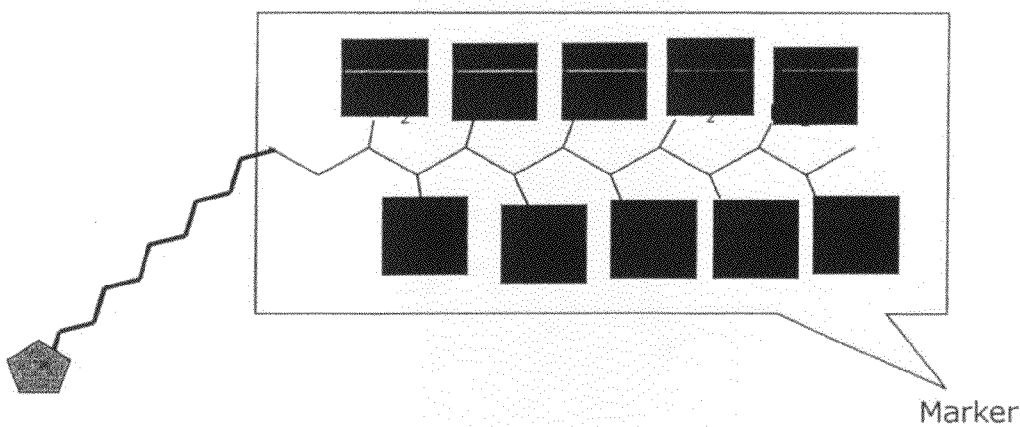
B)
Marker
Legend:
  
Nuc-component    Linker component    Signal giving marker unit Fig. 8
A) 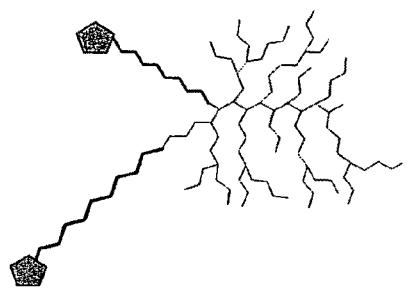
B) 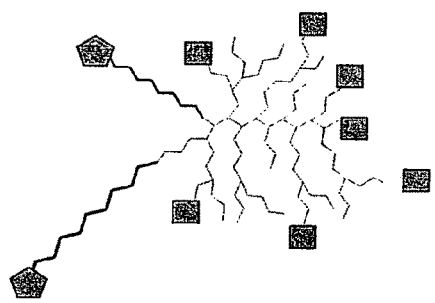
Legend:
      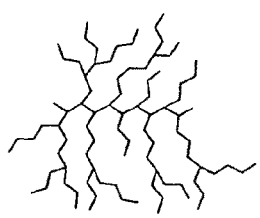
Nuc-component    Linker component    Signal giving marker unit    Branched polymer as a core component e.g. Dendrimer Fig. 10
A) 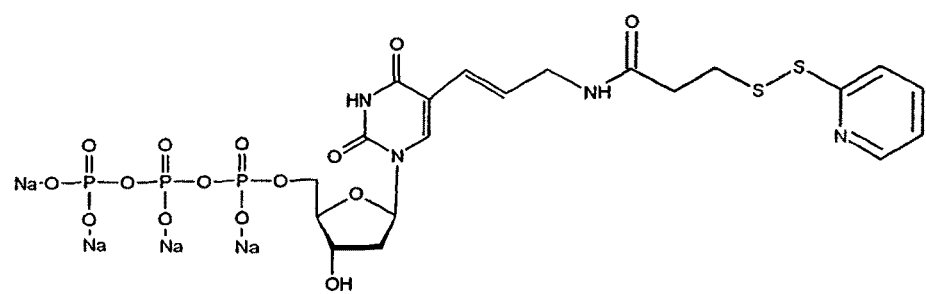
B) 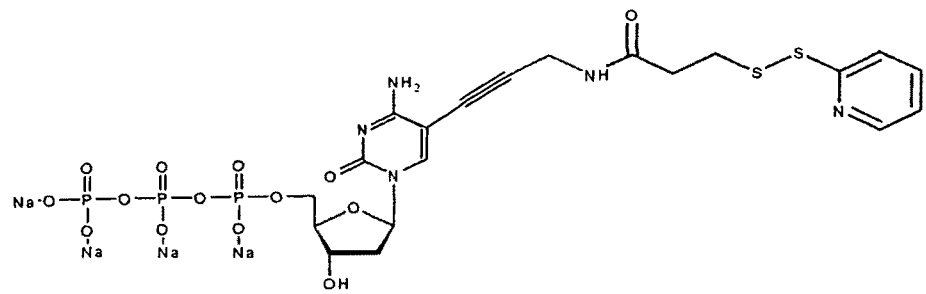

Fig. 11
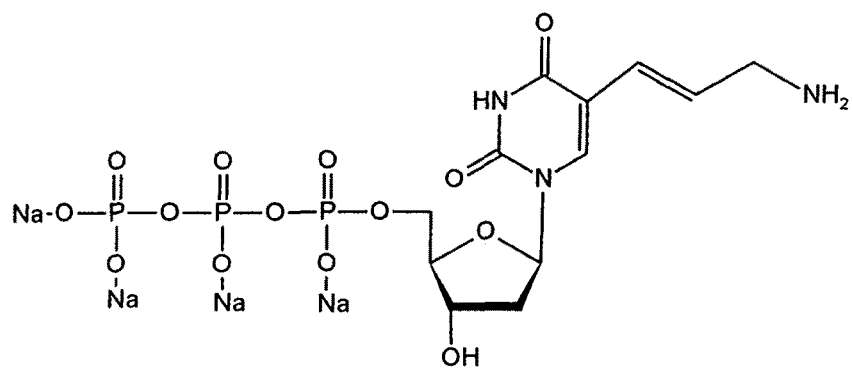
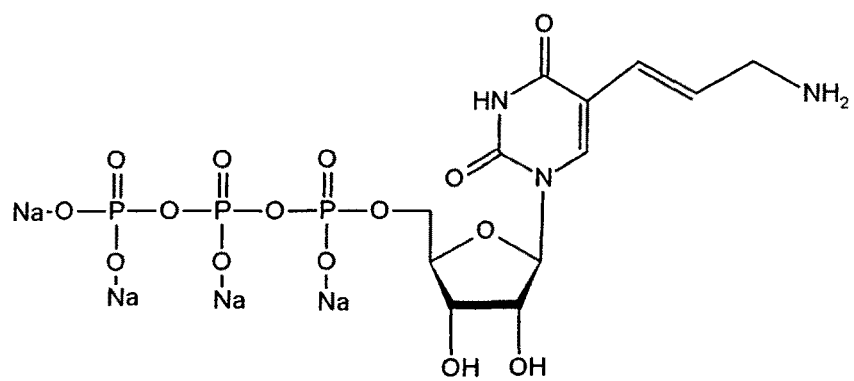
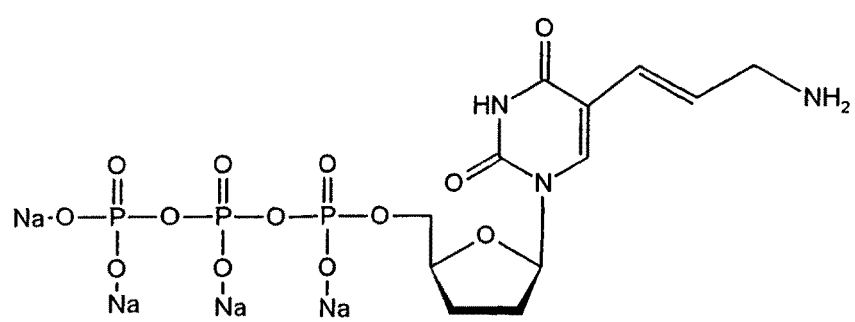

Fig. 12
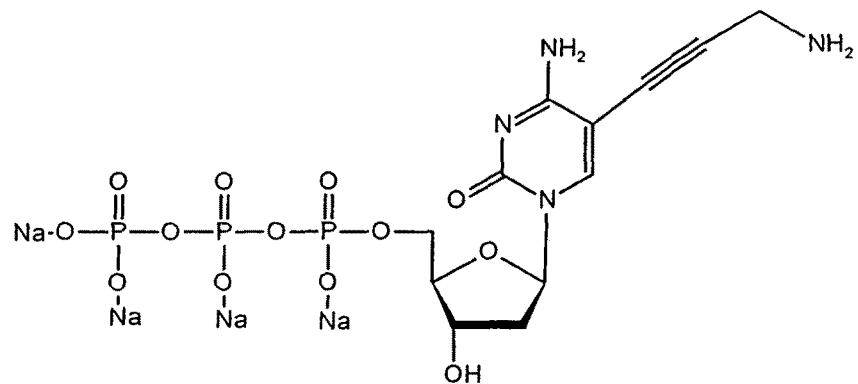
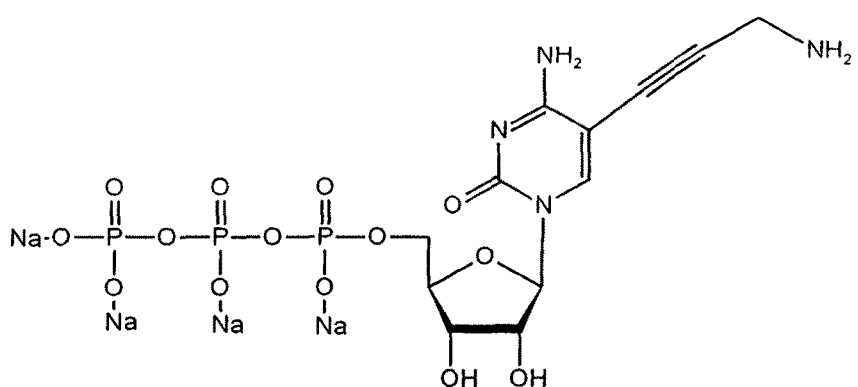
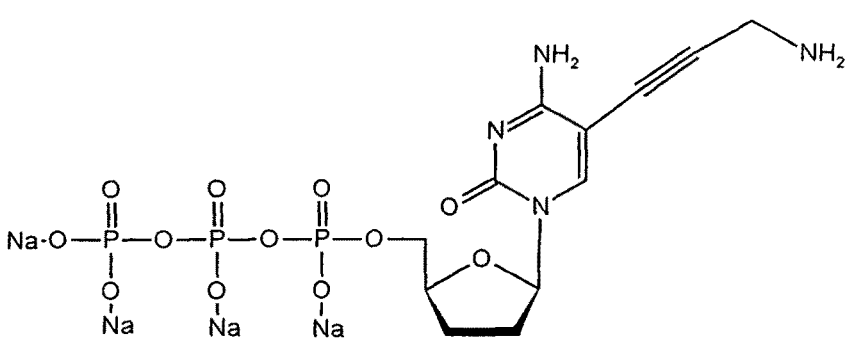

Fig. 24
A) 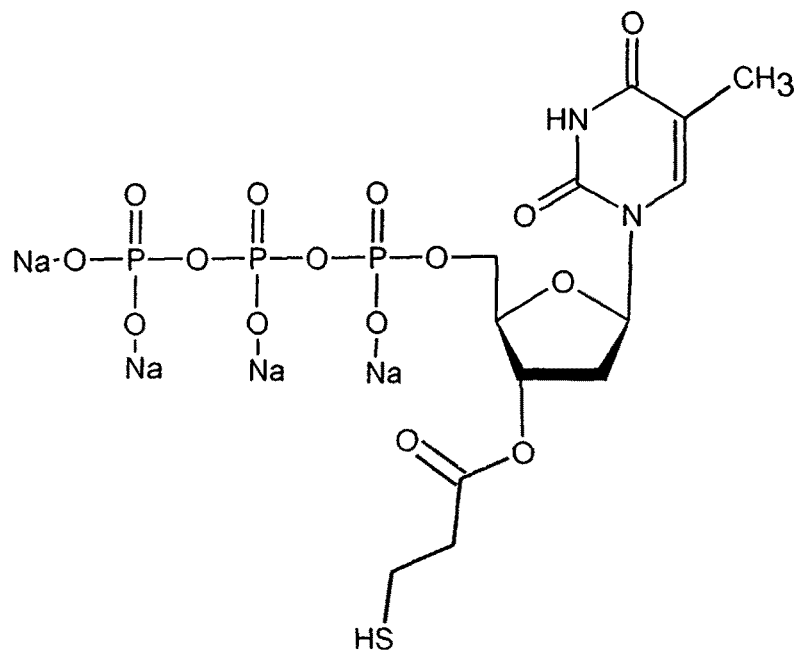
B) 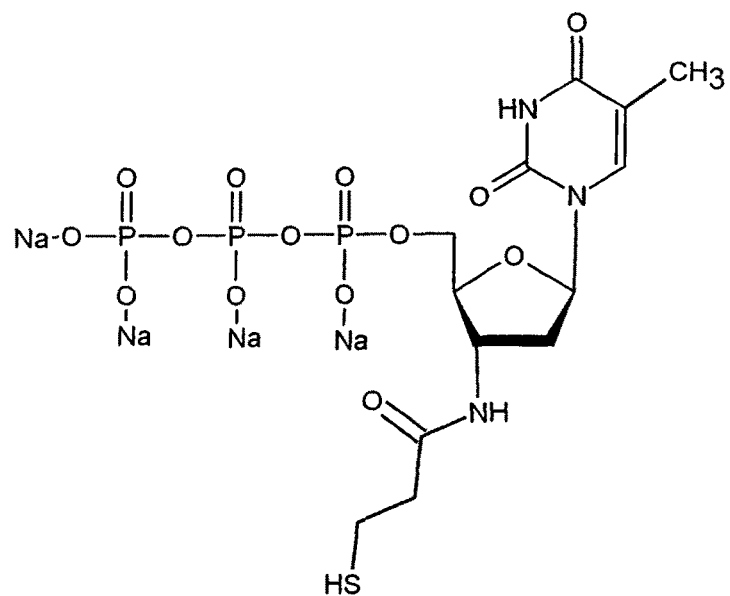

Coupling unit L

Legend:

A) Chemical structure of the nuc-linker-component

B) Schematic appointment of individual components

Fig. 32
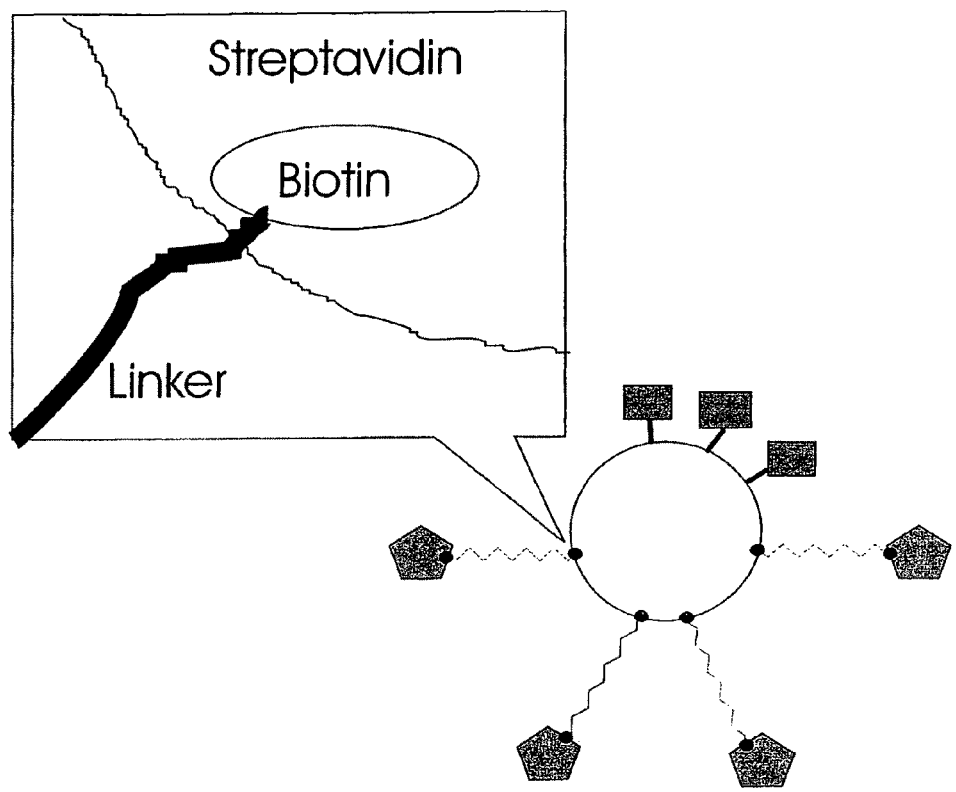
Legend:
dUTP as a nuc-component
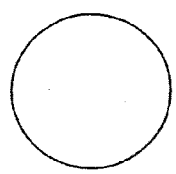
Strepavidin as a marker component
Fluorescent dye
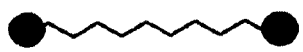
Linker component Fig. 33
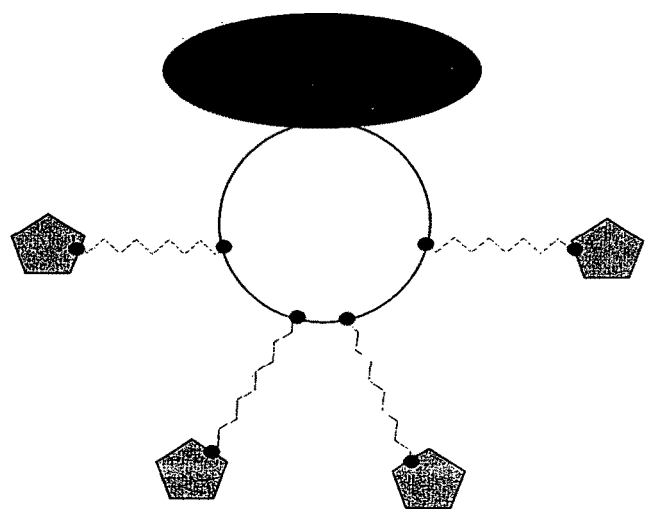
Legend:
dUTP as a nuc-component
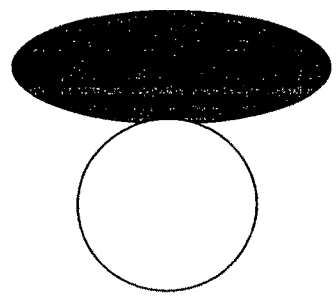
Strepavidin-enzyme conjugate as a marker component
Linker component Fig. 34
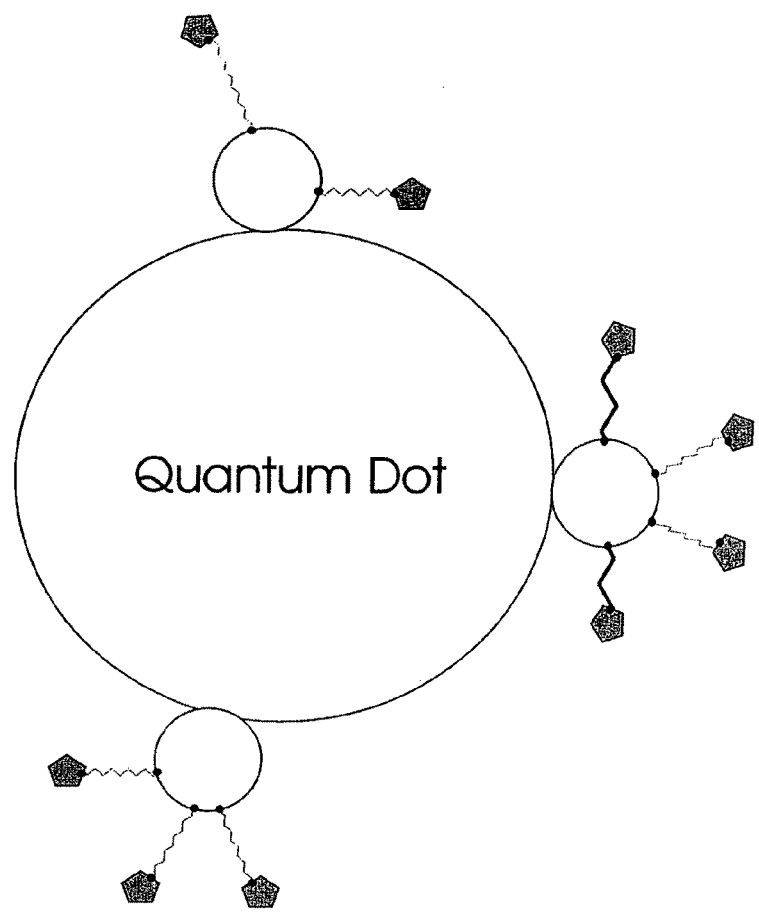
Legend:
  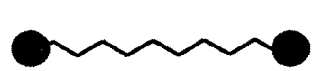  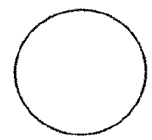
dUTP as a nuc-component     Linker component     Strepavidin attached to Quantum Dot Fig. 35
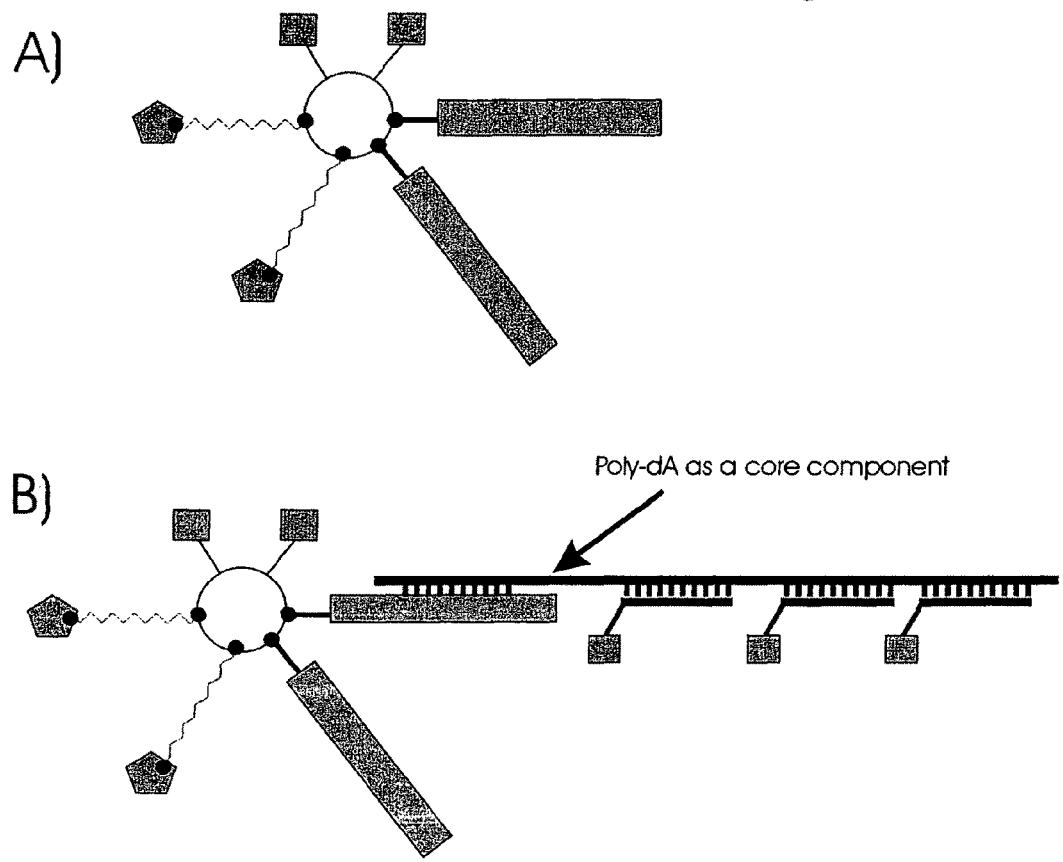
Legend:
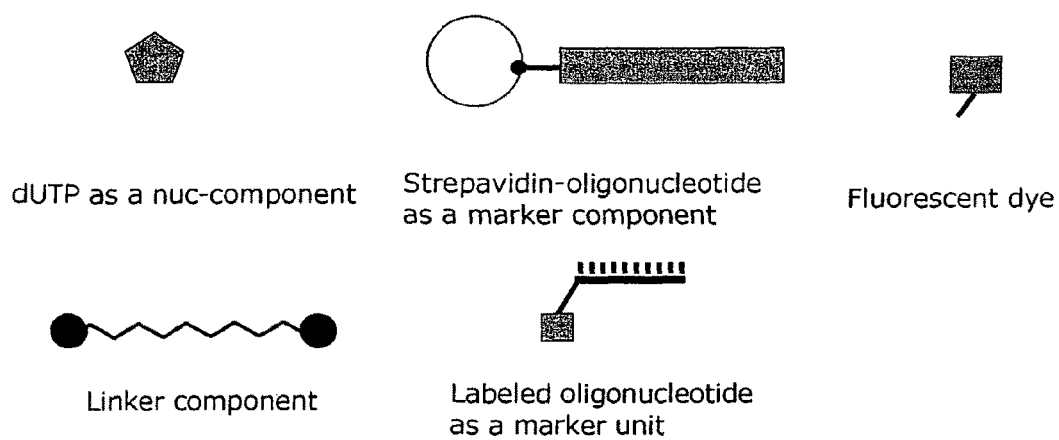
dUTP as a nuc-component
Strepavidin-oligonucleotide as a marker component
Fluorescent dye
Linker component
Labeled oligonucleotide as a marker unit Fig. 36
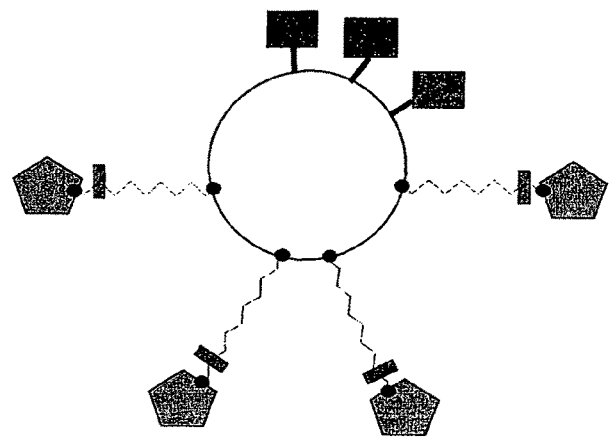
Legend:
dUTP as a nuc-component
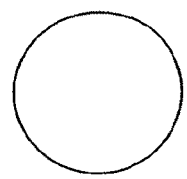
Strepavidin as a marker component
Fluorescent dye
Linker component with a cleavable compound

MACROMOLECULAR NUCLEOTIDE COMPOUNDS AND METHODS FOR USING THE SAME This application is the U.S. National Phase under 35 U.S.C. §371 of International Application No. PCT/EP2004/012556, filed Nov. 5, 2004, which in turn claims the benefit of German Application No. DE 103 51 636.0, filed Nov. 5, 2003 and German Application No. DE 103 56 837.9, filed Dec. 5, 2003, the disclosures of which Applications are incorporated by reference herein in their entirety.

DESCRIPTION OF THE INVENTION

Introduction

TECHNICAL FIELD

One aspect of the invention relates to the structure, the manufacturing and the application of modified nucleotide and nucleoside components, hereinafter called "nuc-macromolecules".

Another aspect of the invention relates to the structure, the manufacturing and the application of modified nucleic acids, e.g. oligonucleotides.

STATE OF THE ART

Substances with low molecular weight play an important role in living organisms. They act for example as building blocks of polymers, as messengers and as energy carriers. They are used in the field of diagnostics for analysis of parameters with medical relevance. In such procedures, these substances are often labeled with signal carriers. One example for said substances are nucleotides and nucleosides with low molecular weight.

They also play a central role in different metabolic processes in living organisms. ("Biochemie und Pathobiochemie", G. Löffler, 2003) and represent compounds often used in modern biotechnology ("Molecular-Cloning", J. Sambrook, Volume 1-3, 2001, ISBN 0-87969-576-5), for example in artificial detection systems ("DNA Microarrays", Bowtell, 2003, ISBN 0-87969-624-9, "Microarray-Biochip Technology" M Schena, 2000, ISBN 1-881299-37-6). For these reasons, modified nucleotides and nucleoside-analogs are used in various fields of biotechnology, medicine and pharmacology ("Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997).

One of the important fields of modern life-science is the analysis of nucleic acids. One large part of this field is dedicated to the detection of nucleic acids and their components in biological samples. In many cases, labeled reaction components, which can react with the nucleic acid to be analyzed, are used. Different labeling procedures for the labeling of nucleic acids are known to the person skilled in the art. On the one hand, individual building blocks of the nucleic acids, i.e. nucleotides or nucleosides, can be modified, on the other hand, short fragments of nucleic acids, oligonucleotides or polynucleotides, can be used for the detection.

Conventionally modified nucleotides are disclosed for example in Lee et al. Nucleic acid research 1992, v. 20, p. 2471; Augustin et. al. J. Biotechnology 2001 v. 86, p. 289-301; U.S. Pat. No. 4,828,979; Held et al. Nucleic acid research, 2002, v. 30, p. 3857. Such modified nucleotides may include a detectable part of low molecular weight that can be detected directly (e.g. fluorescent dye molecule) or indirectly (e.g. biotin molecule that can be detected only after coupling to a streptavidin-dye conjugate). Such nucleotides represent examples of the state-of-the-art modifications of the nucleotides. Many modified nucleotides can be purchased, e.g. from NEN Life Science Products (Biotin-11-dUTP, DNP-11-dATP, Fluorescein-12-dCTP), Amersham Bioscience (dCTP-Cy3, dCTP-Cy5) or Roche (Biotin-16-dUTP). Corresponding detection reagents, e.g. labeled streptavidin and labeled antibodies, can be purchased from the same suppliers. Also modified nucleosides can be used for detection of the nucleic acids (Trilink Biotechnologies, Eurogentec, MWG-Biotech).

For the clearness and simplification of the description, focus will be placed on modified nucleotides. To a person skilled in the art, it should be obvious that modified nucleosides can also be used in enzymatic and non-enzymatic synthesis reactions (conventional modified nucleosides can be purchased from Trilink Biotechnologies or Eurogentec). Conventionally modified nucleotides have an aquimolar ratio between the nucleotide component and the low-molecular-weight detectable part, e.g. fluorescent dye or biotin molecule. A linker with an averaged length of 5 to 30 atoms connects both parts.

Such nucleotides can be incorporated in to the growing strand of nucleic acids by polymerases, introducing a signal-carrying molecule (e.g. dye) or signal-transmitting molecule (e.g. biotin or digoxigenin) into the nucleic acid chain. Signal detection can take place directly after incorporation of dye modified nucleotides or after incubation with a secondary signal-carrying molecule (e.g. streptavidin dye conjugate in the case of biotin). Frequently, the yield of the subsequent coupling of signal-carrying molecules, like streptavidin, is insufficient (20-60%).

Signal multiplication steps are often used in the labeling procedures of nucleic acids. These steps can be applied in different stages of the analysis. Material amplification (e.g. PCR), multiple incorporation of labeled nucleotides or multistep subsequent labeling of biotin nucleotides are examples for signal multiplication ("Molecular-Cloning", J. Sambrook, Volumes 1-3, 2001, ISBN 0-87969-576-5). Such procedures may lead to distortion of the signals, because such procedures imply multiple, often insufficiently controlled steps with different yields, and may be influenced by many factors.

The desirable signal multiplication, which is obvious to the person skilled in the art, obtained by multiple labeling of nucleotides already during the chemical synthesis of the nucleotides turns out to be a very large drawback in combination with conventional nucleotide structure. While such labeled nucleotides can be synthesized without great difficulty (Example 25), they lose their function as substrates for polymerases (Example 34B) and other enzymes. The reason for this is the change in the properties of the nucleotides as a result of the coupling to a large molecule.

Certain procedures, described for example in Seeger WO 0018956 and Kartalov WO 02072892, rely on the detection of signals from single nucleotide molecules. When conventional nucleotides are used, several phenomena, e.g. bleaching or blinking, affect the results of the single molecule detection. An increase in signal strength and intensity could be important in lowering the error rate for such methods. There is a demand for modified nucleotides or nucleosides with a better signal-giving or signal-transmitting features, especially in the field of labeling nucleic acids for the analysis.

Purpose of the Invention

One object of the invention is therefore to provide modified nucleotides or nucleosides that retain their substrate properties towards polymerases or other enzymes and have improved signal intensity after being incorporation into the nucleic acids.

Another object of the invention is to provide methods for the labeling of nucleic acids with nucleotides modified according to the invention.

The present invention discloses, in one embodiment, a new class of modified nucleotides, called "nuc-macromolecules". Nuc-macromolecules are characterized in that the one or several nucleotide-components are attached to one or several signal-giving or signal-transmitting macromolecular components (markers) via a long linker. Individual nuc-components retain their substrate properties in a nuc-macromolecule and can be incorporated into a growing strand of the nucleic acid by polymerases, for example. A signal-giving macromolecular component carries several dye molecules, for example.

Nuc-macromolecules can be used like conventional modified nucleotides in different areas of biotechnology or medicine. For the purpose of demonstration, methods for labeling nucleic acids are provided. Other applications of modified nucleotides are already known to the person skilled in the art, as described above.

Terms and Definitions

Macromolecular Compound—a molecule or complex of molecules or a nanocrystal or nanoparticle, which has a molecular weight between 2 kDa and 20 kDa, 2 kDa and 50 kDa, 2 kDa and 100 kDa, 100 kDa and 200 kDa, 200 kDa and 1000 kDa or 1 MDa and 100 MDa or 100 MDa and 100 Gda. Examples of macromolecular compounds are nucleic acids, e.g. oligonucleotides with a length of more than 10 nucleotides, polynucleotides, polypeptides, proteins or enzymes, quantum dots, polymers like PEG, Mowiol, polyacrylate, nanogold particles and complexes comprising several macromolecules.

Low-Molecular Compound—a molecule or a molecule, complex, which has a mass smaller than 2000 Da (2 kDa), e.g. biotin, natural nucleotides, dATP, dUTP, many dyes, like Cy3, rhodamine, fluorescein, linkers with an average length between 5 and 30 atoms, rare earth elements and conventionally modified nucleotides, like biotin-16-dUTP.

A Nuc-Macromolecule—within the meaning of this application is a chemical structure, which comprises one or more nuc-components, one or more linker components, and a marker component, FIG. 1 or 2:

(Nuc-Linker)$_n$-Marker where:
Nuc—is a nuc-component
Linker—is a linker component
Marker—is a marker component
n—is a positive integer from 1 to 100

In a preferred embodiment, the linker component comprises a coupling unit (L) for coupling the linker to the nuc-component, a water soluble polymer and a coupling unit (T) for coupling the linker to the marker component. In this preferred embodiment, a nuc-macromolecule has the following structure, FIG. 1 or 2:

(Nuc-L-Polymer-T)$_n$-Marker where:
Nuc—is a nucleotide monomer or a nucleoside monomer (nuc-component)
L—is a part of the linker that represents a linkage between nuc and the rest of the linker (coupling unit L)
T—is a part of the linker that represents a linkage between the rest of the linker and the marker (coupling unit T)

Polymer—is a part of the linker that is a water-soluble polymer with an average length between 100 and 10,000 atoms. (In this embodiment, the coupling unit (L), the polymer and the coupling unit (T) are combined as the linker component)
Marker—is a marker component
n—is a positive integer from 1 to 100

Nuc-macromolecules are defined by a combination of one or more nuc-component, respectively, one or more long linker component and one marker component.

Nuc-component

A nuc-component can represent a nucleotide as well as a nucleoside. In the following, nucleotides will be described. For a person skilled in the art it may occur obvious that nucleosides can also be modified in a corresponding manner and used in corresponding reactions.

In one embodiment, the nuc-component is a nucleotide monomer or a nucleoside monomer, which is coupled to the linker component. In principle, all conventional nucleotide variants that are suitable as a substrate for nucleotide-accepting enzymes can serve as nuc-component of the nuc-macromolecule so that naturally occurring nucleotides as well as modified nucleotides (nucleotide analogs) can be considered for the nuc-component. Modified nucleotides comprise base-, sugar- or phosphate-modified nucleotide analogs, FIG. 3. Many examples are known to the person skilled in the art ("Advanced organic chemistry of nucleic acids", 1994, Shabarova, ISBN 3-527-29021-4, "Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997); further examples for modifications of the nucleotides will also be cited in the text.

The nuc-component preferably comprises a base part (base), a sugar part (sugar) and optionally a phosphate part (phosphate). Base, sugar and phosphate can be modified, i.e. the basic structure resembles the natural occurring nucleotides, but comprises e.g. additional chemical groups. Examples for combinations of different nucleotide components are known to the person skilled in the art. Such nuc-components can be used in a variety of enzymatic and chemical reactions (G. Wright et al. Pharmac. Ther. 1990, v. 47, p. 447-).

In another embodiment, the nuc-component is coupled with other nucleotides, e.g. in a nucleic acid chain. In this embodiment, the nuc-component acts as a monomer of a polymer.

Variations of the Phosphate

In one embodiment the nuc-component is a nucleoside. In another embodiment the nuc-component represents a nucleoside-monophosphate. In another embodiment the nuc-component represents a nucleoside-diphosphate. In another embodiment the nuc-component is a nucleoside-triphosphate. Still higher numbers of phosphate groups in a nucleotide (e.g. tetraphosphate etc.) can be used.

The said phosphate modifications can be located at the 5'-position of the sugar, like nucleoside-triphosphates, or also at other positions of the sugar part of the nucleotide, e.g. at the 3'-position.

Optionally, the phosphate part of the nucleotide can comprise modifications, in one embodiment such modifications comprising a linker, for example (D. Jameson et al. Methods in Enzymology 1997, v. 278, p. 363-, A. Draganescu et al. J.

Biol. Chem. 2000 v. 275, p. 4555-). In another embodiment of the invention, the phosphate part of the nuc-component comprises thiotriphosphate derivates (Burges et al. PNAS 1978 v. 75, p. 4798-).

In another embodiment of the invention, the phosphate part of the nuc-component comprises protected phosphate groups (e.g. phosphoroamidites).

In one embodiment, the phosphate part represents a linkage between the nuc-component and the linker component of the nuc-macromolecule.

Variations of the Base

The nuc-component can be natural nucleotide or nucleoside occurring in the nucleic acids in nature or their analogs, preferably participating at the Watson-Crick base-pairing, e.g. adenine, guanine, thymine, cytosine, uracil, inosine or modified bases like 7-deazaadenine, 7-deazaguanine, 6-thioadenine (as referred above). Optionally, the base comprises modifications. In one embodiment, such modifications comprise for example a linker, e.g. amino-propargyl-linker or amino-allyl-linker. Further examples of linkers are known (G. Wright et al. Pharmac. Ther. 1990, v. 47, p. 447-, Hobbs et al. U.S. Pat. No. 5,047,519 or other linkers e.g. Klevan U.S. Pat. No. 4,828,979, Seela U.S. Pat. Nos. 6,211,158, 4,804,748, EP 0286028, Hanna M. Method in Enzymology 1996 v. 274, p. 403, Zhu et al. NAR 1994 v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Odedra WO 0192284). In one embodiment, a linker coupled to the base represents a connection part between the nuc-component and the linker component of the nuc-macromolecule. Further modifications of the base are described for example in the catalogue of Trilink Biotechnologies, Inc. San Diego, USA, Issue 2003, page 38.

Variations of the Sugar

Different variations of the sugar part of the nucleotides, which are used e.g. in the diagnostics, therapy or research, are known to the person skilled in the art. Such variations comprise ribose, 2'-deoxyribose or 2',3'-dideoxyribose. Optionally, the sugar part comprises modifications (M. Metzker et al. Nucleic Acid Research 1994, v. 22, p. 4259-). In one embodiment, such modifications comprise for example a linker. The modifying group can be optionally be reversibly coupled to the sugar part (Hovinen et al. J. Chem. Soc. Prking Trans. 1994, s. 211-, Canard U.S. Pat. No. 5,798,210, Kwiatkowski U.S. Pat. No. 6,255,475, Kwiatkowski WO 01/25247, Ju et al. U.S. Pat. No. 6,664,079, Fahnestock et al. WO 91066678, Cheeseman U.S. Pat. No. 5,302,509, Parce et al. WO 0050642, Milton et al. WO 2004018493, Milton et al. 2004018497). In one embodiment, the linker coupled to the sugar part represents the connection between the nuc-component and the linker component of the nuc-macromolecules.

In another embodiment, the sugar part comprises for example the following modifications: optionally the 3'-OH-Group or the 2'-OH-Group can be substituted by the following atoms or groups: halogen atoms, hydrogen atoms, amino- or mercapto- or azido groups (Beabealashvilli et al. Biochem Biophys Acta 1986, v. 868, p. 136-, Yuzhanov et al. FEBS Lett. 1992 v. 306, p. 185-).

In another embodiment, the nuc-component comprises acyclic nucleotide or nucleoside modifications (A. Holy Current Pharmaceutical Design 2003 v. 9, p. 2567-, G. Wright et al. Pharmac. Ther. 1990, v. 47, p. 447-). In another embodiment, the sugar part comprises a double bond.

In this application, the following abbreviations will be used for 2'-deoxynucleotides: dUTP for 2'-deoxyuridine-triphosphate, dCTP for 2'-deoxycytidine-triphosphate, dATP for 2'-deoxyadenosine-triphosphate, dGTP for 2'-deoxyguanosine-triphosphate.

Linking of the Nucleotide and Linker

The nuc-component is linked to the linker at a coupling position. This coupling position of the linker on the nuc-component can be located on the base, on the sugar (e.g. ribose or deoxyribose) or on the phosphate part.

The linkage between the linker component and the nuc-component is preferably covalent.

If the coupling position is on the base, then the following positions are preferable: position 4 or 5 for pyrimidine bases and positions 6, 7, 8 for purine bases. On sugar, positions 2', 3', 4' or 5' can serve as coupling positions. The coupling to the phosphate groups can proceed via alpha, beta, or gamma phosphate groups. Examples for coupling positions on the base are described in Short WO 9949082, Balasubramanian WO 03048387, Tcherkassov WO 02088382 (also see commercially available nucleotides e.g. from Amersham or Roche), on the ribose in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, on phosphate groups in Jameson et al. Method in Enzymology, 1997, v. 278, p. 363.

The location of the coupling position depends on the area of application of the nuc-macromolecules. For example, coupling positions on the sugar or on the base are preferable in cases where the marker is intended to stay coupled to the nucleic acid strand. The coupling to the gamma or beta phosphate groups can be used for example in cases where the marker has to be separated during the incorporation of the nuc-macromolecule.

The linking between the nuc-component and the linker component results via a coupling unit (L) that is a part of the linker component.

In one embodiment, the linkage between the nuc-component and the linker is stable, e.g. resistant to temperatures up to 130° C., pH-ranges from 1 to 14 and/or resistant to hydrolytical enzymes (e.g. proteases or esterases). In another embodiment of the invention, this linkage between the nuc-component and the linker component is cleavable under mild conditions.

This cleavable linkage allows removal of the linker components and the marker components. This can be advantageous for example for methods of sequencing by synthesis, like pyrosequencing, BASS (base addition sequencing schema) (Canard et al. U.S. Pat. No. 5,798,210, Rasolonjatovo Nucleosides & Nucleotides 1999, v. 18, p. 1021, Metzker et al. NAR 1994, v. 22, p. 4259, Welch et al. Nucleosides & Nucleotides 1999, v. 18, p. 19, Milton et al. WO 2004018493, Odedra at al. WO 0192284) or single molecule sequencing Tcherkassov WO 02088382. The choice of the cleavable linkage is not restricted insofar as it remains stable under conditions of enzymatic reaction, does not result in irreversible damage of the enzyme (e.g. polymerase) and is cleavable under mild conditions. "Mild conditions" is understood to mean conditions that do not result in damage of nucleic acid-primer complexes wherein, for example, the pH-range is preferably between 3 and 11 and the temperature is between 0° C. and the temperature value (x). This temperature value (x) is dependent upon the Tm of the nucleic acid-primer complex (where Tm is the melting temperature) and is calculated for example as Tm (nucleic acid primer complex) minus 5° C. (e.g. Tm is 47° C., then the (x)-value is 42° C.; ester, thioester, acetales, phosphoester, disulfide linkages and photolabile compounds are suitable as cleavable linkages under these conditions).

Preferably, the said cleavable linkage comprises chemical or enzymatic cleavable linkages or photolabile compounds. Ester, thioester, disulfide and acetal linkages are preferred as examples of chemical cleavable groups (Short WO 9949082, "Chemistry of protein conjugation and crosslinking" Shan S. Wong 1993 CRC Press Inc., Herman et al. Method in Enzymology 1990 v. 184 p. 584, Lomant et al. J. Mol. Biol. 1976 v. 104 243, "Chemistry of carboxylic acid and esters" S. Patai 1969 Interscience Publ.). Examples for photolabile compounds are described in Rothschild WO 9531429, "Protective groups in organic synthesis" 1991 John Wiley & Sons, Inc., V. Pillai Synthesis 1980 p. 1, V. Pillai Org. Photochem. 1987 v. 9 p. 225, Dissertation "Neue photolabile Schutzgruppen für die lichtgesteuerte Oligonucleotidsynthese" H. Giegrich, 1996, Konstanz, Dissertation "Neue photolabile Schutzgruppen für die lichtgesteuerte Oligonucleotidsynthese" S. M. Bühler, 1999, Konstanz).

Number of the Linked Nuc-components

In one embodiment of the invention, only one nuc-component is coupled per nuc-macromolecule. In another embodiment of the invention, several nuc-components are coupled per nuc-macromolecule. If several nuc-components are coupled, they can be identical or different, whereas the average number of the nuc-components per nuc-macromolecule can range for example from 2 to 5, 5 to 10, 10 to 25, 25 to 50, 50 to 100, 100 to 250, 250 to 500, 500 to 1000.

Linker Component

The terms "linker" and "linker component" will be used synonymously in this application and comprise the whole structural part of the nuc-macromolecule between the nuc-component and the marker component.

Parts of the Linker

The linker is a part of the nuc-macromolecule between the corresponding nuc-component and marker component. The linker preferably comprises the following parts in its structure:
1) coupling unit (L)
2) water soluble polymer
3) coupling unit (T)

The subdivision of the linker in separate parts is purely functional and should serve merely for better understanding of the structure. Depending on the approach, particular structures can be considered as one functional part or as another.

The coupling unit (L) has the function of linking the linker component and the nuc-component. Short, non-branched compounds no more than 20 atoms in length are preferred. The particular structure of the coupling unit (L) depends on the coupling position of the linker to the nucleotide and on the particular polymer of the linker. Several examples of coupling units (L) are shown in examples 1 to 33 of this application. Many conventionally modified nucleotides comprise a short linker; these short linkers are further examples of coupling units (L), e.g. short linker on the base: Short WO 9949082, Balasubramanian WO 03048387, Tcherkassov WO 02088382 (see also commercially available nucleotides from e.g. Amersham or Roche), short linker on the ribose as described in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Ju et al. U.S. Pat. No. 6,664,079, Parce WO 0050642, and short linker on phosphate groups as described in Jameson et al. Method in Enzymology, 1997, v. 278, p. 363.

Still further examples for the coupling unit (L) are presented in the following:

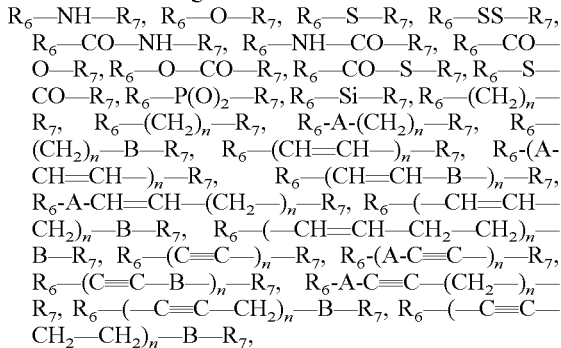

where $R_6$ is the nuc-component; $R_7$ is a polymer; A and B comprises the following structural elements: —NH—, —O—, —S—, —SS—, —CO—NH—, —NH—CO—, —CO—O—, —O—CO—, —CO—S—, —S—CO—, —P(O)_2—, —Si—, —(CH_2)_n—, a photolabile group; (n) is a number from 1 to 5

The coupling unit L is linked to the nuc-component on the one side and to the polymer on the other. The character of the linkage with the polymer depends on the kind of polymer.

In a preferred embodiment, the ends of the polymer comprises reactive groups, for example NH2 (amino), OH (hydroxy), SH (mercapto), COOH (carboxy), CHO (aldehyde), acrylic, maleimide or halogen groups. Such polymers are commercially available (e.g. Fluka). Some examples for the coupling of polymers to the coupling unit are shown in the examples 1 to 33.

In a preferred embodiment, the water-soluble polymer represents the major part of the linker component. It is a polymer, preferably hydrophilic, consisting of the same or different monomers.

Examples of suitable polymers are polyethylene-glycol (PEG), polyamides (e.g. polypeptides), polyphosphates, polyacetates, poly(alkyleneglycols), copolymers with ethylenglycol und propyleneglycol, poly(olefinic alcohols), poly (vinylpyrrolidones), poly(hydroxyalkylmethacrylamides), poly(hydroxyalkylmethacrylates), poly(x-hydroxy acids), polyacrylic acid and their derivates, poly-acrylamide and its derivates, poly(vinylalcohol), polylactic acid, polyglycolic acid, poly(epsilon-caprolactones), poly(beta-hydroxybutyrates), poly(beta-hydroxyvalerate), polydioxanones, poly (ethylene terephthalates), poly(malic acid), poly(tartronic acid), poly(ortho esters), polyanhydrides, polycyanoacrylates, poly(phosphoesters), polyphosphazenes, hyaluronidate, and, polysulfones.

In one embodiment, the polymer-part comprises branched polymers. In an other embodiment, the polymer-part comprises non-branched or linear polymers. The polymer can consist of several parts of different length, each part consisting of the same monomers with the monomers in different parts being different. To a person skilled in the art, it should seem obvious that for a macromolecular linker, it is often possible to determine only an average mass, so that the data regarding the mole masses represent an average ("Makromoleküle, Chemische Struktur und Synthesen", Volume 1, 4, H. Elias, 1999, ISBN 3-527-29872-X). For this reason, there is no exact mass information for nuc-macromolecules.

In one preferred embodiment, the linker component comprises a linear, non-branched polymer that is not modified with further sterically demanding chemical structures such as dyes, fluorescent dyes, or ligands. Such linker components lead to a low sterical hindrance, e.g. in an enzymatic recognition of the nuc-components.

In another preferred embodiment, the polymer of the linker component is linear but the linker component is modified with one or several sterically demanding chemical groups, for example dyes. The presence of the sterically demanding group allows for a control of the enzymatic reaction in some analytic processes (Tcherkassov WO 02088382).

Linker Length

The linker length amounts to between 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 atoms (chain atoms), so that an average linker length amounts to between 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 angstroms (measured on a molecule potentially stretched-out as much as possible).

If a nuc-macromolecule comprises several linker components, these linker components can be of the same or different lengths relative to each other.

Some parts of the linkers can comprise rigid areas and other parts can comprise flexible areas.

It will seem obvious to a person skilled in the art, that the said linkers can have a substantially bigger molecule size and molecule mass than the respective nuc-component itself. The data regarding the linker lengths relate to an average number of chain atoms.

Linker Coupling in a Nuc-macromolecule

The linker is connected to the nuc-component on one side and to the marker component on the other side. The linker has coupling units at his ends which fulfill this connecting function. The connection to the nuc-component was discussed above. The connection between the linker and the marker components is provided by coupling unit T. Short, non-branched connections no more than 20 atoms in the length are preferred. The respective structure of the coupling unit T depends upon the coupling position on the marker component and upon the respective polymer of the linker.

The coupling unit T is covalently connected to the polymer. The kind of the coupling depends on the kind of the polymer. In a preferred embodiment, the polymer has reactive groups, such as NH2 (amino), OH (hydroxy), SH (mercapto), COOH (carboxy), CHO (aldehyde), acrylic, maleimide or halogen groups, at its ends. Such polymers are commercially available (e.g. Fluka). Some examples of the coupling units L are shown in examples 1 to 33. For further examples of the chemical and affine connections please refer to the literature: "Chemistry of protein conjugation and crosslinking" Shan S. Wong in 1993, "Bioconjugation: protein coupling techniques for the biomedical sciences", M. Aslam, in 1996.

The linker can also comprise other functional groups or parts, for example one or several groups that are cleavable under mild conditions (FIG. 9), see examples 22, 23, 24, 31.

A cleavable group within the linker allows the removal of a part of the linker and the marker component. After a cleavage reaction, a linker residue remains coupled to the nuc-component. Examples of cleavable groups are shown in Section 1.3.3.1.4.

Marker Component

The marker component can comprise different structures. The structures individually are not limited, as long as they do not destroy the substrate properties of the nuc-components for enzymes. In preferred embodiments, such structures have a signal-giving or a signal-transmitting function. The marker can also comprise other functions, for instance, structural, anti-toxic or affine function (for instance, as part of medicines or medical preparations).

The Composition of the Marker Component (Marker)

In one embodiment, the marker comprises a low-molecular marker unit. In an other embodiment, the marker comprises a macromolecular marker unit. In a still further embodiment, the marker comprises several low-molecular marker units. In a still further embodiment, the marker comprises several macromolecular marker units. In a still further embodiment, the marker comprises a combination of low-molecular and macromolecular units. The marker units can have a signal-giving or signal-transmitting function.

These units can be molecules with low molecular mass, e.g. less than 2000 Da, or they can be also macromolecules. The number of the signal-giving or signal-transmitting units, which are combined into one marker component, comprises the following ranges: 1 and 2, 2 to 5, 5 to 20, 20 to 50, 50 to 100, 100 to 500, 500 to 1000, 1000 to 10000, 10000 to 100000.

If several marker units are combined into one marker component, then in one embodiment these units are bound to a framework, the core component of the marker (FIG. 4b, c). This core component connects the units together. The core component can provide the connection to one or several nuc-linker components (FIG. 5). The core component comprises low-molecular or macromolecular compounds.

Structure of the Signal-giving or the Signal-transmitting Units of the Marker The structural marker units comprise the following groups:

Structures with Low Molar Mass

Biotin molecules, hapten molecules (e.g. digoxigenin), radioactive isotopes (e.g., $P^{32}$, $J^{131}$), or their derivatives, rare earth elements, dyes, fluorescent dyes (many dyes are commercially available, e.g., from Molecular Probes, Inc) with the same or different spectral properties, groups of dyes undergoing FRET.

Also chemically reactive groups, as for example amino-, carboxy-, merkapto-, aldehyde, iodine acetate, acrylic, dithio-, thioester-groups, can serve as signal-transmitting structural units (FIG. 6a). These reactive groups can be modified with signal-giving elements, such as dyes with suitable reactive groups (for instance, NHS esters, mercapto-, amino groups) (FIG. 6b), e.g. after incorporation of nuc-macromolecules. General rules for the choice of a suitable pair of reactive groups are shown in "Chemistry of protein conjugation and crosslinking" Shan S. Wong 1993.

In a special embodiment, a combination comprising one nuc-component, one macromolecular linker component and one marker component with a low molecular weight already fulfils the requirements of the present invention. Such compounds are also subject matter of this invention. They can be used both as intermediate compounds for the chemical synthesis of nuc-macromolecules with one macromolecular marker, e.g., dUTP-PEG-biotin, and as independent compounds for enzymatic reactions, as, for example, nucleotides labeled with only one dye.

Different fluorescent dyes can be used, and their choice is not limited as long as their influence of the enzymatic reaction is not substantial. Examples of such dyes are Rhodamine (Rhodamine 110, Tetramethylrhodamine, available from Fluka-Sigma), cyanine dyes (Cy2, Cy3, Cy3.5, Cy5, Cy5.5, Cy7 available from Amersham Bioscience), coumarine, Bodipy, fluorescein, Alexa Dyes: e.g., Alexa 532, Alexa 548, Alexa 555 (Molecular Probes). Many dyes are commercially available, for instance, from Molecular Probes Europe, Leiden, the Netherlands (hereinafter called Molecular Probes) or from Sigma-Aldrich-Fluka (Taufkirchen, Germany).

Examples of the synthesis of a nuc-macromolecule with a low-molecular marker are given in examples 19, 20, 23, 36, 37, 38.

After the incorporation of the nucleotide component into the nucleic acid chain, the marker coupled to the linker is located according to the invention at a large distance from the nucleic acid strand resulting, for example, in a reduction of the influence of the nucleic acid bases on the fluorescent properties of the dyes. Fluorescent yields of single dyes are thereby less influenced by the local composition of the nucleic acid sequence so that the intensities of signals are more uniform. Besides, the intermolecular quenching of the fluorescence of neighboring nuc-macromolecules has a substantially smaller effect on the nuc-macromolecules, which are closely incorporated together, than in the case of conventionally modified nucleotides.

In one embodiment, the marker comprises several marker units. These marker units can have the same or different properties. For instance, fluorescent dyes with different spectral qualities can be used. In one embodiment, the fluorescent dyes that can form FRET pairs are selected.

Structures with High Mass (Macromolecules)

Nanocrystals

Nanocrystals, e.g. quantum dots, can serve as marker units. Quantum dots with the same or different spectral qualities can be used within the same marker component. Examples of quantum dots are presented in U.S. Pat. Nos. 6,322,901, 6,423,551, 6,251,303, 5,990,479.

Nano- or Micro-particles

Nano- or micro-particles can serve as marker units. The diameters of these particles can range from 1 nm to 2 nm, from 2 nm to 5 nm, from 5 nm to 10 nm, from 10 nm to 20 nm, from 20 nm to 50 nm, from 50 nm to 100 nm, from 100 nm to 200 nm, from 200 nm to 500 nm, from 500 nm to 1000 nm, from 1000 nm to 5000 nm. The material of these particles can, for instance, be pure metals such as gold, silver, aluminum (as instances of particles capable of surface plasmon resonance), Protein-gold_conjugates: J. Anal. Chem. 1998; v. 70, p. 5177-, Nucleic acid-gold_conjugates: J. Am. Chem. Soc. 2001; v. 123, p. 5164-, J. Am. Chem. Soc. 2000; v. 122, p. 9071-, Biochem. Biophys. Res. Commun 2000; v. 274, p. 817-, Anal. Chem. 2001; v. 73, p. 4450-, latex (e.g., Latex-Nano-particles), Anal. Chem. 2000; v. 72, p. 1979-, plastic (Polystyrene), paramagnetic compounds: Zhi Z L et al. Anal. Biochem, 2003; v. 318 (2): p. 236-43, Dressman D et al. Proc Natl Acad Sci U.S.A. 2003, v. 100 (15): p. 8817-22, metal particles, magnetic compounds: Jain K K. Expert Rev Mol. Diagn. 2003; v. 3 (2): p. 153-61, Patolsky F et al. Angew Chem Int Ed Engl 2003; v. 42 (21), p. 2372-2376, Zhao X et al. Anal Chem. 2003; v. 75 (14): p. 3144-51, Xu H et al. J Biomed Mater Res. 2003 Sep. 15; v. 66A(4): p. 870-9, Josephson U.S. Patent No. 2003092029, Kliche WO0119405.

Protein Molecules

Protein molecules can serve as marker units. The proteins comprise the following groups: enzymes (e.g. peroxidase, alkaline phosphotase, urease, beta-galactosidase), fluorescing proteins (e.g. GFP), antigen-binding proteins (e.g. antibodies, tetramers, affibodies (Nord et. al Nature Biotechnology, 1997, v. 15, p. 772-) or their components (e.g. Fab fragments), nucleic acid-binding proteins (e.g. transcription factors).

Nucleic Acid Chains

Nucleic acid chains, including oligonucleotides (modified and non-modified), can act as marker units. The length of these nucleic acid chains should fall preferably within the following ranges (number of nucleotide monomers in a chain): 10 to 20, 20 to 50, 50 to 100, 100 to 200, 200 to 500, 500 to 1000, 1000 to 5000, 5000 to 10000, 10000 to 100000. DNA, RNA, PNA molecules can be used. Nucleic acid chains can carry additional modifications, such as, for example, free amino groups, dyes and other signal-giving molecules, e.g. macromolecular substances, enzymes or nanocrystals (FIG. 7a, c). Modified nucleic acid chains are also commercially available, e.g. from MWG-Biotech. Further examples of macromolecules or macromolecular complexes which can be used, according to the scope of the present invention, as a marker or marker units in the marker component are described in the U.S. Pat. Nos. 4,882,269, 4,687,732, WO 8903849, the U.S. Pat. Nos. 6,017,707, 6,627,469.

Core Component of the Marker

The core component has the function of connecting several structural elements of the nuc-macromolecules. For instance, the core component connects several marker units together. In a further embodiment, linker components can be bound to the core component (FIG. 5).

Constituents

In one embodiment, the core component consists of one or several low molecular compounds. They have the function of connecting the marker units together. A connection between the core component and the marker units can be covalent or affine. With covalent bonding, for instance, compounds with the general structural formula $(F)_m$—R—$(H)_n$ can act as a precursor, where (F) and (H) are reactive groups and (R) a connecting component. The number of such groups and their assembly can vary considerably. Many examples are known to the expert in the field, e.g. connections from the group of crosslinkers ("Chemistry of protein conjugation and crosslinking" Shan S. Wong in 1993 CRC Press Inc). For instance, parts (F) and (H) comprise independently the following groups: NH2 (amino), OH (hydroxy), SH (mercapto), COOH (carboxy), CHO (aldehyde), acrylic or maleimide.

In one embodiment, the core component consists of a water-soluble polymer, whereby the said polymer can consist of the same or different monomers.

The following polymers and their derivates are examples of parts of the core component: polyamides (e.g. polypeptide), polyacrylic acid, polyacrylamides, polyvinyl alcohols, nucleic acids, proteins. These polymers can be linear, globular, e.g. streptavidin or avidin, or can be branched, e.g. dendrimers (FIG. 8a). Also, cross-connected, soluble polymers, for instance, crosslinked polyacrylamides (crosslinker bisacrylamide in combination with polyacrylamide), are suitable.

The core component has in a favored application several coupling positions to which further elements can be bound, e.g. structural marker units or nuc-linker-components.

For instance, polylysine molecules have multiple free amino groups to which several dye molecules, biotin molecules, hapten molecules or nucleic acid chains can be coupled. Polylysines of different molecular mass are commercially available (e.g. 1000-2000 Da, 2000-10000 Da, 10000-50000 Da).

Nucleic acid strands constitute a further example of the core component and these chains have the following length ranges (number of nucleotide monomeres in a chain): 10 to 20, 20 to 50, 50 to 100, 100 to 200, 200 to 500, 500 to 1000, 1000 to 5000, 5000 to 10000. These nucleic acids act as a binding partner for sequence complementary marker-units (FIG. 7b).

In a further embodiment, the core component consists of a dendrimer, e.g. polypropylenimine or polyaminoamine. Examples of other dendrimers are known: Cientifica "Dendrimers", in 2003, Technology white papers No. 6, Klajnert et al. Acta Biochimica Polonica, 2001, v. 48; p 199-, Manduchi et al. Physiol. Genomics 2002, v. 10; p 169-, Sharma et al. Electrophoresis. 2003, v. 24; p 2733-, Morgan et al. Curr Opin drug Discov Devel. 2002; v. 5 (6); p 966-73, Benters et al. Nucleic Acids Res. 2002, v. 30 (2): pE10, Nils et al. J Theor Biol. 1997; v. 187 (2): p 273-84. Many dendrimers are commercially available (Genisphere, www.genisphere.com, Chimera Biotech GmbH).

Further combinations for the core component from the constituents described above are obvious to the specialist.

Coupling of the Marker Units

Marker units can be bound to the core component or to the linker component by a covalent bond, for example, via a crosslinker (Chemistry of protein conjugation and cross linking, S. Wang, 1993, ISBN 0-8493-5886-8, "Bioconjugation: protein coupling techniques for the biomedical sciences", M. Aslam, 1996, ISBN 0-333-58375-2), or via an affine bond, for example, biotin-streptavidin connection or hybridizing of nucleic acid chains or antigen-antibody interaction ("Bioconjugation: protein coupling techniques for the biomedical sciences", M. Aslam, in 1996, ISBN 0-333-58375-2).

In one embodiment, the coupling of the marker units to the core component is conducted already during the synthesis of the nuc-macromolecules.

In another embodiment, the chemically synthesized nuc-macromolecules comprise a marker component consisting only of a core component without marker units. The coupling of marker units to the core component is conducted after the nuc-macromolecules have been incorporated in the nucleic acid chain. Due to the large number of potential binding positions within the core component, the probability of the coupling of the marker units to the core component of incorporated nucleotides is therefore substantially larger in comparison to conventional nucleotide structures. The coupling chemistry depends in detail on the structure of the marker units and the structure of the core component.

Covalent coupling: In one embodiment, the connection between the marker units and the core component can be resistant (example 33), e.g. to temperatures up to 100° C., to pH ranges between 3 and 12, and/or resistant to hydrolytical enzymes (e.g., esterases). In another embodiment of the invention, the connection is cleavable under mild conditions.

Examples of the coupling of nucleic acids to dendrimers (this corresponds to a coupling of marker units to the core component) are described, e.g., in Shchepinov et al. Nucleic Acids Res. 1999; v. 27 (15):p 3035-41, Goh et al. Chem Commun (Camb). 2002; (24): p 2954.

Coupling Between Linker and Marker

The connection between the linker component and the marker depends on the respective structures of the marker units or the structure of the core component. In one embodiment, the linker component is bound directly to the signal-giving or signal-transmitting marker unit (FIG. 4a). The marker can consist of only one or several marker units.

In a further embodiment, one or several linker components are bound to the core component of the marker (FIG. 5d). The marker consists of several marker units.

The connection between the linker component and the marker can be covalent as well as affine. Many examples are known to the specialist, e.g. "Bioconjugation: protein coupling techniques for the biomedical sciences", M. Aslam, in 1996, ISBN 0-333-58375-2. "Chemistry of protein conjugation and crosslinking" Shan S. Wong in 1993 CRC Press Inc).

Covalent coupling: In one embodiment, the connection between the linker component and the marker can be resistant to, e.g., temperatures up to 130° C., pH ranges between 1 and 14, and/or resistant to hydrolytic enzymes (e.g. proteases, estarases). In another embodiment, the connection is cleavable under mild conditions.

Ratio of Nuc-components in a Nuc-macromolecule

One nuc-macromolecule can comprise on average 1 to 2, 2 to 5, 5 to 10, 10 to 30, 30 to 100, 100 to 1000 nuc-components.

In one embodiment, all nuc-macromolecules have the same number of nuc-components per one nuc-macromolecule. For instance, a maximum of 4 biotin molecules can be bound per one strepavidin molecule; at a saturating concentration of nuc-linker components, a uniform population of nuc-macromolecules can be obtained.

In another embodiment, a nuc-macromolecule population has a defined average number of nuc-components per one nuc-macromolecule, however, in the population itself there is dispersion in the actual occupation of the nuc-macromolecules by nuc-components. In this case, the number of nuc-components per one nuc-macromolecule displays an average.

Ratio of Marker Units in a Nuc-macromolecule

The number of marker units in one nuc-macromolecule falls within the following ranges: 1 and 2, 2 and 5, 5 and 20, 20 and 50, 50 and 100, 100 and 500, 500 and 1000, 1000 and 10000, 10000 and 100000. In one embodiment, nuc-macromolecules have a definite number of signal-giving units per one marker. In another embodiment, a population of nuc-macromolecules has a varying number of marker units per one nuc-macromolecule and it does not need to have a definite value for every single nuc-macromolecule in a population.

In one embodiment, all the nuc-macromolecules have the same number of marker units per one nuc-macromolecule. For instance, a maximum of 4 biotin molecules can be bound per one strepavidin molecule, see "Avidin-Biotin-Technology", Methods in Enzymology v. 184, 1990.

In another embodiment, a nuc-macromolecule population has a defined average number of marker units per one nuc-macromolecule, however, in the population itself, there is dispersion in the actual occupation of the nuc-macromolecules by marker units. An increasingly more uniform occupation of the nuc-macromolecules by marker units can be achieved by the use of saturating concentration during the synthesis of the marker component.

For instance, in cases where only qualitative detection is important, the exact number of marker units per one nuc-macromolecule has a subordinate role. In such cases the availability of a stable signal is important in itself.

To an expert in the field it should be evident that the said marker components have substantially greater molecule size and molecule measures, than the respective nuc-components themselves. Other examples of macromolecular marker components should readily suggest themselves to an expert in the field.

Substrate Properties of the Nuc-macromolecules

The nuc-component bound to a nuc-macromolecule can serve as a substrate for different enzymes. For instance, a nucleoside triphosphate as the nuc-component serves as a substrate for a polymerase, so that the nuc-component can be incorporated in a growing strand by a polymerase and therefore the whole nuc-macromolecule is coupled covalently to the strand.

Further examples of enzymes are kinases, phosphorylases and transferases.

As the monomer part of a nucleic acid chain, nuc-macromolecules can likewise serve as substrates for enzymes, for instance, for 3'- or 5'-exonucleases or endonucleases ("Molecular cloning" in 1989, Ed. Maniatis, Cold Spring Harbor Laboratory) or for the other suitable partial activities of polymerases, as for example described for real time PCR (S. Meuer "Rapid cycle real time PCR", Springer 2004, ISBN 3-540-66736-9, T. Weissensteiner "PCR-Technology: current innovations" CRC Press 2004 ISBN 0-8493-1184-5).

The substrate properties of the nuc-component(s) determine the substrate properties of the nuc-macromolecules. Thus, the nuc-component can serve as a terminator, so that only one single nuc-macromolecule can be incorporated. In another embodiment, the nuc-component serves as a reversible terminator, which allows for an extension reaction controlled step-by-step, as described, for example, in Ju et al. the U.S. Pat. No. 6,664,079, Tcherkassov WO 02088382.

As the monomer part of a nucleic acid chain, nuc-components can determine its enzymatic-properties, such as exonuclease activity. In another embodiment, not only the nuc-components of the nuc-macromolecules, but also the neighboring nucleotides, determine the enzymatic properties, e.g. in the case of endonucleases.

Function of the Markers

In one embodiment, the macromolecular marker component can have a signal-giving function. In another embodiment, it has a signal-transmitting function. In a further embodiment, it has a catalytic function. In a still further embodiment, it has an affine function. In a still further embodiment, the marker combines more than just one function, e.g. signal-giving as well as signal-transmitting function. Further combinations will be obvious.

In the case of signal-giving function, the marker component contains constituents coupled already during the chemical synthesis to nuc-macromolecules (see example 33).

In the case of signal-transmitting function, the marker component contains constituents that allow for reaction with signal-giving molecules, so that they can develop their signaling properties after this reaction (see example 32). For instance, a marker component consists of several biotin molecules, e.g. 100 Biotin molecules. After the incorporation of the nuc-macromolecules, a detection reaction can take place with modified streptavidin molecules. In another example, nucleic acid chains display the signal-transmitting function: after the incorporation of nuc-macromolecules, a hybridisation of uniform oligonucleotides with detectable units, e.g. fluorescent dyes (synthesized by MWG-Biotech), to the marker component can take place. In a further example, amino or mercapto groups have the signal-transmitting function, e.g. 50 amino groups per marker. After the incorporation of the nuc-macromolecules in the nucleic acid chain, a chemical modification with reactive components is conducted, e.g. with dyes, as described, for example, for incorporated allyl-amino-dUTP, Diehl et al. Nucleic Acid Research, in 2002, v. 30, No. 16 e79.

In another embodiment, the macromolecular marker component has a catalytic function (in the form of an enzyme or ribozyme). Different enzymes can be used, e.g. peroxidases or alkaline phosphatases. Due to the coupling of the particular enzyme to the nuc-component, after the incorporation of nuc-macromolecules to the nucleic acid strand, this enzyme is bonded covalently to the strand, also.

In a further embodiment, a macromolecular marker component has an affinity functionality to another molecule. Examples of such markers are streptavidin molecules, antibodies or nucleic acid chains (see example 30 or 32).

Low Molecular Marker

The state-of-the-art labeling of nucleotides, for instance, with one or two biotin molecules, one or two dye molecules, one or two hapten molecules (e.g., digoxigenin).

Conventionally modified nucleotide- a nucleotide with a linker (average length between 5 and 30 atoms) and a marker. A conventionally modified nucleotide usually carries a marker with low molecular weight, e.g. one dye molecule or one biotin molecule.

To demonstrate the fact that a simple combination of a conventionally modified nucleotide with a macromolecular marker leads to the abolition of the substrate properties of the nucleotide, there will be a description of nucleotides which do indeed carry a macromolecular marker, but a short linker with an average length of 5 to 30 atoms. Such nucleotides are designated as conventionally modified nucleotides. A plain combination between a conventionally modified nucleotide and a macromolecular marker is not sufficient, according to this invention, to fulfill the requirements of the definition of nuc-macromolecules.

On the contrary, nuc-macromolecules can be defined by a combination of one or several nuc-components, one or several long linkers and a marker.

Enzymes (Polymerases)

In one embodiment, the nuc-macromolecules can be used as substrates for enzymes. Polymerases represent frequently used enzymes, which utilize nucleotides as substrates. They will be dealt with further as representative examples of other nucleotide-utilizing enzymes. One of the central abilities of polymerases consists in covalent coupling of nucleotide monomers to a polymer. Furthermore, the synthesis can be template-dependent (as for example DNA or RNA synthesis with DNA- or RNA-dependent polymerases) as well as independent of templates, e.g. terminal transferases (J Sambrook "Molecular Cloning" 3. Ed. CSHL Press in 2001).

If RNA is used as a substrate (e.g., mRNA) in the sequencing reaction, commercially available RNA-dependent DNA polymerases can be used, e.g. AMV reverse transcriptase (Sigma), M-MLV reverse transcriptase (Sigma), HIV reverse transcriptase without RNAse activity. For certain applications, reverse transcriptases can be essentially free of RNAse activity ("Molecular cloning" in 1989, Ed. Maniatis, Cold Spring Harbor Laboratory), e.g. for use in mRNA labeling for hybridisation applications.

If DNA is used as a substrate (e.g. cDNA), all the following polymerases are suitable in principle: DNA-dependent DNA polymerases with or without 3'-5' exonuclease activity ("DNA-Replication" in 1992 Ed. A. Kornberg, Freeman and company NY), e.g. modified T7-Polymerase of the type "Sequenase version 2" (Amersham Pharmacia Biotech), Klenow fragment of the DNA-Polymerase I with or without 3'-5' exonuclease activity (Amersham Pharmacia Biotech), polymerase Beta of different origin ("Animal Cell DNA polymerases" in 1983, Fry M., CRC Press Inc, commercially available from Chimerx), thermostable polymerases such as, for example, Taq Polymerase (GibcoBRL), proHA-DNA-Polymerase (Eurogentec), Vent, Vent exo-minus, Pfu, Thermosequenase, Pwo-Polymerase etc. (Promega).

DNA-dependent RNA polymerases can also be used, e.g. E. coli RNA polymerase, T7 RNA polymerase, SP6 RNA polymerase.

Polymerases with 3'- or 5'-exonuclease activity can be used in certain applications (e.g. with real-time PCR).

In the following description, DNA-dependent DNA polymerases will be considered as examples of polymerases.

Cleavable Compound

A compound which is cleavable under mild conditions. This compound can represent a part in the linker and can be cleavable in one or several positions. It can be a chemically cleavable bond, such as, for example, disulfide, acetal, thioester bonds (Short WO 9949082, Tcherkassov WO 02088382). It can also be a photo-chemically cleavable compound (Rothschild WO 9531429). It can also be an enzymatically cleavable compound (for instance, a peptide or polypeptide bond, Odedra WO 0192284), cleavable by peptidases, a poly- or oligo-saccharide bond, cleavable by disaccharidases, whereas the cleavage can be achieved by a specific enzyme between certain monomers of the cleavable bonds.

Several examples of cleavable compounds are known. The synthesis of such a compound is described, for instance, in (Tcherkassov WO 02088382, Metzker et al. Nucleic Acid Research 1994, v. 22, p. 4259-, Canard et al. Genes, 1994, v. 148, p. 1, Kwiatkowski U.S. Pat. No. 6,255,475, Kwiatkowski WO 0125247, Parce WO 0050642). A cleavable compound can be a part of the linker or can form the connecting part of the linker to the nucleotide, or the connecting part of the linker component to the marker component, or the connection between marker units and the core component.

DNA

Deoxyribonucleic acid of different origin and different length (e.g. oligonucleotides, polynucleotides, plasmides, genomic DNA, cDNA, ssDNA, dsDNA)

RNA

Ribonucleic acid dNTP

2'-deoxynucleoside triphosphate, as a substrate for DNA polymerases and reverse-transcriptases, e.g. dATP, dGTP, dUTP, dTTP, dCTP.

NTP

Ribonucleoside triphosphate, as a substrate for RNA polymerases, UTP, CTP, ATP, GTP.

NT

Abbreviation "NT" is used for the description of the length of a particular nucleic acid sequence, e.g. 1000 NT. In this case "NT" means nucleoside monophosphates.

The plural is formed by the addition of the suffix "-s"; "NT" means, for example, "one nucleotide", "NTs" means "several nucleotides".

NAC

Nucleic acid chain (NSK abbreviation stands for German "Nukleinsäurekette"), DNA or RNA.

Term "the Whole Sequence"

The whole sequence is the sum of all the sequences in one experiment; it can comprise originally one or several NACs. Also, the whole sequence can display parts or equivalents of another sequence or sequence populations (e.g., mRNA, cDNA, Plasmid DNA with insert, BAC, YAC) and can originate from one species or various species.

NACF

The nucleic acid chains fragment (NSKF abbreviation stands for German "Nukleinsäurekettenfragment") (DNA or RNA) which corresponds to a part of the whole sequence, NACFs—the plural form—nucleic acid chain fragments. The sum of the NACFs forms an equivalent to the whole sequence. The NACFs can be, for instance, fragments of the whole sequence (DNA or RNA), which result after a fragmentation step.

Primer Binding Site (PBS)

A PBS is the part of the sequence in the NAC or NACF to which the primer binds.

Reference Sequence

A reference sequence is an already known sequence, divergences from which in the analysed sequence or sequences (e.g. whole sequence) have to be determined. Reference sequences can be found in databases, such as, for example, the NCBI database.

Tm

Melting temperature

Steric Hindrance

A sterically demanding group which (by its chemical structure) changes the properties of the nucleotides coupled with this group in such a way that these nucleotides cannot be inserted successively by a polymerase in an extension reaction. A sterically demanding group coupled to the nucleotide base can lead to the impedance of further synthesis. Biotin, digoxigenin and fluorescent dyes like fluorescein, tetramethylrhodamine, Cy3-dye, are examples of such sterically demanding groups (Zhu et al. Cytometry in 1997, v. 28, p. 206, Zhu et al. NAR 1994, v. 22, p. 3418, Gebeyehu et al., NAR 1987, v. 15, p. 4513, Wiemann et al. Analytical Biochemistry in 1996, v. 234, p. 166, Heer et al. BioTechniques 1994 v. 16 p. 54).

PNA

Peptide Nucleic Acid

BRIEF DESCRIPTION OF THE DRAWINGS

FIG. 1 is a schematic of an aspect of the invention, depicting a compound comprising one or more nuc-components, one or more linker components, and a marker component.

FIG. 2 is a schematic of an aspect of the disclosure, depicting a compound comprising one or more nuc-components, one or more linker components, and a marker component.

FIG. 3A is a schematic of an aspect of the disclosure, wherein the nuc-component comprises Base, which is selected independently from the group of adenine, or 7-deazaadenine, or guanine, or 7-deazaguanine, or thymine, or cytosine, or uracil, or their modifications, and wherein (L) is the linkage between the nuc-component and the linker component (coupling unit L), X is the coupling position of the coupling unit (L) to the base and R1, R2, R3, R4 and R5 are independent substituents. FIG. 3B is a schematic of an aspect of the disclosure, wherein Base is selected independently from the group of adenine, or 7-deazaadenine, or guanine, or 7-deazaguanine, or thymine, or cytosine, or uracil, or their modifications capable of enzymatic reactions and wherein R1-R5 are independent substituents.

FIG. 5A-D depict embodiments of the disclosure wherein the core component of the molecule provides the connection to one or several nuc-linker components.

FIG. 6A depicts an embodiment of the disclosure wherein chemically reactive groups serve as signal-transmitting structural units of the molecule. FIG. 6B depicts an embodiment wherein the reactive groups are modified with signal-producing elements.

FIGS. 8A and 8B depict embodiments of the disclosure wherein polymers or their derivatives constitute the core component of the molecule and wherein the polymers are branched and linked to marker component(s) (FIG. 8B)

FIG. 10A and 10B are schematics showing base-modified nucleotide analogs. FIG. 10A depicts a dUTP analog comprises a disulfide bond that can react with other thiols in a thiol exchange reaction under mild conditions resulting in a formation of a new cleavable bond. FIG. 10B is a modified dCTP analog.

FIGS. 11, 12, 13 and 14 are schematics showing that ribonucleotides, 2'-deoxyribonucleotide or 2',3'-dideoxyribonucletide can be used to generate base-modified nucleotide analogs.

FIG. 24A depicts TTP-3'-O-Propionate-SH. FIG. 24B depicts TTP-3'-Amino-PDTP.

FIG. 32 depicts (dUTP-M-PEG-Biotin)4-SA-Cy2 and (dUTP-M-PEG-Biotin)4-SA.

FIG. 33 depicts (dUTP-AA-PEG-Biotin)4-SA-alkaline phosphatase.

FIG. 34 depicts (dUTP-AA-PEG-Biotin)4-SA-QDot.

FIG. 35A depicts (dUTP-AA-PEG-biotin)2-(dT31-TEG-biotin)2-SA-CY2; FIG. 35B shows that complementary nucleic acids, having a signal-giving function, can be hybridized to such an oligonucleotide.

FIG. 36 depicts (dUTP-AA-SS-PEG-biotin)4-SA and (dUTP-AA-SS-PEG-biotin)4-SA-Cy2.

FIG. 37A depicts dCTP-PA-PEG-maleimide-S-oligo-dT30. FIG. 37B shows Complementary nucleic acids having a signal-giving function can be hybridized to such an oligonucleotide.

DETAILED DESCRIPTION

Figure 4:
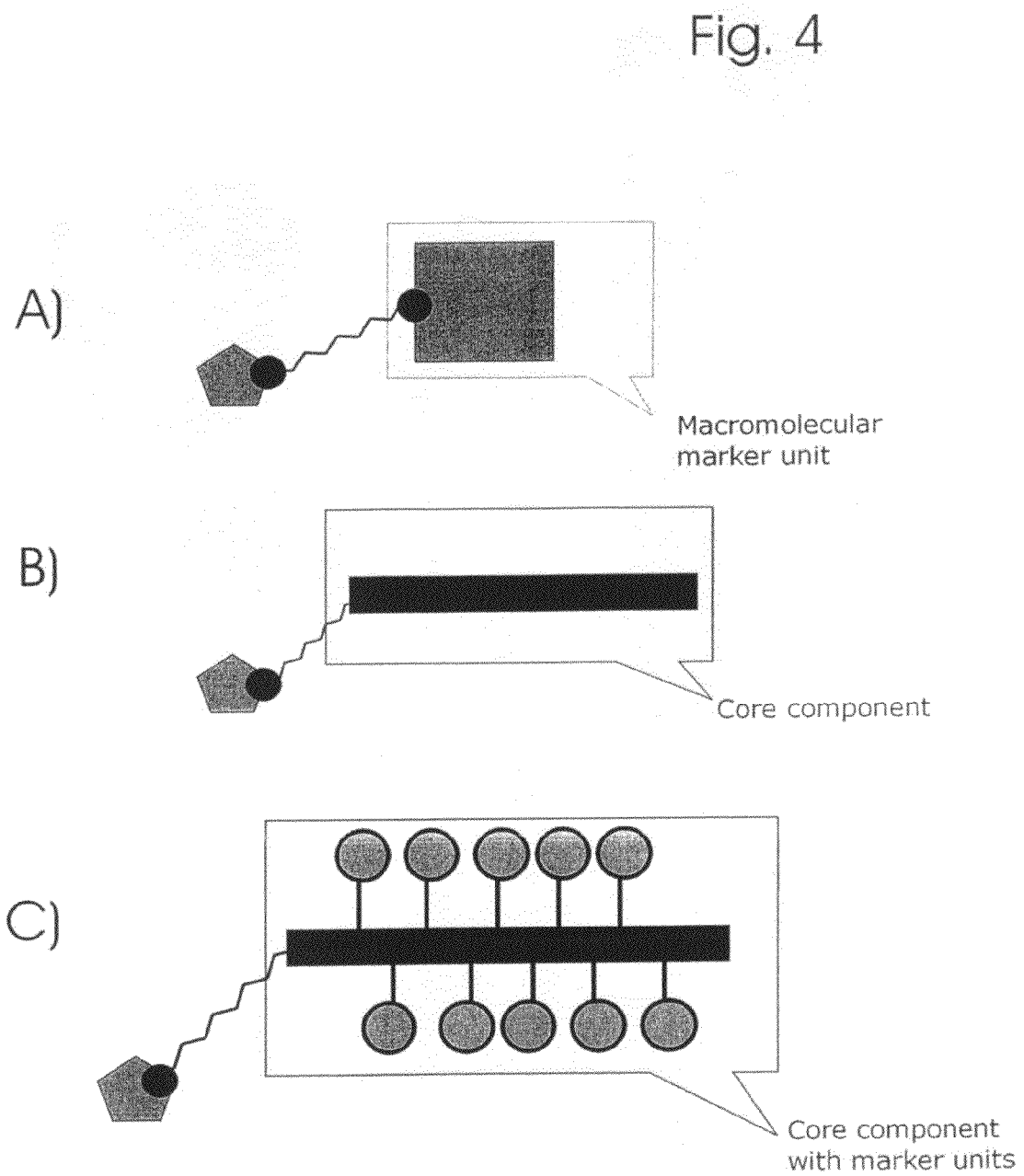
FIG. 4A is a schematic of an embodiment of the disclosure wherein the linker component is bound directly to the signal-giving or signal-transmitting marker unit. The marker can consist of only one or several marker units.
FIG. 4B is a schematic of an embodiment of the disclosure showing linkage of the marker core to the linker component.
FIG. 4C depicts an embodiment to wherein several marker units are combined into one marker component, which are bound to a framework, the core component of the marker.
Figure 7:
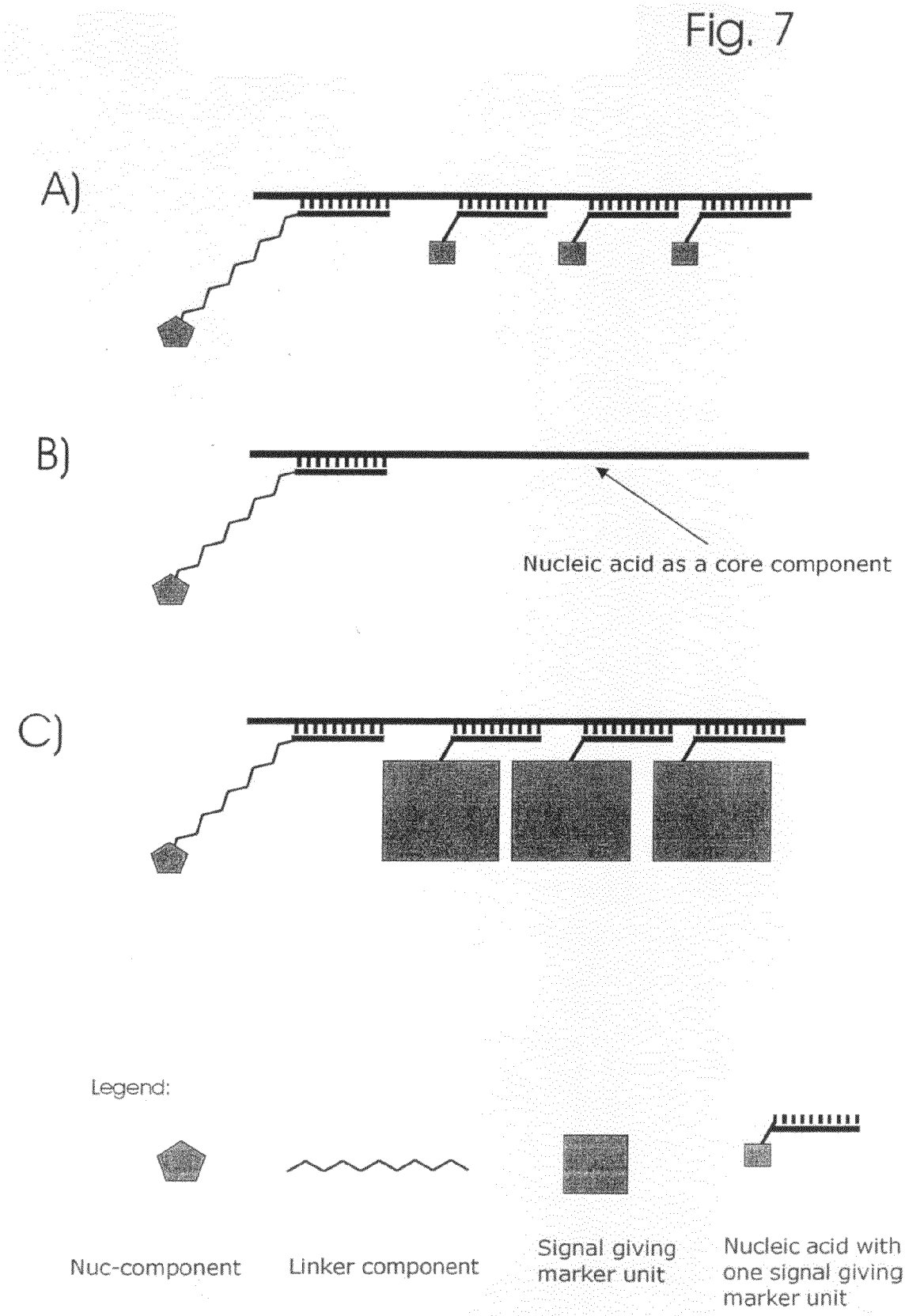
FIGS. 7A and 7C depict embodiments of the disclosure wherein nucleic acid chains, including oligonucleotides (modified and non-modified), act as marker units.
FIG. 7B depicts an embodiment wherein nucleic acids, which constitute a part of the core component act as a binding partner for sequence complementary marker-units.
Figure 9:
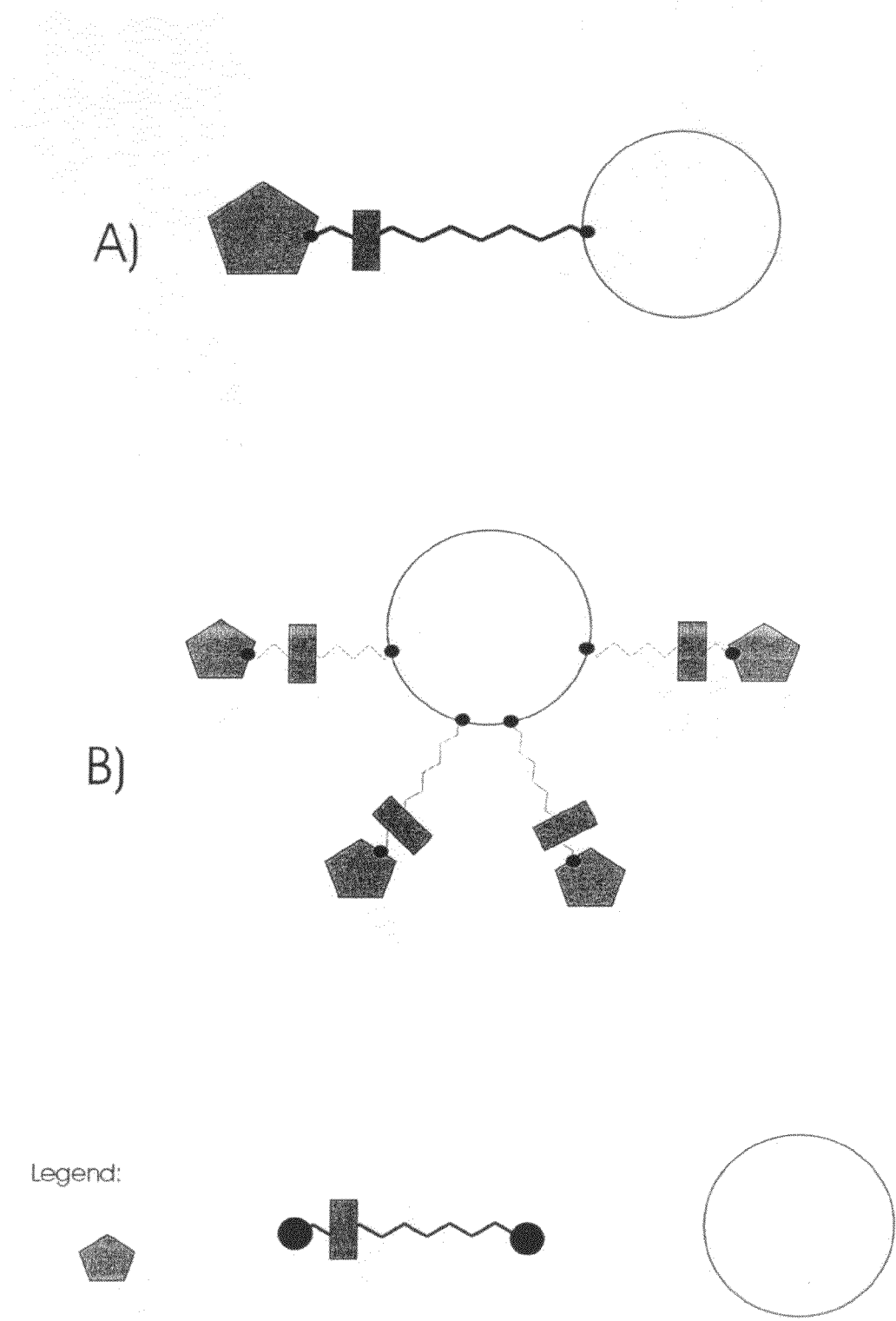
FIGS. 9A and 9B depict embodiments of the disclosure wherein the linker comprises functional groups or parts that are cleavable.
Figure 13:
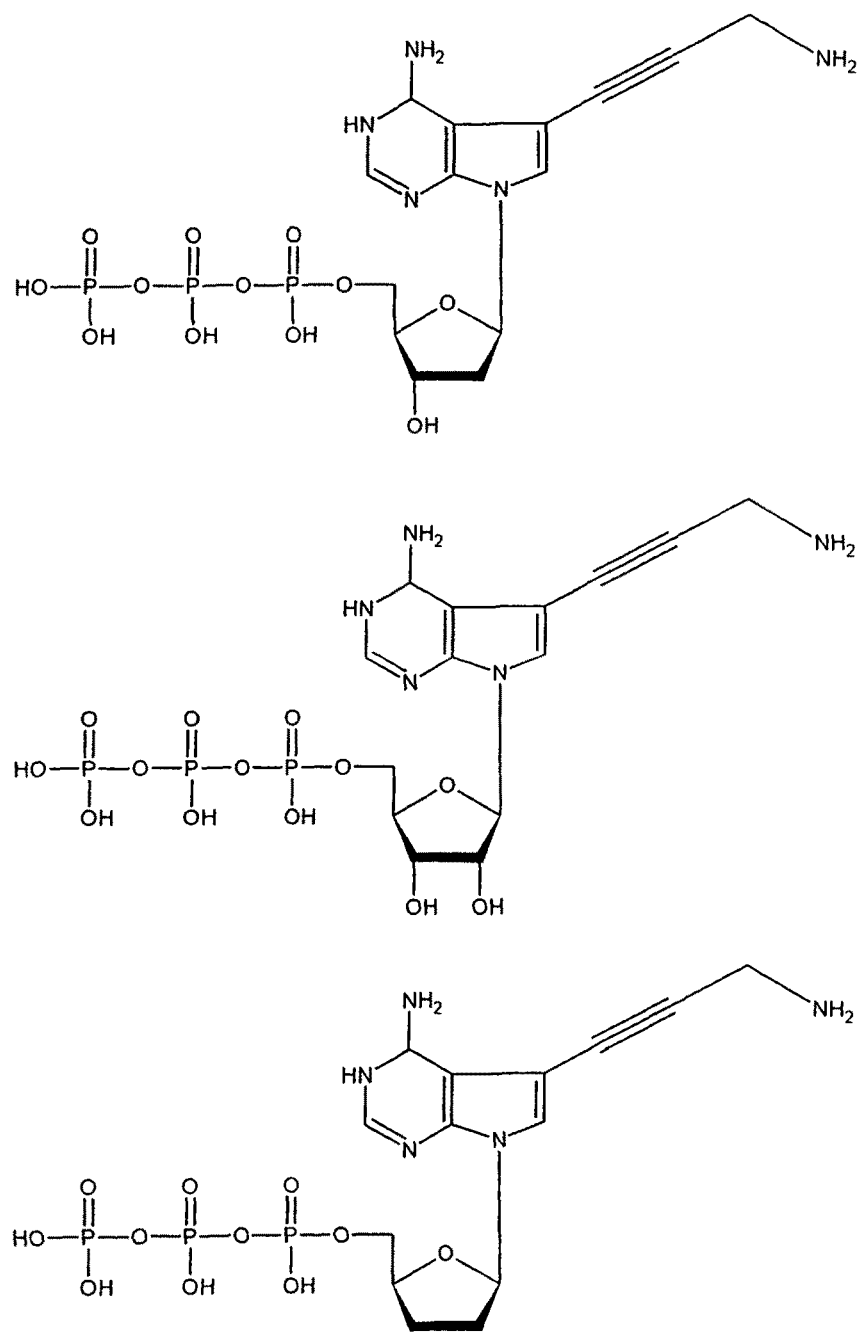
Figure 14:
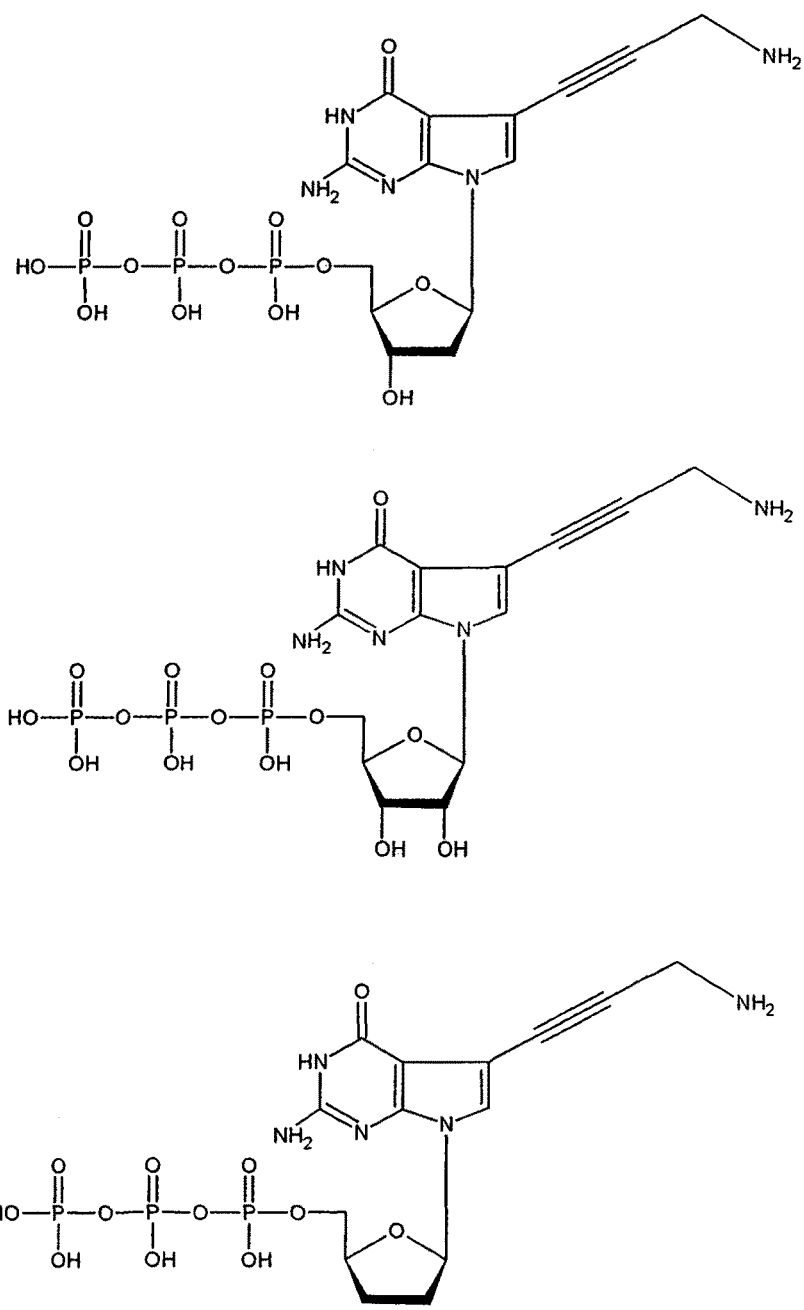

The invention describes a new class of modified nucleotides.

1. One aspect of the invention relates to macromolecular compounds with the structure:

(nuc-linker)$_n$-marker wherein:
Nuc is a nucleotide or nucleoside (nuc-component)
Linker is a linker component comprising the following parts:
  a) Coupling unit L is a part of the linker which provides the linkage between nuc and the rest of the linker
  b) Polymer is a part of the linker which is a water-soluble polymer with an average length between 100 and 20,000 atoms (chain atoms)
  c) Coupling unit T is a part of the linker which provides the linkage between the marker and the rest of the linker
Marker is a marker component
(n) is a positive integer between 1 and 100

2. A further aspect of the invention relates to macromolecular compounds according to aspect 1, wherein the nuc-component comprises the following structures (FIG. 3A), wherein:
Base is selected independently from the group of adenine, or 7-deazaadenine, or guanine, or 7-deazaguanine, or thymine, or cytosine, or uracil, or their modifications, wherein (L) is the linkage between the nuc-component and the linker component (coupling unit L) and X is the coupling position of the coupling unit (L) to the base.
$R_1$—is H
$R_2$—is selected independently from the group of H, OH, halogen, $NH_2$, SH or protected OH group
$R_3$—is selected independently from the group of H, OH, halogen, $PO_3$, SH, $N_3$, $NH_2$, O—$R_{3-1}$, P(O)$_m$—$R_{3-1}$ ((m) is 1 or 2), NH—$R_{3-1}$, S—$R_{3-1}$, Si—$R_{3-1}$ wherein $R_{3-1}$ is a chemically, photochemically or enzymatically cleavable group or comprises one of the following modifications: —CO—Y, —CH$_2$—O—Y, —CH$_2$—S—Y, —CH$_2$—N$_3$, —CO—O—Y, —CO—S—Y, —CO—NH—Y, —CH$_2$—CH=CH$_2$, wherein Y is an alkyl, for instance (CH$_2$)$_n$—CH$_3$ wherein n is a number between 0 and 4, or a substituted alkyl, for instance with halogen, hydroxy group, amino group, carboxy group.
$R_4$—is H or OH
$R_5$—is selected independently from the group of OH, or a protected OH group, or a monophosphate group, or a diphosphate group, or a triphosphate group, or is an alpha thiotriphosphate group.

3. A further aspect of the invention relates to macromolecular compounds according to aspect 1, wherein the nuc-component comprises the following structures (FIG. 3B),
Wherein:
Base is selected independently from the group of adenine, or 7-deazaadenine, or guanine, or 7-deazaguanine, or thymine, or cytosine, or uracil, or their modifications capable of enzymatic reactions.
$R_1$—is H
$R_2$—is selected independently from the group of H, OH, halogen, $NH_2$, SH or protected OH group
$R_3$—is selected independently from the group of O—$R_{3-2}$-L, P(O)$_m$—$R_{3-2}$-L and (m) is 1 or 2, NH—$R_{3-2}$-L, S—$R_{3-2}$-L, Si—$R_{3-2}$-L, wherein $R_{3-2}$ is the coupling position of the linker to the nucleotide and L is the coupling unit (L) of the linker.
$R_4$—is H or OH
$R_5$—is selected independently from the group of OH, or a protected OH group, or a monophosphate group, or a diphosphate group, or a triphosphate group, or is an alpha-thiotriphosphate group.

4. A further aspect of the invention relates to macromolecular compounds according to aspect 1, wherein the nuc-component comprises the following structures (FIG. 3B),
Wherein:
Base is selected independently from the group of adenine, or 7-deazaadenine, or guanine, or 7-deazaguanine, or thymine, or cytosine, or uracil, or their modifications capable of enzymatic reactions.
$R_1$—is H
$R_2$—is selected independently from the group of H, OH, halogen, $NH_2$, SH or protected OH group
$R_3$—is selected independently from the group of H, OH, halogen, $PO_3$, SH, $NH_2$, O—$R_{3-1}$, P(O)$_m$—$R_{3-1}$ ((m) is 1 or 2), NH—$R_{3-1}$, S—$R_{3-1}$, Si—$R_{3-1}$ wherein $R_{3-1}$ is a chemically, photochemically or enzymatically cleavable group.
$R_4$—is H or OH
$R_5$—is selected independently from the group of O—$R_{5-1}$-L, or P—(O)$_3$—$R_{5-1}$-L (modified monophosphate group), or P—(O)$_3$—P—(O)$_3$—$R_{5-1}$-L (modified diphosphate group) or P—(O)$_3$—P—(O)$_3$—P—(O)$_3$—$R_{5-1}$-L (modified triphosphate group), wherein $R_{5-1}$ is the coupling position of the coupling unit (L) to the nucleotide and coupling unit (L) is a linkage between nuc-component and the rest of the linker.

5. A further aspect of the invention relates to macromolecular compounds according to aspects 1 to 4, wherein the coupling unit (L) of the linker comprises the following structural elements:
$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—

$R_7$, $R_6$—$(CH_2)_n$—$R_7$, $R_6$-A-$(CH_2)_n$—$R_7$, $R_6$—$(CH_2)_n$—B—$R_7$, $R_6$—$(CH=CH—)_n$—$R_7$, R-(A-CH=CH—$)_n$—$R_7$, $R_6$—(CH=CH—B—$)_n$—$R_7$, $R_6$—(CH=CH—$CH_2$—B—$)_n$—$R_7$, $R_6$-A-CH=CH—$(CH_2$—$)_n$—$R_7$, $R_6$—(—CH=CH—$CH_2)_n$—B—$R_7$, $R_6$—(C≡C—$)_n$—$R_7$, $R_6$-(A-C≡C—$)_n$—$R_7$, $R_6$-(A-C≡C—$CH_2)_n$—$R_7$, $R_6$—(C≡C—B—$)_n$—$R_7$, $R_6$—(C≡C—$CH_2$—B—$)_n$—$R_7$, $R_6$-(A-C≡C—$CH_2$—$)_n$—$R_7$, $R_6$—(—C≡C—$CH_2)_n$—B—$R_7$, $R_6$—(—C≡C—$CH_2$—$CH_2)_n$—B—$R_7$ wherein $R_6$ is the nuc-component, $R_7$ is the rest of the linker, and A and B comprise independently the following structural elements: —NH—, —O—, —S—, —SS—, —CO—NH—, —NH—CO—, —CO—O—, —O—CO—O, —CO—S—, —S—CO—, —P(O)$_2$—, —Si—, —$(CH_2)_n$—, wherein (n) ranges from 1 to 5, a photolabile group 6. A further aspect of the invention relates to macromolecular compounds according to aspects 1 to 5, wherein the linker-component comprises a water-soluble polymer.

7. A further aspect of the invention relates to macromolecular compounds according to aspect 6, wherein the linker-component comprises water-soluble polymers selected independently from the following group:
polyethylene glycol (PEG), polysaccharides, dextran, polyamides, polypeptides, polyphosphates, polyacetates, polyalkyleneglycoles, copolymers from ethyleneglycol and propyleneglycol, polyolefinic alcohols, polyvinylpyrrolidones, poly(hydroxyalkylmethacrylamides), polyhydroxyalkylmethacrylates, poly(x-hydroxy) acids, polyacrylic acid, polyacrylamide, polyvinylalcohol.

8. A further aspect of the invention relates to macromolecular compounds according to aspects 1 to 7, wherein the average length of a linker component ranges between 50 to 100, 100 to 200, 200 to 500, 500 to 1000, 1000 to 2000, 2000 to 10000, 10000 to 50000 atoms (chain atoms).

9. A further aspect of the invention relates to macromolecular compounds according to aspects 1 to 8, wherein a marker component has one of the following functions: signal-giving function, signal-transmitting function, catalytic function or affine function.

10. A further aspect of the invention relates to macromolecular compounds according to aspects 1 to 9, wherein a marker component consists of one structural marker unit.

11. A further aspect of the invention relates to macromolecular compounds according to aspects 1 to 9, wherein a marker component consists of several structural marker units bonded to a core component.

12. A further aspect of the invention relates to macromolecular compounds according to aspects 10 or 11, wherein a structural marker unit independently comprises one of the following structural elements: biotin, hapten, radioactive isotope, rare-earth atom, dye, fluorescent dye.

13. A further aspect of the invention relates to macromolecular compounds according to aspects 10 or 11, wherein a structural marker unit independently comprises one of the following elements: nanocrystals or their modifications, proteins or their modifications, nucleic acids or their modifications, particles or their modifications.

14. A further aspect of the invention relates to macromolecular compounds according to aspect 13, wherein a structural marker unit comprises one of the following proteins:
enzymes or their conjugates or modifications,
antibodies or their conjugates or modifications,
streptavidin or its conjugates or modifications,
avidin or its conjugates or modifications 15. A further aspect of the invention relates to macromolecular compounds according to aspect 13, wherein a structural marker unit comprises one of the following types of nucleic acid chains: DNA, RNA, PNA, wherein the length of nucleic acid chains ranges between 10 and 10,000 nucleotides or their equivalents.

16. A further aspect of the invention relates to macromolecular compounds according to aspects 11 to 15, wherein the core component of the marker component independently comprises one of the following elements: water-soluble polymer from the group of: polyamides (e.g. polypeptides), polyacrylic acid and its derivates, polyacrylamides and their derivates, polyvinylalcohols and their derivates, nucleic acids and their derivates, streptavidin or avidin and their derivates, dendrimeres, whereas these elements can be linear or branched or crosslinked with each other.

17. A further aspect of the invention relates to macromolecular compounds according to aspects 1 to 9, 11 to 16, wherein the linkage between several structural marker units and the core component is covalent or affine.

18. A further aspect of the invention relates to macromolecular compounds according to aspects 1 to 10, wherein the linkage between the said structural marker units and the linker is covalent or affine.

19. A further aspect of the invention relates to macromolecular compounds according to aspects 1 to 9, 11 to 17, wherein the linkage between the core component and the linker is covalent or affine.

20. A further aspect of the invention relates to macromolecular compounds according to aspects 1 to 19, wherein only one nuc-component with one linker component is linked to the marker component, wherein the linker length ranges between 50 to 100, 100 to 200, 200 to 500, 500 to 1000, 1000 to 2000, 2000 to 5000 atoms.

21. A further aspect of the invention relates to macromolecular compounds according to aspects 1 to 20, wherein only one nuc-component with one linker component is linked to the marker component, wherein the linker length ranges between 50 to 100, 100 to 200, 200 to 500, 500 to 1000, 1000 to 2000, 2000 to 5000 atoms and the linker component comprises one or several compounds that are cleavable under mild conditions.

22. A further aspect of the invention relates to macromolecular compounds according to aspects 1 to 21, wherein only one nuc-component with one linker component is linked to the marker component, wherein the linker length ranges between 50 to 100, 100 to 200, 200 to 500, 500 to 1000, 1000 to 2000, 2000 to 5000 atoms and one or several parts of the nuc-macromolecule are modified in such a way, that only one nuc-component can be incorporated into the growing strand.

23. A further aspect of the invention relates to macromolecular compounds according to aspects 1 to 19, wherein several nuc-components are each coupled to one marker component via a linker, wherein the length of each respective linker component ranges between 50 to 100, 100 to 200, 200 to 500, 500 to 1000, 1000 to 2000, 2000 to 5000 atoms.

24. A further aspect of the invention relates to macromolecular compounds according to aspects 1 to 19, 23, wherein several nuc-components are each coupled to one marker component via a linker, wherein the length of each respective linker component ranges between 50 to 100, 100 to 200, 200 to 500, 500 to 1000, 1000 to 2000, 2000 to 5000 atoms and each respective linker component comprises one or several compounds that are cleavable under mild conditions.

25. A further aspect of the invention relates to macromolecular compounds according to aspects 1 to 19, 23, 24, wherein several nuc-components are each coupled to one marker component via a linker, wherein the length of each respective linker component ranges between 50 to 100, 100 to 200, 200 to 500, 500 to 1000, 1000 to 2000, 2000 to 5000 atoms, and one or several parts of the nuc-macromolecule are modified in such a way that only one nuc-component can be incorporated into the growing nucleic acid chain.

26. A further aspect of the invention relates to oligonucleotides or polynucleotides comprising at least one nuc-macromolecule according to aspects 1 to 25 per one nucleic acid chain.

27. A further aspect of the invention relates to oligonucleotides or polynucleotides according to aspect 26, wherein oligo- or polynucleotides are RNA or DNA or PNA and their length ranges between 5 and 50,000 nucleotides.

28. A further aspect of the invention relates to a method for modifying of nucleic acid chains, wherein nuc-macromolecules according to aspects 1 to 25 are used for the coupling.

29. A further aspect of the invention relates to a method according to aspect 28, wherein the modification is accomplished by an enzymatic coupling and the reaction mixture comprises the following components:
   at least one type of nuc-macromolecules or their intermediate stages according to the aspects 1 to 25, wherein every type of nuc-macromolecule is distinctively labeled,
   at least one population of the nucleic acid chains,
   at least one type of enzyme for coupling nuc-macromolecules to the nucleic acid chains, 30. A further aspect of the invention relates to a method according to aspect 28, wherein the modification is accomplished by an enzymatic coupling and the reaction mixture comprises the following components:
   at least one type of nuc-macromolecules or their intermediate stages according to the aspects 1 to 25, wherein every type of nuc-macromolecule is distinctively labeled,
   at least one population of the nucleic acid chains,
   at least one type of enzyme for coupling nuc-macromolecules to the nucleic acid chains,
   at least one other type of nucleoside triphosphates.

31. A further aspect of the invention relates to a method according to aspects 29, 30, wherein the said type of enzyme independently comprises one of the following groups: DNA-polymerases, RNA-polymerases, terminal transferases.

32. A further aspect of the invention relates to a method according to aspect 30, wherein the "other type" of nucleoside tri-phosphates is independently selected from the group of ribonucleoside tri-phosphates (ATP, GTP, UTP, CTP), of 2'-deoxyribonucleoside triphosphates (dATP, dUTP, dTTP, dCTP, dGTP), of 2',3'-dideoxynucleoside triphosphates (ddATP, ddGTP, ddUTP, ddCTP, ddTTP).

33. A further aspect of the invention relates to a method according to aspect 32, wherein the "other type" of nucleoside tri-phosphates is conventionally modified nucleotides with a label, wherein the said label is independently selected from the group of fluorescent dye, biotin, hapten or radioactive element.

34. A further aspect of the invention relates to a method according to aspects 28 to 33, wherein at least two different populations of nucleic acid chains are present 35. A further aspect of the invention relates to a method according to aspect 34, wherein at least one of the populations of the nucleic acid chains has a primer function and at least one population of the nucleic acid chains has a template function.

36. A further aspect of the invention relates to a method according to aspect 28, wherein the modification is accomplished by chemical coupling and the coupling of the nuc-macromolecules to the nucleic acid chain is accomplished via phosphoroamidite-coupling.

37. A further aspect of the invention relates to a method according to aspects 28 to 36, wherein nuc-macromolecules which allow for the coupling of only single nuc-component into the growing nucleic acid strand are used for the labeling process and multiple incorporations are prevented by modifications of the nuc-component and/or the linker component and/or the marker component.

38. A further aspect of the invention relates to a method according to aspect 37, wherein the multiple coupling is prevented reversibly.

39. A further aspect of the invention relates to a method according to aspect 37, wherein the multiple coupling is prevented irreversibly.

40. A further aspect of the invention relates to a method according to aspects 28 to 36, wherein nuc-macromolecules which allow for the coupling of multiple nuc-components into the growing nucleic acid strand are used for the labeling process.

41. A further aspect of the invention relates to a method according to aspects 28 to 40, wherein the nucleic acid chains participating in the reaction are coupled to a solid phase and have addressable positions.

42. A further aspect of the invention relates to a method according to aspect 41, wherein the nucleic acid chains compose a uniform population.

43. A further aspect of the invention relates to a method according to aspect 41, wherein the nucleic acid chains compose two or more different populations and each of the populations has an addressable position on the solid phase.

44. A further aspect of the invention relates to a method according to aspects 41, 42, wherein the coupling of nuc-macromolecules is conducted on the uniform population of nucleic acid molecules attached to the solid phase and the marker component of the nuc-macromolecule remains on the extended nucleic acid strand after the coupling and is not cleaved off.

45. A further aspect of the invention relates to a method according to aspects 41, 42, wherein the coupling of the nuc-macromolecules is conducted on the uniform population of nucleic acid chains attached to the solid phase and the marker component or its individual parts are cleaved off, with or without the linker component of the nuc-macromolecule, from the nuc-component incorporated into the growing nucleic acid strand, the cleaving-off taking place during or after the coupling.

46. A further aspect of the invention relates to a method according to aspects 41, 43, wherein the coupling of nuc-macromolecules in a reaction mixture is conducted simultaneously on two or more different populations of nucleic acid chains attached to the solid phase, wherein each of these populations has distinct addressable positions on the solid phase, and the marker component of the nuc-macromolecule remains on the extended nucleic acid strand after the coupling and is not cleaved off.

47. A further aspect of the invention relates to a method according to the aspects 41, 43, wherein the coupling of nuc-macromolecules is conducted simultaneously on two or more different populations of nucleic acid chains attached to the solid phase, wherein each of these populations has distinct addressable positions on the solid phase, and the marker component or its individual parts are cleaved off, with or without linker component of the nuc-macromolecule, from the nuc-component, the cleaving-off taking place during or after the coupling.

48. A further aspect of the invention relates to a method according to aspects 41 to 47, wherein the addressable positions having nucleic acid molecules on the solid phase are distributed as spots on a plane surface, and nucleic acid molecules are uniform on each spot.

49. A further aspect of the invention relates to a method according to the aspects 41 to 47, wherein the addressable positions having nucleic acid molecules are fastened on the beads or particles and nucleic acid molecules are uniform for each bead.

50. A further aspect of the invention relates to a method according to aspects 41 to 47, wherein the addressable positions having nucleic acid molecules are distributed in a multivessel array, like a microtiter plate or nanotiter plate or picotiter plate, wherein the nucleic acid molecules are uniform in one vessel of the multivessel array.

51. A further aspect of the invention relates to a method according to the aspects 28 to 35 and 37 to 50, which comprises the following steps:
   a) Providing of at least one population of single-stranded nucleic acid chains (NAC),
   b) Hybridizing primers to these nucleic acid chains, whereas extendable NAC primer complexes are formed,
   c) Incubation of at least one type of the nuc-macromolecule according to aspects 1 to 25 together with a type of polymerase according to aspect 31 with provided NAC primer complexes in steps (a) and (b) under conditions which allow for incorporation of complementary nuc-macromolecules, and each kind of the nuc-macromolecule having a distinctive label,
   d) Removal of the unincorporated nuc-macromolecules from the NAC primer complexes,
   e) Detection of the signals from the nuc-macromolecules which are incorporated in the NAC primer complexes,
   f) Removal of the linker component and the marker component from the nuc-macromolecules which are incorporated in the NAC primer complexes,
   g) Wash the NAC primer complexes,
if necessary, repetition of the steps (c) to (g).

52. A further aspect of the invention relates to a method according to the aspects 28-40, wherein the nucleic acid chains are coupled to a solid phase in a random arrangement.

53. A further aspect of the invention relates to a method according to aspects 28 to 41, 52 for the parallel sequence analysis of nucleic acid sequences (nucleic acid chains, NACs), in which
fragments (NACFs) of single-stranded NACs with a length of approximately 50 to 1000 nucleotides that may represent overlapping partial sequences of the whole sequence are produced,
the NACFs are bonded to a reaction surface in a random arrangement using a uniform or several different primers in the form of NACF primer complexes, wherein the density of NACF primer complexes bonded to the surface allows for an optical detection of signals from single incorporated nuc-macromolecules,
a cyclical synthesis reaction of the complementary strand of the NACFs is performed using one or more polymerases by
   a) adding, to the NACF primer complexes bonded to the surface, a solution containing one or more polymerases and one to four nuc-macromolecules that have a marker component labeled with fluorescent dyes, wherein the fluorescent dyes, which each are located on the marker component when at least two nuc-macromolecules are used simultaneously, are chosen in such a manner that the nuc-macromolecules used can be distinguished from one another by measurement of different fluorescent signals, the nuc-macromolecules being structurally modified in such a manner that the polymerase is not capable of incorporating another nuc-macromolecule in the same strand after such a nuc-macromolecule has been incorporated in a growing complementary strand, the linker component and marker component being cleavable,
   b) incubating the stationary phase obtained in step a) under conditions suitable for extending the complementary strands, the complementary strands each being extended by one nuc-macromolecule,
   c) washing the stationary phase obtained in step b) under conditions suitable for removing nuc-macromolecules that are not incorporated in a complementary strand,
   d) detecting the single nuc-macromolecules incorporated in complementary strands by measuring the characteristic signal of the respective fluorescent dye, the relative position of the individual fluorescent signals on the reaction surface being determined at the same time,
   e) cleaving-off the linker component and marker component of the nuc-components added to the complementary strand in order to produce unlabeled (nucleotides or) NACFs,
   f) washing the stationary phase obtained in step e) under conditions suitable for the removal of the marker component,
repeating steps a) to f), several times if necessary,
the relative position of individual NACF primer complexes on the reaction surface and the sequence of these NACFs being determined by specific assignment of the fluorescent signals, which were detected in the respective positions in step d) during successive cycles, to the nuc-macromolecules.

54. A further aspect of the invention relates to a method according to aspect 53, characterized in that steps a) to f) of the cyclical synthesis reaction are repeated several times, only one type of nuc-macromolecule being used in each cycle.

55. A further aspect of the invention relates to a method according to aspect 53 characterized in that steps a) to f) of the cyclical synthesis reaction are repeated several times, two types of differently labeled nuc-macromolecules being used in each cycle.
56. A further aspect of the invention relates to a method according to aspect 53 characterized in that steps a) to f) of the cyclical synthesis reaction are repeated several times, four types of differently labeled nuc-macromolecules being used in each cycle.
57. A further aspect of the invention relates to a method according to aspect 53 characterized in that the NACs are variants of a known reference sequence and steps a) to f) of the cyclical synthesis reaction are repeated several times, two differently labeled types of nuc-macromolecules and two unlabeled nucleotides being used alternately in the cycles and the whole sequences being determined by comparison with the reference sequence.
58. A further aspect of the invention relates to a method according to aspects 53 to 57 characterized in that a primer binding site (PBS) is introduced in each of the NACFs, one PBS being introduced at both complementary single strands in the case of double-stranded NACs and the primer binding sites displaying identical or different sequences for all NACFs.
59. A further aspect of the invention relates to a method according to aspects 53 to 57 characterized in that the NACFs are brought into contact with primers in a solution under conditions suitable for the hybridization of the primers to the primer binding sites (PBSs) of the NACFs, the primers exhibiting identical or different sequences to one another, and the NACF primer complexes formed then being bonded to the reaction surface.
60. A further aspect of the invention relates to a method according to aspects 53 to 57 characterized in that the NACFs are first of all immobilized on the reaction surface and only then brought into contact with primers under conditions suitable for the hybridization of the primers to the primer binding sites (PBSs) of the NACFs, NACF primer complexes being formed, the primers exhibiting identical or different sequences to one another.
61. A further aspect of the invention relates to a method according to aspects 53 to 60, wherein the incorporation reaction is being performed simultaneously on 10 to 100,000 different sequence populations.
62. A further aspect of the invention relates to a method according to aspects 53 to 60, wherein the incorporation reaction is being performed simultaneously on 100,000 to 100,000,000 different sequence populations.
63. A further aspect of the invention relates to a method according to aspects 28 to 62, wherein sequences of the nucleic acid chains are determined.
64. A further aspect of the invention relates to a method according aspects 28 to 63, wherein the marker component is fluorescently labeled.
65. A further aspect of the invention relates to a method according aspects 41 to 64, wherein the solid phase is independently selected from the following group: silicone, glass, ceramics, plastics, gels or their modifications.
66. In a further aspect of the invention, macromolecular compounds according to aspect 1 are especially preferred, wherein the nuc-component comprises the following structures, FIG. 3A.

Wherein:
Base is selected independently from the group of adenine, or 7-deazaadenine, or guanine, or 7-deazaguanine, or thymine, or cytosine, or uracil, or their modifications, wherein L is the linkage between the nuc-component and the linker component (coupling unit L) and X is the coupling position of the coupling unit L to the base, wherein the coupling position on pyrimidine bases is located in the 5-position and 4-position on the pyrimidine ring and in the 7-position on deazapurines.
$R_2$—is selected independently from the group of H, OH, or protected OH group
$R_3$—is selected independently from the group of H, OH, $NH_2$
$R_4$—is H or OH
$R_5$—is selected independently from the group of OH, or a protected OH group, or a monophosphate group, or a diphosphate group, or a triphosphate group
67. A further aspect of the invention relates to macromolecular compounds according to aspect 66, wherein the coupling unit (L) comprises the following structural elements:
$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—(CH$_2$)$_n$—$R_7$, $R_6$—(CH$_2$)$_n$—$R_7$, $R_6$-A-(CH$_2$)$_n$—$R_7$, $R_6$—(CH$_2$)$_n$—B—$R_7$, $R_6$—(CH=CH—)$_n$—$R_7$, $R_6$-(A-CH=CH—)$_n$—$R_7$, $R_6$—(CH=CH—B—)$_n$—$R_7$, $R_6$-A-CH=CH—(CH$_2$—)$_n$—$R_7$, $R_6$—(—CH=CH—CH$_2$)$_n$—B—$R_7$, $R_6$—(C≡C—)$_n$—$R_7$, $R_6$-(A-C≡C—)$_n$—$R_7$, $R_6$—(C≡C—B—)$_n$—$R_7$, $R_6$-A-C≡C—(CH$_2$—)$_n$—$R_7$, $R_6$—(—C≡C—CH$_2$)$_n$—B—$R_7$,
wherein $R_6$ is the nuc-component, $R_7$ is the rest of the linker, and A and B comprise the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, wherein (n) ranges from 1 to 5, a photolabile group
68. A further aspect of the invention relates to macromolecular compounds according to aspect 66, wherein the linker-component comprises a water-soluble polymer.
69. A further aspect of the invention relates to macromolecular compounds according to aspect 68, wherein the linker-component comprises water-soluble polymers selected independently from the following group: polyethylene glycol (PEG), polysaccharides, dextran, polyamides, polypeptides, polyphosphates, polyacetates, polyalkyleneglycoles, copolymers from ethyleneglycol and propyleneglycol, polyolefinic alcohols, polyvinylpyrrolidones, poly(hydroxyalkylmethacrylamides), polyhydroxyalkylmethacrylates, poly(x-hydroxy) acids, polyacrylic acid, polyacrylamide, polyvinylalcohol.
70. A further aspect of the invention relates to macromolecular compounds according to aspects 66 to 69, wherein the average length of a linker component ranges between 50 to 100, 100 to 200, 200 to 500, 500 to 1000, 1000 to 2000, 2000 to 10000, 10000 to 100000 atoms.
71. A further aspect of the invention relates to macromolecular compounds according to aspects 66 to 69, wherein a marker component has one of the following functions: signal-giving function, signal-transmitting function, catalytic function or affine function.

72. A further aspect of the invention relates to macromolecular compounds according to aspects 66 to 69, wherein a marker component consists of one structural marker unit.
73. A further aspect of the invention relates to macromolecular compounds according to aspects 66 to 69, wherein a marker component consists of several structural marker units bonded to a core component.
74. A further aspect of the invention relates to macromolecular compounds according to aspects 72 or 73, wherein a structural marker unit independently comprises one of the following structural elements: biotin, hapten, radioactive isotope, rare-earth atom, dye, fluorescent dye.
75. A further aspect of the invention relates to macromolecular compounds according to aspects 72 or 73, wherein a structural marker unit independently comprises one of the following elements:
nanocrystals or their modifications, proteins or their modifications, nucleic acids or their modifications, particles or their modifications.
76. A further aspect of the invention relates to macromolecular compounds according to aspect 75, wherein a structural marker unit comprises one of the following proteins:
enzymes or their conjugates or modifications,
antibodies or their conjugates or modifications,
streptavidin or its conjugates or modifications,
avidin or its conjugates or modifications
77. A further aspect of the invention relates to macromolecular compounds according to aspect 75, wherein a structural marker unit comprises one of the following types of nucleic acid chains: DNA, RNA, PNA, wherein the length of nucleic acid chains ranges between 10 and 10,000 nucleotides.
78. A further aspect of the invention relates to macromolecular compounds according to aspects 73 to 77, wherein the core component of the marker component independently comprises one of the following elements: water-soluble Polymer from the group of: polyamides (e.g. polypeptides), polyacrylic acid and its derivates, polyacrylamides and their derivates, polyvinylalcohols and their derivates, nucleic acids and their derivates, streptavidin or avidin and their derivates, dendrimeres, whereas these elements can be linear or branched or crosslinked with each other.
79. A further aspect of the invention relates to macromolecular compounds according to aspects 66 to 71, 73 to 78, wherein the linkage between several structural marker units and the core component is covalent or affine.
80. A further aspect of the invention relates to macromolecular compounds according to aspects 66 to 73, wherein the linkage between a structural marker unit and the linker is covalent or affine.
81. A further aspect of the invention relates to macromolecular compounds according to aspects 66 to 71, 73 to 78, wherein the linkage between the core component and the linker is covalent or affine.
82. A further aspect of the invention relates to macromolecular compounds according to aspects 66 to 81, wherein only one nuc-component with one linker component is linked to the marker component,
83. A further aspect of the invention relates to macromolecular compounds according to aspects 66 to 82, wherein only one nuc-component with one linker component is linked to the marker component, wherein the linker component comprises one or several compounds that are cleavable under mild conditions.
84. A further aspect of the invention relates to macromolecular compounds according to aspects 66 to 82, wherein only one nuc-component with one linker component is linked to the marker component, wherein one or several parts of the nuc-macromolecule are modified in such a way, that only one nuc-component can be incorporated into the growing strand.
85. A further aspect of the invention relates to macromolecular compounds according to aspects 66 to 71, 73 to 82, wherein several nuc-components are each coupled to one marker component via a linker.
86. A further aspect of the invention relates to macromolecular compounds according to aspects 66 to 71, 73 to 82, wherein several nuc-components are each coupled to one marker component via a linker, wherein each respective linker component comprises one or several compounds that are cleavable under mild conditions.
87. A further aspect of the invention relates to macromolecular compounds according to aspects 66 to 71, 73 and 82, wherein several nuc-components are each coupled to one marker component via a linker, wherein one or several parts of the nuc-macromolecule are modified in such a way that only one nuc-component can be incorporated into the growing nucleic acid chain.
88. A further aspect of the invention relates to oligonucleotides or polynucleotides comprising at least one nuc-macromolecule according to aspects 66 to 87 per one nucleic acid chain.
89. A further aspect of the invention relates to oligonucleotides or polynucleotides according to aspect 88, wherein oligo- or polynucleotides are RNA or DNA or PNA and their length ranges between 5 and 50,000 nucleotides.

Comparison of the Properties of Conventionally Modified Nucleotides and Nuc-macromolecules.

Substrate Properties of Conventionally Modified Nucleotides

The influence of different lengths and chemical composition of the linker and different sizes and composition of the low molecular weight markers on the substrate properties of nucleotides (G. Wright et al. Pharmac. Ther. 1990, v. 47, p. 447, Klevan U.S. Pat. No. 4,828,979, Lee. et al. Nucleic Acid Research 1992, v. 20, p. 2471, 3. Brandis Nucleic Acid Research, 1999, v. 27, p. 1912) shows that even minor changes in the structure of the nucleotides or linker or marker may lead to big changes in the substrate properties of modified nucleotides.

It can be shown that the coupling of significantly larger molecules (e.g. proteins) to a conventionally modified nucleotide results in the loss of its substrate properties (example 34B).

For this reason, signal-amplifying macromolecules could be coupled into the nucleic acid chain only after the completed enzymatic incorporation of nucleotides, e.g. the binding of labeled streptavidin to biotinylated nucleotides.

A comparable situation can be observed for nucleotide monomers in a nucleic acid chain: only low molecular weight compounds should be coupled to an oligonucleotide near to the 3'-OH-position if this oligonucleotide is intended to be a primer in a subsequent enzymatic reaction. Too large a molecule, e.g. streptavidin, coupled to a nucleotide monomer at the 3'-end or in the vicinity of the 3'-end of an oligonucleotide results in a loss of primer properties. Without committing themselves to any particular theory, the inventors explain this fact as the result of the sterical influence of macromolecules. The spatial relations in the active center of a variety of enzymes are very challenging and the catalytic mechanism of many enzymes comprises complex conformational changes in the enzyme structure itself as well as the substrate structure (nucleotide monomers). In many cases, minor chemical modifications of nucleotide monomers result in a changed enzymatical acceptance of the nucleic acids. For example, an alpha-thiophosphonate modification of the nucleotide monomer results in resistance of the nucleic acid chain to exonuclease activity.

Even though there is widespread use of fluorescent dyes in current diagnostics and science, there is a demand for signal-amplifying technologies for biologically active labeled molecules. At present, secondary enzymatic signal amplification steps are often applied.

Despite the obvious consideration of the multiple labelling of nucleotides in the form of a macromolecular marker component, there is no evidence to suggest the possibility of a successful combination of conventional nucleotide structure and a macromolecular marker where the nucleotide preserves its substrate properties.

The mass of conventionally modified nucleotides is comparable to that of non-modified nucleotides and is relatively low if compared to that of proteins, e.g. streptavidin or polymerases. Increasing the mass of the nucleotide by the introduction of macromolecular compounds can result in a change in the physical and biochemical properties of the nucleotides.

Surprisingly, it was possible to overcome this limitation of current state of the art by the introduction of a substantially longer linker between the nuc-component and the marker component than had previously been known.

Surprisingly, the modified nucleotides here invented maintain their substrate activity despite the massive changes in their properties and can be used by enzymes as substrates. For example, polymerases can incorporate the invented modified nucleotides into the growing strands. Terminal deoxynucleotidyl transferase (TdT) can couple nuc-macromolecules to the 3-end of a nucleic acid chain (example 34B, 34C and example 35).

It should be obvious to the specialist that the mass of the nuc-macromolecules here invented is several times larger than that of natural nucleotides and has a great influence on the nuc-component.

Application Fields for Nuc-macromolecules

The coupling of a macromolecular marker to a substrate for enzymes, i.e. to a nucleotide, opens a broad range of applications for these nuc-macromolecules in different fields of biotechnology, medicine and lifescience.

According to this invention, nuc-macromolecules can be used in procedures where they serve as substrates for enzymes.

In one embodiment of the invention, nuc-macromolecules are used in procedures for the labelling of nucleic acids. The incorporation reaction of nuc-macromolecules proceeds according to general rules of the enzymatic primer-extension reaction of nucleic acids ("Molecular Cloning", J. Sambrook, 3. Ed. 2001).

One big benefit of a macromolecular marker coupled to an incorporated nucleotide is a substantially stronger signal compared to conventionally modified nucleotides.

A further benefit is the large distance between the marker and nucleic acid chain, owing to which only minor interactions between the marker and the nucleic acid chain are expected. For example, this has an influence on the fluorescent properties of the marker: the fluorescence of the marker is not quenched by nucleobases (purines and pyrimidines). If several nuc-macromolecules are incorporated into a single nucleic acid chain, the large distance between nuc-components and markers results in a substantial diminution of interactions between the markers of adjacent nucleotides.

In the case of enzymatic labelling of a nucleic acid chain with a nuc-macromolecule there may be no need for further steps of signal amplification. Many of the known signal amplification steps, e.g. biotin-streptavidin, digoxigenin-antibody I-antibody II, result in only medium yield, e.g. during signal amplification in FISH-analysis. Unsteady and low yields in labelling cause fluctuations and weakness of signals that may lead to false interpretation. The introduction of nuc-macromolecules may reduce or eliminate this weakness in labelling. The use of nuc-macromolecules with stable signal intensities may help to overcome signal fluctuations.

The labelling of nucleic acids can be used in different procedures. Particular conditions for the preparation of nucleic acids and the order of enzymatic and detection steps depend upon the individual procedure to which the labelling is applied.

Taken together, the nuc-macromolecules here invented represent an above average improvement in labelling strategies for nucleic acids.

Modified Nucleic Acid Chains

In one embodiment of the invention, nucleic acid chains comprise nuc-components of the nuc-macromolecules as units of the chain. The nuc-macromolecules are considered as monomers of a polymer chain, i.e. the nucleic acid chain. Such nucleic acid chains with integrated nuc-macromolecules can be used as probes and as a reaction partner in different areas (e.g. Real-Time-PCR, Ligase chain reaction).

In one embodiment, a nuc-macromolecule is integrated to the 5' end of the nucleic acid chain. In one embodiment, a nuc-macromolecule is integrated to the 3' end of the nucleic acid chain. In a further embodiment, a nuc-macromolecule is integrated inside of the nucleic acid chain and the distance to the nearest chain end lies within the following ranges (number of the monomers of the chain up to the next chain end): 1 to 2, 2 to 4, 4 to 8, 8 to 15, 15 to 30, 30 to 100, 100 to 500.

A nuc-macromolecule can comprise several nuc-components. In one embodiment, only one nuc-component of a nuc-macromolecule is integrated into a nucleic acid chain; the other nuc-components are in monomer form. In another embodiment, several nuc-components of a nuc-macromolecule are integrated in nucleic acid chains, whereby these nucleic acid chains can have identical or also different sequences.

The use of nucleic acid chains modified with nuc-macromolecules is especially advantageous if the nuc-macromolecule participates as part of a polymer chain in an enzymatic reaction or is in the immediate proximity of the nucleotide participating in the reaction. The influence of a macromolecular marker component on the enzyme is greatly reduced by the long linker of the nuc-macromolecules, so that the modified nucleotide components can take part in the enzymatic reactions (e.g. having primer function in a templatedependent, polymerase driven reaction, with a ligase-dependent reaction (e.g. ligase chain reaction), 3'-exonuclease or 5' exonuclease activities of different enzymes, endonuclease cleavage), i.e. they do not impair the reaction with neighboring nucleotides (J. Wilhelm "Entwicklung Real-Time-PCR-basierter Methoden für die moderne DNA-Analytik" Dissertation, 2003, Gießen, S. Meuer "Rapid cycle real time PCR", Springer 2004, ISBN 3-540-66736-9, T. Weissensteiner "PCR-Technology: current innovations" CRC Press 2004 ISBN 0-8493-1184-5). The distance between the position of the nuc-macromolecule in the nucleic acid chain and that of the nucleotide of the same nucleic acid chain which takes part as a substrate in an enzymatic reaction falls within, for instance, the following ranges (number of nucleotides): 0 to 3, 3 to 6, 6 to 10, 10 to 20, 20 to 40. The number 0 means that the nuc-macromolecule is coupled directly to the nucleotide taking part in the reaction.

Some examples of the use of Nuk-macromolecules are discussed below.

Processes in the Liquid Phase

In one embodiment of the labeling processes, the nucleic acid chains to be labeled are in the liquid phase, see examples 34, 35.

Many different processes, e.g. PCR and transcription ("Molecular Cloning", J. Sambrook, 3. Ed. In 2001), can be carried out with nuc-macromolecules according to the present invention. In these processes, nuc-macromolecules are added in the reaction in a similar way to nucleotides modified conventionally with a dye. General rules for the use of conventionally modified nucleotides, such as, for example, dCTP-Cy3 (Amersham Bioscience) or dUTP-TMR (NEN) are described in detail in the literature ("Molecular Cloning", J. Sambrook, 3. Ed. 2001).

For instance, one type of nuc-macromolecule, e.g. dATP or dCTP, can be used for the coupling of a single complementary nucleotide to the primer. However, mixtures of modified and unmodified nucleotides are used in most reactions (H. Yu et al. Nucleic Acid Research 1994, v. 22 p. 3226-, "Molecular Cloning", J. Sambrook, 3. Ed. 2001). For instance, labeled and unlabeled nucleotides can be mixed in the following ratios in the case of labeling with a nuc-macromolecule comprising dUTP:

dATP:dCTP:dGTP:dTTP:dUTP-nuc-macromolecule=1:1:1: 0.9:0.1 ordATP:dCTP:dGTP:dTTP:dUTP-nuc-macromolecule=1: 1:1:0.7:0.3 ordATP:dCTP:dGTP:dTTP:dUTP-nuc-macromolecule=1: 1:1:0.95:0.05 the precise mixture ratios can be optimized for individually selected reactions.

Furthermore, several types of nuc-macromolecule can be used in a reaction. For instance, nuc-macromolecules can carry different markers. In one embodiment, the markers of the nuc-macromolecules are selected in such a way that they form a FRET pair (Faner, R et al. *Hum Immunol* 2004, v. 65, p. 826-38, Lazowski, K. W. et al. *Antisense Nucleic Acid Drug Dev* 2000, v. 10, p. 97-103, Talayera, E. M. *Appl Spectrosc* 2003, v. 57, p. 208-15, Tsourkas, A. et al. *Anal Chem*, 2003, v. 75, p. 3697-703, Singh, K. K., et al. *Methods Mol Biol* 2004, v. 252, p. 33-48, Wang, L. *Spectrochim Acta A Mol Biomol Spectrosc*, 2004, v. 60, p. 2741-50).

After the incorporation of such nuc-macromolecules in the growing nucleic acid chain the average distance between the fluorophores decreases, so that FRET occurs between the donors and the acceptor. Since nuc-macromolecules carry a much stronger marker than conventionally modified nucleotides, the signal intensity of the FRET signal can be greater. The precise condition of the reaction can be optimized by means of the choice of fluorophore, its coupling to the nuc-macromolecule, the concentration of nuc-macromolecules and the ratio between the nuc-macromolecules and unlabeled nucleotides. As a general rule, the average distance between the fluorophores of a FRET pair should be no greater than 10 nm.

Solid Phase Processes

In a further embodiment of the labeling processes, the nucleic acid chains to be labeled or their complementary stands are attached to a solid phase. Many processes for the labeling of immobilized nucleic acid chains with conventionally modified nucleotides are known (Suomalainen A et al. Methods Mol. Biol. 2003, Pirrung M C et al. Bioorg Med Chem Lett. 2001 Sep. 17; v. 11(18): p. 2437-40). Microparticles are examples of the solid phase (Spherotech Inc, Streptavidin-polystyre Particle, 2.17μ). An incorporation reaction on solid phase with nuc-macromolecules is described in example 34C. Another example of solid phase are planar surfaces to which nucleic acids are bound.

Nuc-macromolecules are suitable for analysis processes with an incorporation reaction with nucleic acid coupled to a solid phase; nuc-macromolecules can be used similarly to conventionally modified nucleotides in many processes, such as, for example, minisequencing (Suomalainen A et al. Methods Mol Biol. 2003; 226:361-6. Liljedahl U et al. Pharmacogenetics. 2003 January; v. 13(1): p. 7-17, Olsson C et al. Methods Mol Biol. 2003; v. 212: p. 167-76), primer extension (Pirrung M C et al. Bioorg Med Chem Lett. 2001 Sep. 17; v. 11(18): p. 2437-40, Cai H, et al. Genomics. 2000 Jun. 1; v. 66(2): p. 135-43, Kurg A et al. Genet Test. 2000; v. 4(1): p. 1-7, Pastinen T et al. Genome Res. 1997 June; 7(6):606-14). U.S. Pat. No. 6,287,766, U.S. Patent No. 2003148284, U.S. Patent No. 2003082613, EP 1256632, WO0194639, WO 2004/076692, Ju et al. U.S. Pat. No. 6,664,079. solid phase PCR (WO 9626291, WO 9409156, U.S. Pat. No. 6,221,635), Sequenzierung durch die Synthese (Ju et al U.S. Pat. No. 6,664,079), single-molecular-sequencing (Tcherkassov WO 02088382, Seeger WO 0018956, Kartalov WO 02072892). In many cases, a synthesis of the complementary chain with the attached primer template complexes occurs.

Signal amplification steps are often required for analysis processes with immobilized nucleic acid chains. In such processes nuc-macromolecules can bring an especial advantage, because signal intensity is superior. The number of signal-giving marker units of nuc-macromolecules can be determined during the synthesis, so that the signal intensity from incorporated nuc-macromolecules can be quantified.

In such processes nuc-macromolecules having fluorescent signals, radioactive signals or enzymes as marker units can be used. Nuc-macromolecules with fluorescent signals are especially advantageous for such processes, because fluorescence enables high sensitivity.

In one embodiment of such processes, fluorescent signals from the markers of incorporated nuc-macromolecules are detected. The nuc-macromolecules used can form a FRET pair. In a further embodiment, labeled primer can be used for the labeling of nucleic acids attached to a solid phase, whereby these primers comprise, in one embodiment, one or several nuc-macromolecules and, in a further embodiment, these primers comprise conventional labelling. In both these embodiments, the labeling within the primer can form one part of a FRET pair. The part of a FRET pair coupled within the primer can act as a donor as well as an acceptor in the detection process. The incorporated nuc-macromolecules with an appropriate partner for the FRET pair can comprise either a removable or a non-removable marker.

A significant increase in the signal specificity can be achieved by the use of FRET between the incorporated nuc-macromolecules and the label attached to the primer. Thereby, detection can occur during the incorporation process or, in another embodiment, as a separate step in the process.

In one embodiment, nuc-macromolecules with a specific type of nuc-component (for instance, dTTP) carry, preferably, a marker component distinctive for each nuc-macromolecule, so that, for instance, four types of nuc-macromolecule (corresponding to dTTP, dCTP, dATP and dGTP) can be used at the same time and can be distinguished. Other labeling schemes are known, e.g. Tcherkassov WO 02088382.

Depending on the particular process, unlabeled nucleotides, e.g. naturally occurring nucleotides, are added to the reaction solution together with nuc-macromolecules.

In one embodiment of the labeling process, nuc-macromolecules which permit the incorporation of only a single nuc-component into the growing nucleic acid strand are used, whereby multiple incorporations are prevented by modifications of the nuc-component, and/or of the linker component and/or of the marker component. The continuation of incorporation can be prevented in either a reversible or an irreversible mode. An irreversible stop can be achieved, for instance, by the incorporation of nuc-macromolecules which comprise a dideoxinucleoside triphosphate as a nuc-component. A reversible stop can be unmade in a subsequent step of the process, so that the incorporation reaction can continue. Examples of a reversible blockade of the reaction are described (Metzker-et al. Nucleic acid Research 1994, v. 22, p. 4259, Canard et al. Gene, 1994, v. 148, p. 1, Kwiatkowski U.S. Pat. No. 6,255,475, Kwiatkowski WO 0125247, Parce WO 0050642, Tcherkassov WO 02088382, Ju et al. U.S. Pat. No. 6,664,079, Milton et al. WO 2004018497, Milton et al. WO 2004018493, Balasubramanian et al. WO 03048387)

In another embodiment, the incorporated nuc-macromolecules do not prevent the ongoing incorporation of further nucleotides. If a mixture of modified and unmodified nucleotides is used, several nuc-macromolecules can be incorporated after the incorporation of an initial nuc-macromolecule into the growing strand.

The solid phase can be, for instance, a planar surface or beads or a kind of array of several vessels (e.g. microtiter plate or nanotiter plate). The nucleic acids can be coupled by a variety of methods to the solid phase (McGall et al. U.S. Pat. No. 5,412,087, Nikiforov et al. U.S. Pat. No. 5,610,287, Barrett et al. U.S. Pat. No. 5,482,867, Mirzabekov et al. U.S. Pat. No. 5,981,734, "Microarray biochip technology" 2000 M. Schena Eaton Publishing, "DNA Microarrays" 1999 M. Schena Oxford University Press, Rasmussen et al. Analytical Biochemistry v. 198, S. 138, Allemand et al. Biophysical Journal 1997, v. 73, p. 2064, Trabesinger et al. Analytical Chemistry 1999, v. 71, p. 279, Osborne et al. Analytical Chemistry 2000, v. 72, p. 3678, Timofeev et al. Nucleic Acid Research (NAR) 1996, v. 24 p. 3142, Ghosh et al. NAR 1987 v. 15 p. 5353, Gingeras et al. NAR 1987 v. 15 p. 5373, Maskos et al. NAR 1992 v. 20 p. 1679). There are known procedures for the amplification of nucleic acid chains starting with single molecules. Such procedures can be used for creation of a population of nucleic acid chains with identical sequence, which have addressable positions on the solid phase, whereby the solid phase can be a planar surface or beads. Preferably, such nucleic acids are hybridized with a primer to form primer template complexes, so that an enzymatic synthesis of complementary strands can proceed ("Molecular Cloning", Maniatis, 3. Ed. In 2001).

Primerextension:

In one embodiment of the process, the incorporation reaction of nuc-macromolecules occurs in one single population of uniform nucleic acid molecules attached onto the solid phase, whereby the marker component of the nuc-macromolecule remains bound to the extended primer after incorporation and is not removed.

Essentially, such processes comprise the following steps:
1) Preparation of a solid phase with attached primer template complexes.
2) Incubation of the prepared solid phase with a reaction solution, which comprises one or several types of polymerase and one or several types of nuc-macromolecule, whereby each nuc-macromolecule can be unambiguously identified by its marker.
3) Removal of the reaction solution and washing of the solid phase.
4) Detection of the signals of the incorporated nuc-macromolecules and identification of each type of incorporated nuc-macromolecule by means of its signal properties.

Sequencing:

In another embodiment of the process, the incorporation reaction of nuc-macromolecules occurs in a single population of uniform nucleic acid molecules attached to the solid phase, whereby the marker component or its single compounds with or without a linker component of the nuc-macromolecule is separated from the nuc-component during or after the incorporation reaction.

Essentially, such processes comprise the following steps:
1) Preparation of a solid phase with attached primer template complexes.
2) Incubation of the prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule according to its signal properties.
5) Removal of the marker component from the incorporated nuc-macromolecules.
6) Repetition of steps 2 to 5.

The repetition can be carried out, for instance, 1 to 2, 2 to 5, 5 to 10, 10 to 20, 20 to 30 times.

In another embodiment of the process, the incorporation of nuc-macromolecules occurs in an enzymatic reaction in parallel on two or several different populations of uniform nucleic acid populations attached onto a solid phase, whereby the said populations have addressable positions on the solid phase and the marker component of the nuc-macromolecule remains bound to the extended primer after incorporation and is not cleaved away.

These addressable positions can take the form of spots, for instance, in the case of a planar surface. When beads are used as a solid phase, different populations of nucleic acids are attached to different beads. When arrays of vessels (e.g. microtiter plate or nanotiter plate) are used, each individual nucleic acid population is fixed in an individual vessel separately.

Essentially, such processes comprise the following steps:
1) Preparation of a solid phase with attached primer template complexes.
2) Incubation of the said prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule by means of its signal properties.

In another embodiment of the sequencing process, the incorporation of nuc-macromolecules occurs in an enzymatic reaction in parallel on two or several different populations of uniform nucleic acid molecules attached onto a solid phase, whereby the said populations have addressable positions on the solid phase. The uniform nucleic acid populations can be attached to a surface by various means (see above). In a special embodiment of the processes, the marker component or its individual constituents is/are separated from the incorporated nuc-macromolecule (with or without a linker component of the nuc-macromolecule) during or after the incorporation reaction. Nuc-macromolecules with a cleavable bond in the linker are suitable for such processes. In the case of planar surfaces, the addressable positions can take, for instance, the form of spots. When beads are used as a solid phase, different populations of nucleic acids are fixed on different beads. When arrays with multiple vessels are used, individual nucleic acid populations are fixed in individual vessels separately.

Essentially, such processes comprise the following steps:
1) Preparation of a solid phase with attached primer template complexes.
2) Incubation of the prepared solid phase with a reaction solution which comprises one or several types of polymerase and one or several types of nuc-macromolecule, whereby the nuc-macromolecules can be unambiguously identified by their markers.
3) Removal of the reaction solution and washing of the solid phase.
4) Detection of the signals from incorporated nuc-macromolecules and the identification of each type of incorporated nuc-macromolecule according to its signal properties.
5) Removal of the marker component from the incorporated nuc-macromolecules.
6) Repetition of steps 2 to 5.

The repetition can be carried out, for instance, 1 to 2, 2 to 5, 5 to 10, 10 to 20, 20 to 30, 30 to 50, 50 to 100, 100 to 200 times.

In one embodiment of the said process, in step (2), nuc-macromolecules are used together with other modified nucleotides. Thereby, the synthesis of the complementary strand takes place gradually: complementary strands are extended at most by one nucleotide per one synthesis step. Control of the enzymatic reaction is achieved through reversible terminators. Preferably, terminators are with modifications on 3' OH group and no additional modifications on the base are used. After the cleavage of the modification from the incorporated nucleotide, further synthesis can proceed on these strands. The structure of the nuc-macromolecules used in this embodiment can vary. Preferably, these will be nuc-macromolecules with terminating properties, i.e. after their incorporation, no additional nucleotide can be incorporated by a polymerase. Preferably, the linker is coupled to the base of the nuc-component and comprises a cleavable bond. The mixing of nuc-macromolecules with terminating properties and reversible terminators allows for differentiation between labeling and reversible termination within a single population of nucleic acid chains. Because the nuc-macromolecules have a terminating action in this embodiment of the process, a smaller number of nucleic acid chains is available in every further step of the sequencing reaction. In order to proceed with the incorporation reaction, a part of the strands has to be blocked reversibly. The fraction of nucleic acid chains modified with nuc-macromolecules can be very small, because the signal power of the nuc-macromolecules can be substantial. The ratio between the nuc-macromolecules and reversible terminators in a reaction step can fall, for instance, within the following ranges: 100:1 and 1:10, 10:1 and 1:1, 1:1 and 1:10, 1:10 and 1:100, 1:100 and 1:1000 (concentration of nuc-macromolecules: concentration of reversible terminators). This ratio can remain steady during the whole sequencing reaction or vary. Since polymerases can accept the nuc-macromolecules and the reversible terminators differently, several kinds of polymerases can be used during the incorporation step. The removal of the signals after detection leads to a better signal to noise ratio during subsequent rounds of detection and is typical of the processes of sequencing by synthesis. The removal of reversible termination can be carried out in a separate step of the process or can be combined, for instance, with the removal of the labeling.

The advantage of using nuc-macromolecules is that the labeling of a small portion of the whole population is sufficient for the detection of the incorporation event. This allows the sequencing reaction to be conducted with smaller quantities of starting material. The use of reversible terminators with a protective group on 3' positions and a base without modification leads to the result that, after the removal of the blocking protective group, the nucleotide remaining in the nucleic acid chain carries no further modifications and therefore can be accepted well by polymerases as a natural substrate.

In a further embodiment of the process, the following steps are carried out:
  a) Preparation of at least of one population of single-stranded nucleic acid chains.
  b) Hybridisation of sequence-specific primers to the said prepared nucleic acid chains, which results in the formation of nucleic acid chain primer complexes (i.e. NAC primer complexes) capable of extension.
  c) Incubation of at least one type of nuc-macromolecule, in accordance with aspects 1 to 25, together with one type of polymerase, in accordance with aspect 31, with NAC primer complexes, prepared in steps (a) and (b), under such conditions as allow for the incorporation of complementary nuc-macromolecules, whereby each type of nuc-macromolecule has characteristic labeling.
  d) Removal of the non-incorporated nuc-macromolecules from the NAC Primer complexes.
  e) Detection of the signals from the nuc-macromolecules incorporated into the NAC Primer complexes.
  f) Removal of the linker component and the marker component from the nuc-macromolecules incorporated into the NAC Primer complexes.
  g) Washing the NAC Primer complexes.
  If necessary, repetition of steps (c) to (g).

In a further embodiment of the processes, the incorporation reaction of nuc-macromolecules occurs simultaneously on a population of different nucleic acid molecules attached to a solid phase, whereby the said nucleic acid molecules are attached to the solid phase in a random arrangement (Tcherkassov WO 02088382). In this process, sequences are determined for individual nucleic acid chain molecules. The primer nucleic acid complexes taking part in the enzymatic reaction are attached in such a density as allows for the detection of signals from single nuc-macromolecules coupled to a single nucleic acid molecule, but the density of the attached primer or nucleic acid can be substantially higher. For instance, the density of the primer nucleic acid complexes taking part in the incorporation reaction ranges from 1 complex per $10\,\mu m^2$ to 1 complex per $100\,\mu m^2$, from 1 complex on $100\,\mu m^2$ to 1 complex per $1000\,\mu m^2$, from 1 complex per $1000\,\mu m^2$ to 1 complex on $10{,}000\,\mu m^2$.

Examples of the attachment of nucleic acids to the solid phase in such a density as allows for analyses on single molecules are shown in WO0157248, U.S. Patent No. 2003064398, U.S. Patent No. 2003013101 and WO 02088382. Suitable equipment for detection is described in WO 03031947.

The number of single nucleic acid molecules to be analyzed ranges, for instance, between 1000 and 100,000, 10,000 to 1,000,000, 100,000 to 10,000,000 molecules. The marker component or its individual constituents with or without a linker component of the nuc-macromolecule are cleaved from the nuc-component during or after the incorporation reaction.

The said method for the parallel sequence analysis of nucleic acid sequences (nucleic acid chains, NAC) comprises the following steps, in which:

Fragments (NACFs) of single-strand NACs with a length of approximately 50-1000 nucleotides are produced that may represent overlapping partial sequences of a whole sequence.

The NACFs are bound in a random arrangement using one uniform or several different primers in the form of NACF primer complexes on a reaction surface, whereby the density of NACF primer complexes bound to the surface allows for optical detection of signals from individual incorporated nuc-macromolecules.

A cyclical synthesis reaction of the complementary strand of the NACFs is performed using one or more polymerases by:
- a) adding to the NACF primer complexes bound to the surface a solution comprising one or more polymerases and one to four nuc-macromolecules that have a marker component labeled with fluorescent dyes, with concomitant use of at least two nuc-macromolecules with dyes coupled to the marker component, being chosen in such a way that the nuc-macromolecules used can be distinguished from one another by the measurement of different fluorescent signals, with the nuc-macromolecules being structurally modified in such a way that the polymerase, following incorporation of such a nuc-macromolecule in a growing complementary strand, is not capable of incorporating a further nuc-macromolecule in the same strand, with the linker component and marker component being cleavable,
- b) incubating the stationary phase obtained in step a) under conditions suitable for extending the complementary strands, with the complementary strands being extended in each case by one nuc-macromolecule,
- c) washing the stationary phase obtained in step b) under conditions suitable for the removal of nuc-macromolecules not incorporated in a complementary strand,
- d) detecting the single nuc-macromolecules incorporated in complementary strands by measuring the signal characteristic of the respective fluorescent dye, with the relative position of the individual fluorescent signals on the reaction surface being determined at the same time,
- e) cleaving off the linker component and marker component of the nuc-components added to the complementary strand in order to produce unlabeled (NTs or) NACFs,
- f) washing the stationary phase obtained in step e) under conditions suitable for the removal of the marker component, repeating steps a) to f), where appropriate several times, with the relative position of individual NACF primer complexes on the reaction surface and the sequence of these NACFs being determined by specific assignment of the fluorescent signals detected in step d) in successive cycles in the respective positions to the nuc-macromolecules.

Application of Nucleic Acid Chains Comprising Nuc-macromolecules.

Surprisingly, after the incorporation of a nuc-macromolecule to the 3' end of the nucleic acid, these modified nucleic acid chains, for their part, retain the ability to couple further nucleotides to the 3'-hydroxyl group by means of polymerases (see example 34C). This means that not only is the nuc-component in the nuc-macromolecules able to remain available, but also the nucleic acid chains modified with those nuc-macromolecules are available for the enzymes, and can find applications in different areas of biotechnology. Not only nucleic acid chains modified on 3' ends with nuc-macromolecules, but also nucleic acid chains which comprise one or several nuc-macromolecules as monomers at 5' ends or in the internal positions of the nucleic acid polymer, retain their substrate properties for polymerases, exonucleases and ligases. Examples of the applications of oligonucleotides modified with nuc-macromolecules are known to experts in this field, e.g. primer extension reactions, real time PCR or ligase reactions.

Choice of Enzymes

As monomers, nucleotides play a central rôle in different metabolic processes, for instance, in the storage and transmission of genetic information in the cell ("Genes V" B. Lewin, 1994). Nucleotides are also known as an energy source in the cell (ATP, UTP), or as messengers (GTP) in intracellular signal mediation ("Biochemie und Pathobiochemie", G. Löffler, 2003). For these reasons, nucleotides and their analogues are used as therapeutics and diagnostic tools. Nucleotide monomers, coupled to nucleic acid polymers (nucleic acid chains), form the basis for information storage in living organisms.

Nuc-macromolecules have the potential to find applications in different areas of biotechnology.

The possibility of coupling nucleotides to a macromolecule while retaining the substrate properties of the nucleotides also opens many avenues for the specific addressing of the modified nucleotides within an organism or a cell, so that nuc-macromolecules display a new basic model for nucleotide-prodrugs.

Various types of polymerase, for instance, can be used as enzymes ("DNA Replication", Kornberg, 2. Ed. 1992), in particular, DNA-dependent DNA polymerases, RNA-dependent DNA polymerases, DNA-dependent RNA polymerases and RNA-dependent RNA polymerases. Thermostable as well as thermolabile polymerases can be used, as for example Klenow polymerase or Taq polymerase. The specialist will be able to find other examples of suitable polymerases in the literature cited here. Transferases constitute another example of enzymes, e.g. deoxynucleotidyl transferase ("Molecular Cloning", Maniatis, 3. Ed. 2001). Also other enzymes and proteins (for instance, kinases, membrane receptors) that accept nucleotides as substrates, an energy source, co-factors or as messenger substances, can be used.

Enzymes differ in their ability to accept modified nucleotides as substrates. It will be obvious to the specialist that different functional tests must be used to examine and to apply certain properties of nucleotides. Examples of different test procedures for the labeling of nucleic acids are shown in H. Held et al. Nucleic Acid Research 2002, v. 30, p. 3857, M. Metzger et al. Nucleic Acid Research 1994, v. 22, p. 4259, M. Herrlein et al. Helvetica Chimica Acta 1994, v. 77, p. 586, B. Canard et al. PNAS 1995, v. 92, p. 10859, Canard U.S. Pat. No. 5,798,210, J. Hovinen et al. J. Chem. Soc. Perkin 1994, 1994, 211 and also in other patents and publications cited here.

Accordingly, suitable combinations of polymerases and modified nucleotides can be selected for each respective purpose. Examples of the incorporation of nuc-macromolecules into the primer are shown in example 34. The examples shown do not aim at the restriction of the range of application of nuc-macromolecules, but are intended to display to the specialist the difference in properties of nuc-macromolecules as compared to conventional modified nucleotides.

Nuc-macromolecules or their intermediates can be also used in the conventional chemical synthesis of oligonucleotides, for instance, in a solid phase synthesis (Giegrich, "Neue photolabile Schutzgruppen für die lichtgesteuerte Oligonucleotidsynthese", 1997, Beier, "Neue Strategien zum Aufbau von RNA- und DNA-Oligonucleotiden", 1996), whereby the nuc-component of the nuc-macromolecules carries suitable modifications, making the said nuc-macromolecuies suitable for chemical coupling to the nucleic acid chain, as for example in Herrlein, "Synthese von modifizierten Nukleosiden, Nukleotiden und Oligonukleotiden", 1993, Gugler, "Aufbau und Anwendung von Systemen zur vereinfachten chemo-enzymatischen Synthese von Oligonukletid-Hybridisierungssonden", 1993, Schmidt, "Neue Methoden zur Synthese und Isolierung langkettiger Oligonucleotide", 1991, Bühler, "Neue photolabile Schutzgruppen für die Oligonucleotidsynthese", 2000, Bretzger, "Wege zur präparativen Oligonucleotidsynthese" 1991, Stengele, "Automatisierte Oligonucleotidsynthese unter Verwendung [beta]-eliminierbare Schutzgruppen", 1991.

Another aspect of the present invention is a quick purification method for labeled nucleotides directly before their use in the labeling reaction. Processes for the sequencing of single molecules (e.g. Balasubramanian WO 03048387, Tcherkassov WO 02088382, Kartalov WO02072892) need labeled nucleotides in a very pure state, because impurities within preparations of nucleotides, such as unlabeled nucleotides, can cause a sequence error. For this reason it is important that the modified nucleotides be essentially free from unmodified nucleotides. Many modified nucleotides used in the said processes comprise one or several groups which are cleavable under mild conditions (Balasubramanian WO 03048387, Tcherkassov WO 02088382).

During storage, such nucleotides can disintegrate to some extent, thus constituting a source of analogous nucleotides without a marker, which would lead to an error in the sequence if used in an incorporation reaction with nucleic acid.

This problem means that a purification procedure has to be applied directly before the use of labeled nucleotides. A standard cleaning procedure for modified nucleotides is, for instance, an HPLC purification with a water-methanol gradient. After such purification the fraction with modified nucleotides must be further processed, for instance, by lyophilisation. Such a purification procedure is laborious.

According to this invention, nuc-macromolecules can be cleansed of the slightest impurities by ultrafiltration directly before use. The filters are selected by pore size in such a way that nucleotides without a marker can pass through the pores. However, nucleotides modified with a macromolecular marker cannot pass through the filter. Using such purification, nuc-macromolecules can be obtained in a pure state in a very short time.

Nuc-macromolecules with a low molecular marker and the intermediate stages of nuc-macromolecules can also be purified by this method, for instance, the nucleotides described in examples 36 and 38.

Another aspect of the invention is the use of the modified exo minus Kienow fragment of DNA polymerase together with nuc-macromolecules in enzymatic reactions, whereby the SH group of the cysteine of the exo minus Klenow fragment of DNA polymerase is modified chemically.

This modification is preferably a covalent modification. Examples of such a modification are seen in alkylation of the SH group, e.g. with alphahalogen-acetyl derivative, e.g. iodacetamide and its derivatives, iodine acetate and its derivatives, or with N-maleimide derivatives, while still further selective reagents for SH groups are known ("Chemistry of protein conjugation and crosslinking" Shan S. Wong 1993 CRC Press Inc). Such modification can also be carried out using a fluorescent dye. Activated fluorescent dyes which react selectively with SH groups are commercially available, e.g. from Molecular Probes Inc.

In one preferred embodiment of the invention, a selective modification of the exo minus Klenow fragment of DNA polymerase occurs on the SH group of the cysteine. An example of the production of such an exo minus Klenow fragment of DNA polymerase is shown in example 43.

In another embodiment, other modifications of DNA polymerase can also be made, such as, for example, modifications of the amino groups of the DNA-polymerase.

In one embodiment, the exo minus Klenow fragment of DNA polymerase modified on the cysteine can be used instead of unmodified DNA polymerase together with nuc-macromolecules in an enzymatic incorporation reaction.

General Suggestions for the Synthesis of Nuc-macromolecules

The nuc-macromolecules according to the invention can be synthesized in different ways. The order of the chemical steps during the coupling steps can vary. For instance, the linker component can be coupled to the nuc-component first, and the marker component can be coupled afterwards. On the other hand, one or more linkers can be coupled to the marker component and then to the nuc-component(s).

The coupling between individual components of nuc-macromolecules can be covalent or affine by its nature. The linking of individual components of the nuc-macromolecules can thereby be accomplished both by chemical and by enzymatical coupling. Couplings to amino or thiol groups represent examples of covalent binding (D. Jameson et al. Methods in Enzymology 1997, v. 278, p. 363-, "The chemistry of the amino group" S. Patai, 1968, "The chemistry of the thiol group" S. Patai, 1974). Biotin-streptavidin bonding, hybridization between complementary strands of nucleic acids or antigen-antibody interactions represent examples of affinity binding.

The macromolecular markers often offer a variety of possibilities for coupling. One macromolecular marker can have a number of coupling positions for the linkers, e.g. several binding sites for biotin, as is true in the case for streptavidin. A macromolecular marker can comprise several amino or thiol groups. The core component of a marker can be modified by a different number of signal-giving or signal-transmitting units. The exact ratio between these marker units can vary. Examples for the modification of polymers with dyes are known (Huff et al. U.S. Pat. No. 5,661,040, D. Brigati U.S. Pat. No. 4,687,732). If nucleic acids are used as macromolecular markers, they can comprise different parts for the coupling of other macromolecules. Other macromolecules, e.g. enzymes, can be bound to one macromolecular marker.

A nuc-macromolecule can carry macromolecular markers with different detection properties, for instance, a nuc-macromolecule can carry several dye molecules as well as sites for the affinity binding (e.g., via hybridization) of further macromolecules.

The coupling between the nuc-components and the linker components is preferably covalent. Many examples of a covalent coupling to nucleotides or their analogues are known (Jameson et al. Method in Enzymology, 1997, v. 278, p. 363-, Held et al. Nucleic acid research, 2002, v. 30 p. 3857-, Short U.S. Pat. No. 6,579,704, Odedra WO 0192284). The coupling can be accomplished, for instance, to phosphate, amino-, hydroxy- or mercapto groups.

Often, the linker component can be built up in several steps. In the first step, for instance, a short linker with a reactive group is coupled to the nucleotide or nucleoside, e.g., propargylamine-linker to pyrimidines Hobbs et al. U.S. Pat. No. 5,047,519 or other linkers, e.g. Klevan U.S. Pat. No. 4,828,979, Seela U.S. Pat. Nos. 6,211,158, 4,804,748, EP 0286028, Hanna M. Method in Enzymology 1996 v. 274, p. 403, Zhu et al. NAR 1994-v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Odedra WO 0192284, Herrlein et al. Helvetica Chimica Acta, 1994, V. 77, p. 586, Canard U.S. Pat. No. 5,798,210, Kwiatkowski U.S. Pat. No. 6,255,475, Kwiatkowski WO 01/25247, Parce WO 0050642, Faulstich et al. DE 4418691, Phosphoroamidite (Glen Research Laboratories, http://www.glenres.com/, Trilink Biotechnologies, S. Agrawal "Protocols for oligonucleotide conjugation", Humana Press 1994, M. Gait "Oligonucleotide synthesis: a practical approach" IRL Press, 1990), dissertation "Synthese basenmodifizierter Nukleosidtriphosphate und ihre enzymatische Polymerisation zu funktionalierter DNA", Oliver Thum, Bonn 2002.

Some compounds are commercially available, e.g., from Trilink Biotechnologies, Eurogentec, Jena Bioscience.

These short linkers serve as coupling units L or their parts, and are constituents of the linker component in the completed nuc-macromolecule.

The coupling of the nucleotide or nucleoside with a short linker to a linker-polymer can be accomplished in the second step. Polymers with reactive functional groups are commercially available (Fluka).

After the coupling of the nucleotide to the polymer, the marker component now can be coupled as the last step.

It is often advantageous to couple a short linker to a nucleoside and then, if necessary, to convert this modified nucleoside into a nucleoside triphosphate (synthesis of triphosphates can be found, for instance, in the following citations: Held et al. Nucleosides, nucleotides & nucleic acids, 2003, v. 22, p. 391, Faulstich et al. DE 4418691, T. Kovacs, L. Ötvös, Tetrahedron Letters, Vol 29, 4525-4588 (1988) or dissertation "Synthese basenmodifizierter Nukleosidtriphosphate und ihre enzymatische Polymerisation zu funktionalierter DNA", Oliver Thum, Bonn 2002). Further modifications can be carried out with nucleoside triphosphate analogs.

Precursors for modified nucleosides are available, for instance, from Trilink Biotechnologies (San Diego, APPROX., the USA) or from Chembiotech (Muenster, Germany).

The coupling between the linker component and the marker component can occur, for instance, between the marker component and the reactive groups on the linker component. Reagents for such couplings are described in detail in "Chemistry of protein conjugation and crosslinking", S. Wang, 1993, ISBN 0-8493-5886-8. The abovementioned patents also describe the methods for handling and coupling several macromolecules for different types of macromolecules. Further examples (for proteins) of couplings to and between the macromolecules are described in "Bioconjugation: protein coupling techniques for the biomedical sciences", M. Aslam, 1996, ISBN 0-333-58375-2; "Reactive dyes in protein an enzyme technology", D. Clonis, 1987, ISBN 0-333-34500-2; "Biophysical labeling methods in molecular biology" G. Likhtenshtein, 1993, 1993, ISBN 0-521-43132-8; "Techniques in protein modification" R. Lundblad, 1995, ISBN 0-8493-2606-0; "Chemical reagents for protein modification" R. Lundblad, 1991, ISBN 0-8493-5097-2; for nucleic acids in "Molecular-Cloning", J. Sambrook, Vol. 1-3, 2001, ISBN 0-87969-576-5, for other types of polymers in "Makromoleküle, Chemische Struktur und Synthesen", Vols. 1, 4, H. Elias, 1999, ISBN 3-527-29872-X.

Because the marker component usually comprises many coupling positions, it is possible to carry out further modifications with the assembled nuc-macromolecules. For instance, further modifications can block or change excess free amino groups.

Depending on the field of application and reaction conditions under which nuc-macromolecules are used, different types of chemical bonds between separate parts of the macromolecules can be advantageous. Thus, for instance, nuc-macromolecules that have covalent, thermostable bonds between different parts are suitable for processes that involve steps at higher temperatures, hybridization or PCR for example.

In the following, some possible methods for synthesis of nuc-macromolecules will be described for the sake of example. These are not intended to restrict the possible synthesis paths or to restrict the possible nuc-macromolecule structures.

The following provides examples of nuc-macromolecules with polyethylene glycol (PEG) as a linker component. Examples of the coupling of PEG to other molecules are shown in "Poly(ethylene glycol): chemistry and biological applications", 1997. In particular, very different reactive groups can be used for the coupling: N-succinimidyl carbonate (U.S. Pat. Nos. 5,281,698, 5,468,478), amines (Buckmann et al. Makromol. Chem. V. 182, p. 1379 (1981), Zalipsky et al. Eur. Polym. J. V. 19, p. 1177 (1983)), succinimidyl propionate and succinimidyl butanoate (Olson et al. in Poly(ethylene glycol) Chemistry & Biological Applications, 170-181, Harris & Zalipsky Eds., ACS, Washington, D.C., 1997; U.S. Pat. No. 5,672,662), succinimidyl succinate (Abuchowski et al. Cancer Biochem. Biophys. v. 7, p. 175 (1984), Joppich et al., Makromol. Chem. 1 v. 80, p. 1381 (1979), benzotriazole carbonate (U.S. Pat. No. 5,650,234), glycidylether (Pitha et al. Eur. J. Biochem. v. 94, p. 11 (1979), Elling et al., Biotech. Appl. Biochem. v. 13, p. 354 (1991), oxycarbonylimidazole (Beauchamp, et al., Anal. Biochem. v. 131, p. 25 (1983), Tondelli et al. J. Controlled Release v. 1, p. 251 (1985)), p-nitrophenyl carbonate (Veronese, et al., Appl. Biochem. Biotech., v. 11, p. 141 (1985); and Sartore et al., Appl. Biochem. Biotech., v. 27, p. 45 (1991)), aldehyde (Harris et al. J. Polym. Sci. Chem. Ed. v. 22, p. 341 (1984), U.S. Pat. Nos. 5,824,784, 5,252,714), maleimide (Goodson et al. Bio/Technology v. 8, p. 343 (1990), Romani et al. in Chemistry of Peptides and Proteins v. 2, p. 29 (1984)), and Kogan, Synthetic Comm. v. 22, p. 2417 (1992)), orthopyridyl-disulfide (Woghiren, et al. Bioconj. Chem. v. 4, p. 314 (1993)), Acrylol (Sawhney et al., Macromolecules, v. 26, p. 581 (1993)), Vinylsulfone (U.S. Pat. No. 5,900,461). Additional examples for coupling PEG to other molecules are shown in Roberts et al. Adv. Drug Deliv. Reviews v. 54, p. 459 (2002), U.S. Patent No. 2003124086, U.S. Patent No. 2003143185, WO 03037385, U.S. Pat. No. 6,541,543, U.S. Patent No. 2003158333, WO 0126692

Other similar polymers can be coupled in a similar way. Examples of such polymers are poly(alkylene glycol), copolymers of ethylene glycol and propylene glycol, poly (olefinic alcohols), poly(vinylpyrrolidone), poly(hydroxy-alkylmethacrylamide), poly (hydroxyalkyl methacrylate), poly(saccharide), poly(x-hydroxy acids), poly(acrylic acid), poly(vinyl alcohol).

The purification of the nuc-components of the nuc-macromolecules is accomplished using conventional means of nucleotide chemistry: for instance, with silica gel chromatography in a water-ethanol mixture, ion exchange chromatography in a salt gradient and reverse-phase chromatography in a water-methanol gradient. Sigma-Aldrich, for example, offers optimized chromatography columns for nucleotide purification.

The purification of macromolecular linker components and marker components can be performed through ultrafiltration, gel electrophoresis, gel filtration and dialysis, see "Bioconjugation: protein coupling techniques for the biomedical sciences", M. Aslam, 1996, ISBN 0-333-58375-2.

The mass of the nuc-macromolecules differs substantially from the mass of the nucleotides. For this reason it is advantageous to use the ultrafiltration for the final purification steps. Since only an average mass is calculated for the nuc-macromolecules, ultrafiltration is also suitable as an analytic method for separation of synthesis products.

It is possible to apply different methods of the macromolecular chemistry for the characterization of the nuc-macromolecules, e.g., UV-vis spectroscopy, fluorescence measurement, mass spectroscopy, fractionation, size exclusion chromatography, ultracentrifugation and electrophoretic technologies, like IEF, denaturating and non-denaturating gel electrophoresis ("Makromoleküle, Chemische Struktur und Synthesen", Band 1, 4, H. Elias, 1999, ISBN 3-527-29872-X, "Bioconjugation: protein coupling techniques for the biomedical sciences", M. Aslam, 1996, ISBN 0-333-58375-2).

The measurement of free SH groups in a substance is carried out with Ellmans reagent (5,5'-dithiobis (2-nitrobenzolic acid), Riddles et al. Method in Enzym. 1983, V. 91, p. 49.

Modified Nucleic Acid Chains

In one embodiment of the invention, nucleic acid chains comprise nuc-components of the nuc-macromolecules as units of the chain.

Synthesis of Modified Nucleic Acid Chains

Nuc-macromolecules can be incorporated or integrated into nucleic acid chains as monomers of a polymer chain by different means. Generally, enzymatic and chemical steps can be used. In the following, different strategies for synthesis will be presented.

Chemical Incorporation:

In chemical coupling, an entire nuc-macromolecule (i.e. structure as nuc-linker-marker) or its parts, e.g. nuc-component or nuc-linker structure, can be used in the reaction. For example, the nuc-component can first be introduced into the nucleic acid chain according to the rules of oligonucleotide synthesis (MWG Biotech, TriLink Biotechnologies, Glen Research Laboratories, S. Agrawal "Protocols for oligonucleotide conjugation", Humana Press 1994, M. Gait "Oligonucleotide synthesis: a practical approach" IRL Press, 1990), wherein one monomer of the chain carries a protective reactive group suitable for modification, e.g. a protected amino-group or mercapto-group. After removal of the protective group, the linker component and the marker component can be coupled to the oligonucleotide. The purification step can comprise ultrafiltration or gel electrophoresis, for example.

Enzymatic Incorporation:

Similarly as in the case of the chemical incorporation, it is possible to use an entire nuc-macromolecule (i.e. structure as nuc-linker-marker) or its parts, e.g. nuc-component or nuc-linker-component, in the enzymatic reaction. For example, nuc-components that carry a reactive group suitable for coupling to a linker component are incorporated into the nucleic acid chain as triphosphates by a template-dependent polymerase-controlled reaction. The linker component or the marker can then be coupled. In one embodiment, a whole nuc-macromolecule can be incorporated into the nucleic acid chain (see example 34).

Modified nucleic acid chains comprise ribonucleic and deoxyribonucleic chains.

The ratio between the nuc-macromolecules and non-modified monomers in a nucleic chain preferably comprises the following ranges: 1:5 and 1:20, 1:20 and 1:100, 1:50 and 1:1000, 1:500 and 1:10000. Several nuc-macromolecules can be also incorporated into a single nucleic acid chain. In one embodiment, one nucleic acid chain comprises only one nuc-macromolecule. In another embodiment, one nucleic acid chain comprises a number of nuc-macromolecules, this number ranging between 2 to 5, 5 to 50, 10 to 100.

In one embodiment, a nuc-macromolecule is integrated at the 5' end of the nucleic acid chain. In a further embodiment, a nuc-macromolecule is integrated at the 3' end of the nucleic acid chain. In a still further embodiment, a nuc-macromolecule is integrated within the nucleic acid chain, wherein the distance to the nearest end of the nucleic acid chain comprises the following ranges (number of nucleotide monomers in the chain to the nearest chain end): 1 to 2, 2 to 4, 4 to 8, 8 to 15, 15 to 30, 30 to 100, 100 to 500.

3. Synthesis of Modified Nucleotides

Methods for Separation

Thin layer chromatography, TLC:

Analytical TLC: "DC-Alufolien 20×20 cm Kieselgel 60 F 254" (VWR, Germany), coated with fluorescent indicator. Visualization was conducted with UV light. Separation medium: ethanol/water mixture (70:30), (separation medium, German "Laufmittel", LM 1) or ethanol/water (90:10), LM2. Preparative TLC plates: silica gel plates with collecting layer (VWR, Germany). LM 1 or LM 2.

Reverse-phase chromatography (RP chromatography), RP-18:

C-18 material (Fluka, Germany), column volume 10 ml, water/methanol gradient. Fractions, each 10 ml, were collected and analyzed with a UV-vis spectrometer. Fractions with similar spectra were combined and lyophilized. HPLC columns with the same material can also be used.

Ion-exchange chromatography:

DEAE cellulose (VWR, Germany), gradient $NH_4HCO_3$ 20 mmol/l to 1 mol/l, fractions were collected under UV/vis-control; those with similar spectra were combined.

Affinity isolation can be used for purification of nuc-macromolecules, e.g. if there are oligonucleotides as a part of the marker component. Such selective isolation can be accomplished for example via a hybridization on the complementary nucleic acid immobilized on a solid phase.

Estimation of the yields of the dye-marked product was conducted with UV-vis spectrometry.

An estimation of saturation degree of the binding to streptavidin was conducted via a control titration with biotin dye (biotin-4-fluorescein, Sigma), 100 μmol/l in 50 mmol/l borate buffer, pH 8, for 5 min at RT. If all potential sites for binding were saturated during the synthesis, there would be no binding of biotin dye to the streptavidin. In the case of insufficient reaction, there would be binding of biotin dye that can be measured by UV-vis.

Material

Diamino PEG 10,000 (diamino-polyethylene glycol 10,000, Sigma), dUTP-M (dUTP allyl amine, Jena Bioscience), TTP (thymidine triphosphate, can be also called dTTP, Sigma), 3'-Amino-TTP (3'-Amino-3'-deoxy-thymidine-triphosphate, Trilink Biotechnologies), PDTP (3-(2-pyridinyl-dithio)-propionic acid, Fluka), 7-(3-phthalimido-1- propynyl)-2'-deoxy-7-deazaguanosine and 7-(3-phthalimido-1-propynyl)-2'-deoxy-7-deazaadenosine (Chembiotech), PDTP-NHS (3-(2-pyridinyl-dithio)-propionic acid-N-hydroxysuccinimidyl ester, Sigma), Cy3 (dye, Amersham Bioscience), Cy3-NHS (Cy3-N-hydroxysuccinimidyl ester, Amersham Bioscience), MEA (mercaptoethylamine, Sigma), DTT (1,4-dithio-DL-threitol, Sigma), CA (cystamine, Sigma), TCEP (tris-(2-carboxyethyl)phosphine, Sigma), DTBP (3,3'-dithio-bis-propionic acid, Fluka), biotin-NHS (biotin-N-hydroxysuccinimidyl ester, Sigma). J-Ac (iodoacetate, Sigma), iodacetamide (Sigma), TEAE (tris-(2-Aminoethyl)amine, Sigma), maleimido-ES-NHS (maleimido-acetic acid-N-hydroxysuccinimidyl ester, Sigma), EDA (ethylendiamine, Sigma), CDI (1,1'-carbonyldiimidazole, Sigma), PAS 100 kDa (polyacrylic acid, 100 kDa, Aldrich), NHS-PEG-maleimide, 3,400 Da, biotin-PEG-NHS, 5,000 Da, Fmoc-PEG-NHS, 3,400 Da, mPEG-SPA 5,000 Da, mPEG-SPA 20,000 Da (Nektar), diamine-PEG, 6,000 Da (Fluka), 3'-biotin-dT31, an oligonucleotide with a sequence of 31 thymidine monophosphates with a biotin-molecule coupled to the 3'-end (MWG Biotech), 3'-SH-Oligo-dT30, an oligonucleotide with a sequence of 30 thymidine monophosphates with the mercapto group at the 3'-end (MWG-Biotech), 3'-amino-oligo-dT31-5'-Cy3, an oligonucleotide with a sequence of 31 thymidine monophosphates with the amino group coupled to the 3'-end via 6-C linker and the Cy3-dye coupled to the 5'-end (MWG-Biotech,), SA (streptavidin, Roche), SA-Cy2 (streptavidin modified with Cy2-dye, Amersham Bioscience). QDot (Qdot 605 streptavidin conjugate, Quantum Dot). Polylysine 1000-2000 (poly-L-lysine hydrobromide 1000-2000 Da, Fluka), polylysine 10,000-20,000 (poly-L-lysine hydrobromide 10,000-20,000 Da, Fluka).

List of Suppliers and Companies:
Aldrich—see Sigma
Amersham—Amersham Bioscience, Freiburg, Germany
Chembiotech—Chembiotech, Münster, Germany
Fluka—see Sigma
Jena Bioscience—Jena Bioscience, Jena, Germany
Molecular Probes—Molecular Probes Europe, Leiden, Netherlands
MWG—MWG Biotech, Ebersberg near Munich, Germany,
Nektar—Nektar Molecular Engineering, previous Shearwater Corporation, Huntsville, Ala., USA
Quantum Dot—Quantum Dot Hayward, Calif., USA
Roche—Roche, Mannheim, Germany
Sigma—Sigma-Aldrich-Fluka, Taufkirchen, Germany
Trilink—Trilink Biotechnologies Inc. San Diego, Calif., USA, Organic solvents were purchased from Fluka at p.a. purity grade or were dried according to standard procedures. For solvent mixtures, the mixing ratio is stated in terms of volume to volume (v/v).

SYNTHESIS OF INDIVIDUAL COMPONENTS

Example 1 dUTP-AA-PDTP, FIG. 10A dUTP-AA (20 mg) was dissolved in 1 ml of water and the pH value was adjusted to 8.5 with NaOH. PDTP-NHS (60 mg dissolved in 0.5 ml methanol) was added dropwise to this aqueous solution of dUTP-AA under stirring. The reaction was carried out at 40° C. for 2 hours. TLC Analysis: dUTP-AA-PDTP (in LM 1 Rf 0.45).

The isolation of the product from excess of PDTP-NHS and PDTP was performed on preparative TLC plates, LM 2. The resulting products, dUTP-M-PDTP and dUTP-M, were eluted from the plate with water and dried.

This dUTP analog comprises a disulfide bond that can react with other thiols in a thiol exchange reaction under mild conditions resulting in a formation of a new cleavable bond.

This example illustrates a general possibility of introducing further modifications into the nucleotides. Other base-modified nucleotide analogs, such as 7-deaza-aminopropargyl-deoxy-guanosine triphosphate, 7-deaza-aminopropargyl deoxy-adenosine triphosphate, 5-aminopropargyl-deoxy-uridine triphosphate, 5-aminoallyl-deoxy-uridine triphosphate, and 5-amino-propargyl-deoxy-cytidine triphosphate, can be modified in the same way. Ribonucleotides as well as 2'-deoxyribonucleotides as well as 2',3'-dideoxyribonucleotides can be used in such reactions, FIGS. 11 to 14.

Example 2 dCTP-PA-PDTP, FIG. 10B

The synthesis was conducted as described above for dUTP-AA-PDTP, example 1.

Figure 15:
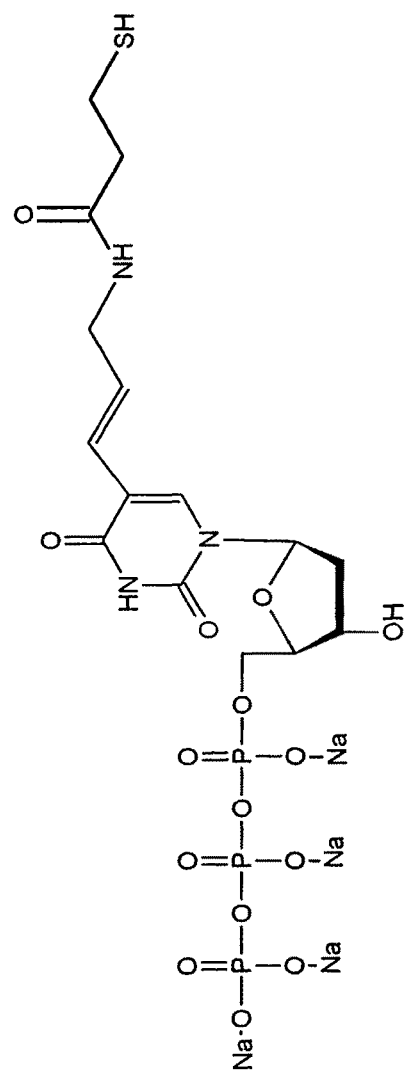
FIG. 15 is a schematic depicting dUTP-AA-propionate-SH.

Example 3 dUTP-AA-propionate-SH, FIG. 15

One ml of aqueous TCEP solution, 250 mmol/l, pH 8, adjusted with NaOH, was added to 200 μl 40 mmol/l aqueous solution of dUTP-M-PDTP, and the reaction was allowed to proceed for 10 min at RT under stirring. The separation of nucleotides from other reagents took place on preparative TLC plates, LM 2. Under these conditions the product, dUTP-AA-propionate-SH, remains on the starting line. Nucleotides were eluted from the plate with water and dried.

This dUTP analog comprises a reactive SH group that can be easily modified, e.g. by thiol exchange reaction resulting in a new disulfide bond.

Example 4

Figure 16:
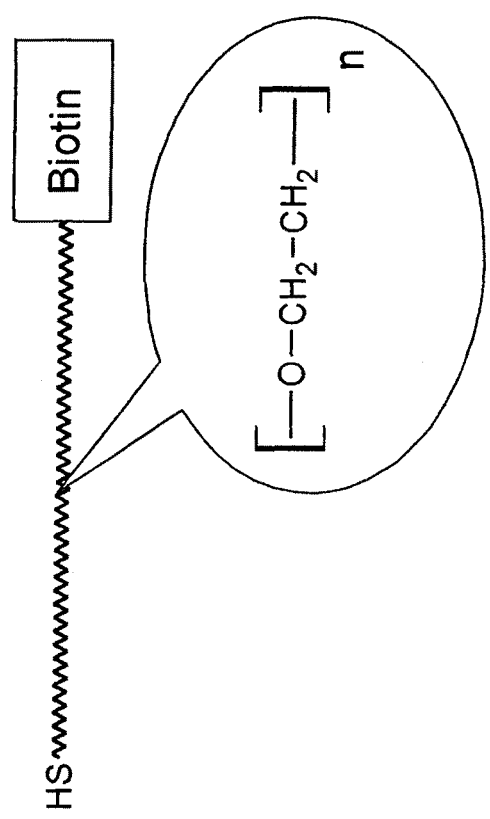
FIG. 16 is a schematic of Biotin-PEG-Ethyl-SH.

Biotin-PEG-Ethyl-SH, FIG. 16

Biotin-PEG-NHS (10 mg) was added to 200 μl aqueous CA solution (100 mmol/l), pH 8.5, adjusted with NaOH; the reaction proceeded at 40° C. for 18 hours under stirring. Then 200 μl of TCEP solution (0.5 mol/l), pH 8.0, was added and the reaction was allowed to proceed for a further 10 min at RT under stirring. The product was separated from low-molecular-weight compounds by ultrafiltration at a MWCO (Molecular weight cutoff) of 3,000, yield 35%.

The product comprises a reactive SH group that can be easily modified, e.g. by thiol-exchange reaction resulting in a new disulfide bond.

Example 5

Bis-dithio-(ethyl-PEG-biotin)

Biotin-PEG-NHS (100 mg) was added to 1 ml aqueous CA-Solution (2 mmol/l), adjusted to pH 8.5 with NaOH, and stirred at RT for 18 hours. The product was isolated from the low-molecular-weight compounds via Ultrafiltration at a MWCO of 10,000 and lyophilized, yield 13%.

The product comprises a disulfide bond that can react with other thiols in a thiol exchange reaction.

Example 6

Figure 17:
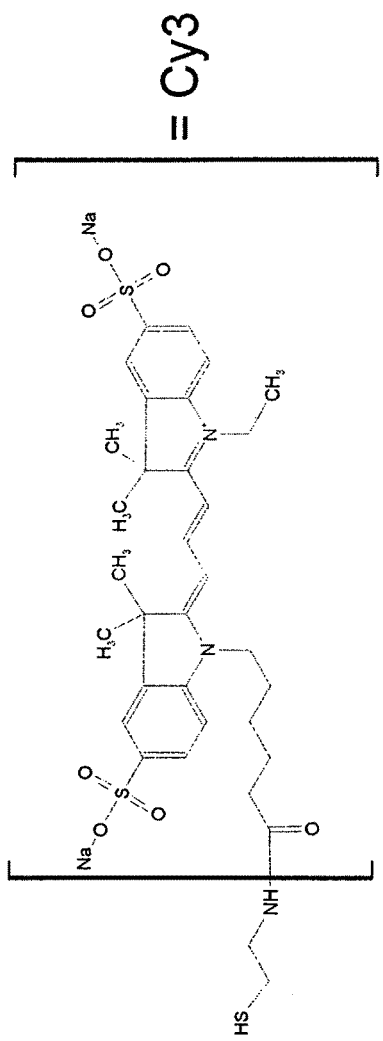
FIG. 17 is a schematic of MEA-Cy3.

MEA-Cy3, FIG. 17

Cy3-NHS was added to 1 ml aqueous CA-solution (200 mmol/l), adjusted to pH 8.5 with NaOH, until the concentration of the Cy3 dye was 10 mmol/l. The reaction was incubated under continuous stirring at RT for 10 min. Then, 1 ml aqueous TCEP solution (0.5 mol/l), adjusted to pH 8.0 with NaOH, was added, and the reaction was allowed to proceed at RT for a further 10 min. The product was purified on RP-18 (water/methanol gradient), fractions were combined and their volume was reduced to 0.5 ml, yield 93%, UV-vis.

The product has a reactive SH group that can be easily modified, e.g. by thiol-ex change reaction resulting in a new disulfide bond.

Example 7

Figure 18:
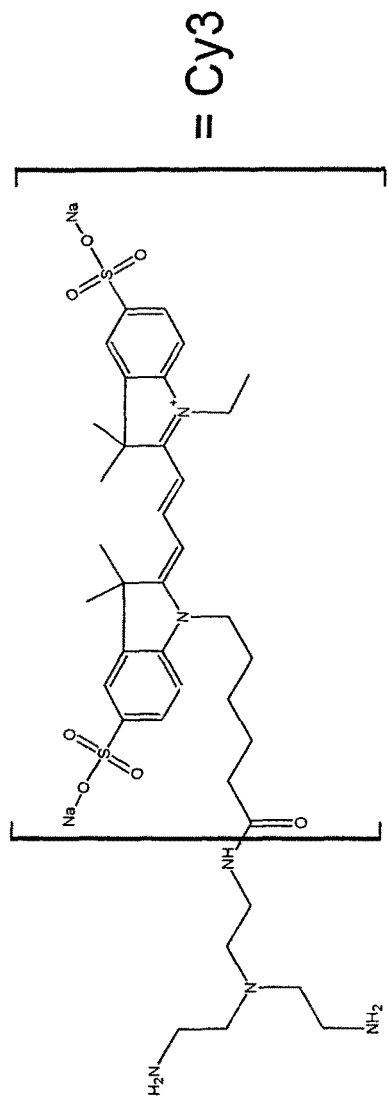
FIG. 18 is a schematic of Cy3-TEAE.

Cy3-TEAE, FIG. 18

Cy3-NHS was added to 1 ml aqueous TEAE-solution (300 mmol/l), adjusted to pH 8.5 with NaOH, until the concentration of the dye reached 5 mmol/l. The reaction was stirred at RT for 10 min. The product was purified on RP-18 and reduced to 0.5 ml, yield 82%, UV-vis.

The product comprises two amino groups that can be modified with other reagents and new functionalities can be coupled to the dye.

Example 8

Figure 19:
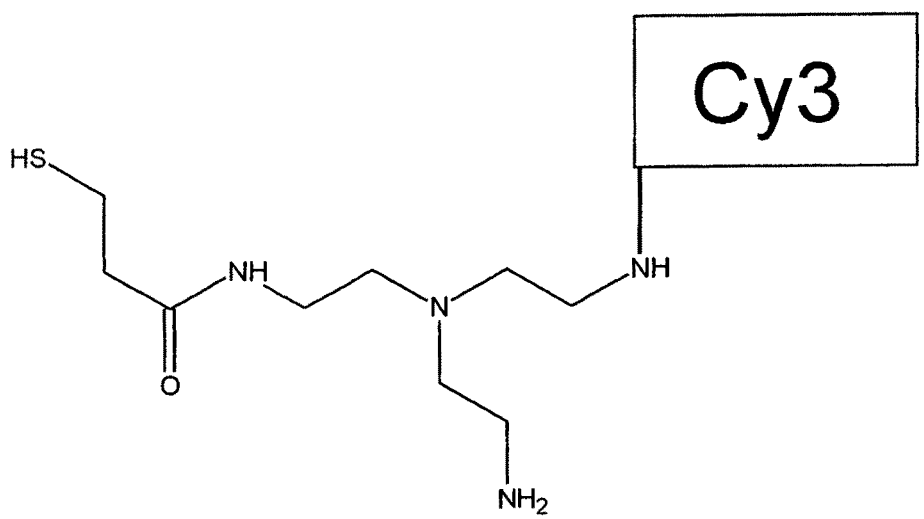
FIG. 19 is a schematic of Cy3-TEAE-Propionate-SH.

Cy3-TEAE-Propionate-SH, FIG. 19

A fresh prepared methanolic solution of PDTP-NHS (30 mmol/l, 30 µl) was added to 300 µl aqueous solution of Cy3-TEAE (2 mmol/l), pH 7.5. The progress of the reaction was observed via TLC, LM 1. The products have the following Rf under these TLC conditions: Rf. 0.55 (Cy3-TEAE-PDTP) and 0.95 (Cy3-TEAE-(PDTP)$_2$). After 1 h at RT, the reaction was stopped and the products were purified on TLC (LM 1). Cy3-TEAE-PDTP (Rf. 0.55) was isolated, dried and dissolved in 200 µl of water. An aqueous TCEP-solution (0.5 mol/l, 0.1 ml), pH 8.0, was added to this Cy3-TEAE-PDTP solution and the reaction was allowed to proceed for 10 min at RT. The product, Cy3-TEAE-propionate-SH, was purified on RP-18 (water/methanol gradient) the volume was reduced to 0.5 ml, yield 26%, UV-vis.

The product comprises a reactive SH group that can be easily modified, in a thiol exchange reaction resulting in a new disulfide bond for example, and an amino-group that can also be modified.

Example 9

Figure 20:
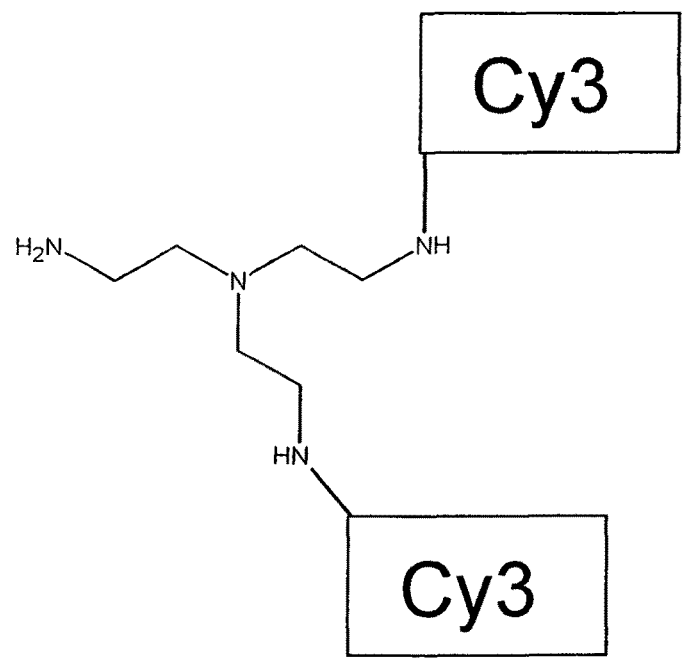
FIG. 20 is a schematic of TEAE-(Cy3)$_2$.

TEAE-(Cy3)$_2$, FIG. 20

Cy3-NHS was added to 1 ml aqueous TEAE solution (2 mmol/l) until the concentration of the dye was 4 mmol/l. The reaction was allowed to proceed under stirring for 10 min at RT. The product, TEAE-(Cy3)$_2$, (Rf. 0.45) was purified from other reagents on preparative TLC in LM 1 and eluted with 50 mmol/l borate buffer, pH 9. Then, TEAE-(Cy3)$_2$ was purified on RP-18 and eluted with 50% ethanol-water and concentrated to a volume of 0.5 ml, yield 22%, UV-vis.

Example 10

Figure 21:
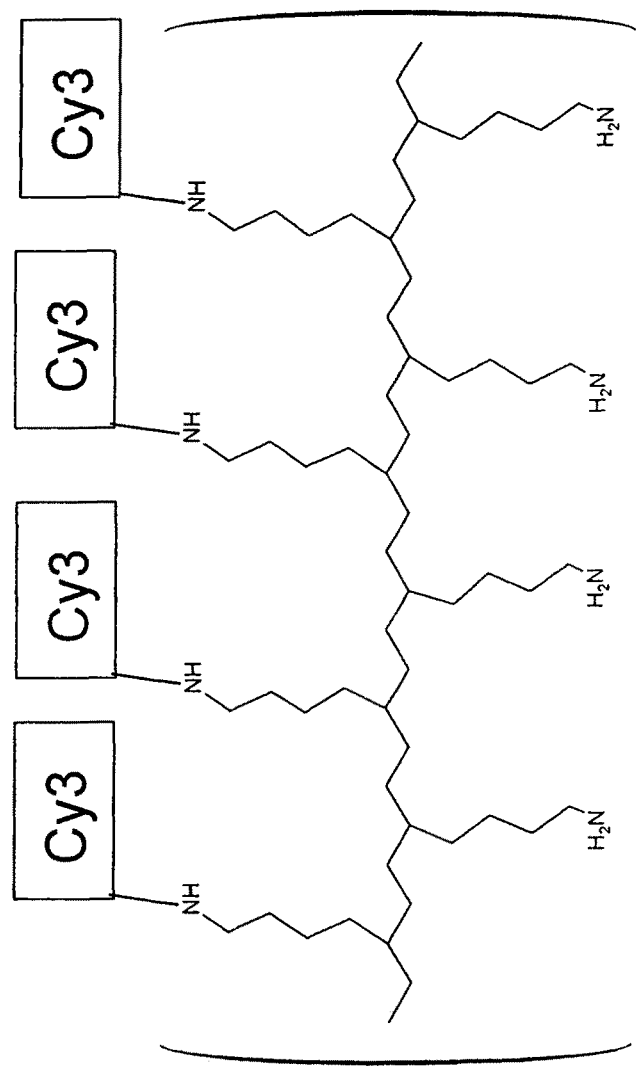
FIG. 21 is a schematic of Polylysine-(Cy3)$_n$.

Polylysine-(Cy3)$_n$, n=10-15, Polylysine 10,000-20,000, FIG. 21

Cy3-NHS was added to 1 ml aqueous polylysine-solution (1 mmol/l) until the concentration of the dye was 18 mmol/l. The reaction was allowed to proceed at RT for 40 min under stirring. Purification of the modified polylysine was carried out via ultrafiltration, 3000 MWCO. UV-vis was used to determine the average number of the Cy3-dye molecules.

Polylysine is an example for a core component to which several marker units can be coupled, e.g. dyes. Distribution of the Cy3 molecules on polylysine was estimated from the known size differences of the polylysine molecules and average number of the coupled Cy3 molecules that was determined.

Example 11

Figure 22:
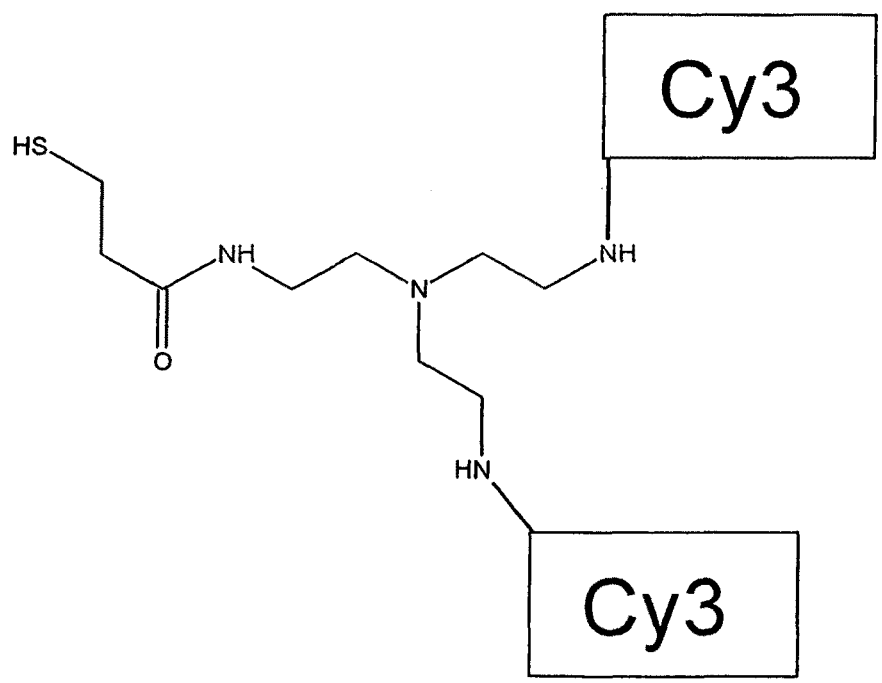
FIG. 22 is a schematic of TEAE-(Cy3)-2-propionate-SH.

TEAE-(Cy3)2—PDTP and TEAE-(Cy3)-2-propionate-SH, FIG. 22

PDTP-NHS (10 mg) was added to 200 µl aqueous solution of TEAE-(Cy3)$_2$ (1 mmol/l) and the reaction was allowed to proceed at RT for 1 h under stirring. The course of the reaction was controlled with TLC, LM 1. After 1 hour there was a nearly quantitative conversion of TEAE-(Cy3)$_2$ (Rf. 0.45) into TEAE-(Cy3)$_2$—PDTP, (Rf. 0.85). The product of the reaction was divided in two equal parts.

The product, TEAE-(Cy3)$_2$—PDTP, from the first part was purified on RP-18 and lyophilized (yield 82%, UV-vis). This product comprises a disulfide bond that can participate in a thiol exchange reaction, i.e. other components can be coupled.

The second part was reacted with 0.1 ml of an aqueous solution of TCEP (0.5 mol/l), pH 8.0, at RT for 10 min under stirring. The product, TEAE-(Cy3)2-propionate-SH, was purified on RP-18, yield 68%, UV-vis.

The product comprises a reactive SH group, that can be modified, e.g. in a thiol exchange reaction resulting in a new disulfide bond.

Example 12

Figure 23:
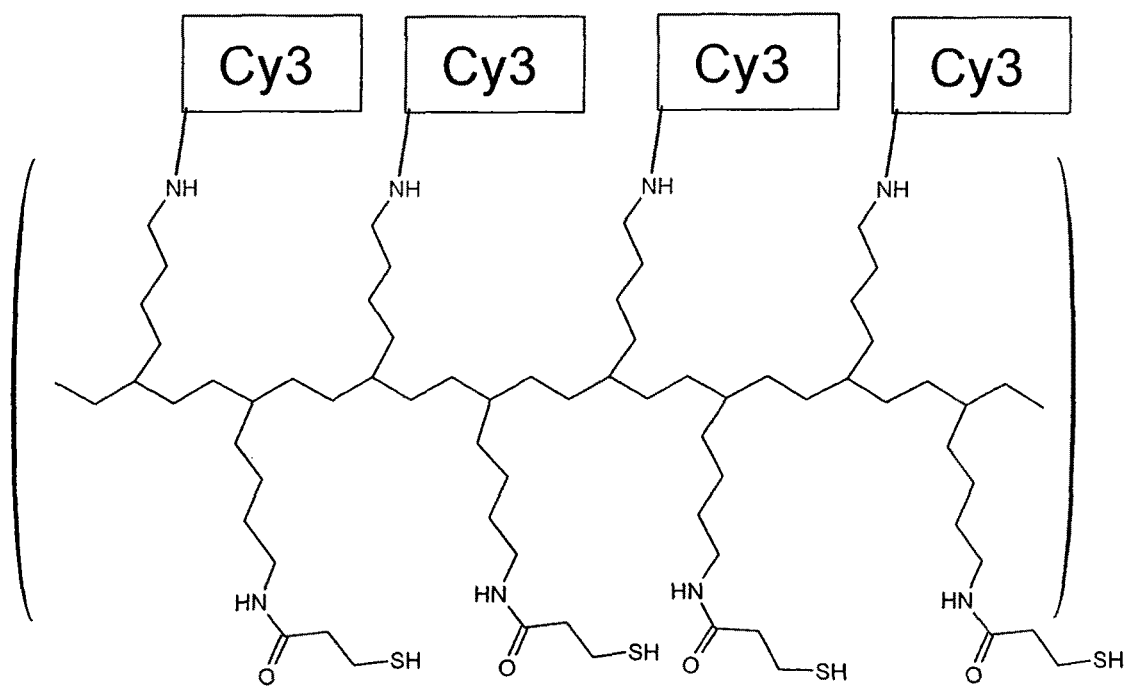
FIG. 23 is a schematic of (HS-propionate)$_m$-polylysine-(Cy3)$_n$, which comprises multiple reactive SH groups.

(HS-propionate)$_m$-polylysine-(Cy3)$_n$, (n=10-15, m=3-9, polylysine 10,000-20,000), FIG. 23

PDTP-NHS (10 mg) was added to 200 µl aqueous solution of Polylysine-(Cy3)$_n$ (1 mmol/l) and the reaction was allowed to proceed at RT for 1 hour under stirring. The product (PDTP)$_m$-polylysine-(Cy3)$_n$ was purified from the rests of PDTP via ultrafiltration and then dissolved in 100 µl water. Next, 0.1 ml TCEP solution (0.5 mol/l), pH 8.0, was added and the mixture was stirred at RT for another 10 min. The product, (HS-propionate)$_m$-polylysine-(Cy3)$_n$, was separated from low-molecular-weight compounds at 3,000 MWCO. The product comprises several reactive SH groups that can be modified, e.g. in a thiol exchange reaction resulting in new disulfide bonds.

Example 13

TTP-3'-O-Propionat-SH, FIG. 24A

The synthesis of 3'-modified nucleotides proceeded according to Gottikh et al. Tetrahedron, 1970, v. 26, 4419-, Schäfer et al. Method in Enzymology, 1986, v. 126, pp. 682-.

DTBP, 210 mg, was dissolved in 1 ml DMF. CDI, 320 mg, was added to this solution and the resulting mixture as stirred for 1 hour at RT. Next, 10 µl methanol was added and, after another 10 min, 100 µl of this solution, 1 mol/l, was added to 300 µl aqueous solution of TTP, 100 mmol/l, adjusted to pH 8.5 with NaOH, and the resulting solution was thoroughly stirred at RT for approximately 4 hours. Nucleotides were isolated by precipitation with ethanol and then dissolved in 300 µl water. Next, 200 µl TCEP solution (0.5 mol/l), pH 8.0, was added and, after 10 min at RT, nucleotides were precipitated once again. Preparative separation was not conducted at this stage of synthesis, yield 13%, UV-vis.

The product comprises a reactive SH group that can easily be modified, e.g. in a thiol exchange reaction resulting in new disulfide bond.

Example 14

TTP-3'-Amino-PDTP, FIG. 24B

The synthesis was conducted as described for dUTP-M in example 1. The following educts were used: 3'-amino-3'-deoxy-TTP, 100 µl, 10 mmol/l solution, pH 8, and PDTP-NHS, yield 19%, UV-vis.

This product comprises a disulfide bond that can participate in thiol exchange reaction, i.e. other components can be coupled.

Other nucleotides modified at the 3'-end, e.g. with a short linker, can also be used. Examples of the synthesis for such compounds are as follows: Metzker et al. Nucleic acid Research 1994, v. 22, s. 4259, Canard et al. Gene, 1994, v. 148, p. 1, Hovinen et al. 1. Chem. Soc. Perk. Trans. 1994 v. 1, p. 211, Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, Faulstich DE 4418691.

Additional examples of base-modified nucleotides that can be used a nuc-component are described in Balasubramanian WO 03048387 and still further examples in "Nucleotide Analogs" Scheit, 1980, ISBN 0-471-04854-2, "Nucleoside and Nucleic Acid Chemistry", Kisakürek 2000, "Anti-HIV Nucleosides" Mitsuya, 1997, "Nucleoside Analogs in cancer therapy", Cheson, 1997. A person skilled in the art may recognize that still other modified nucleotides can be used.

Examples for Coupling Linker Components and Marker Components to Nuc-component

Figure 25:
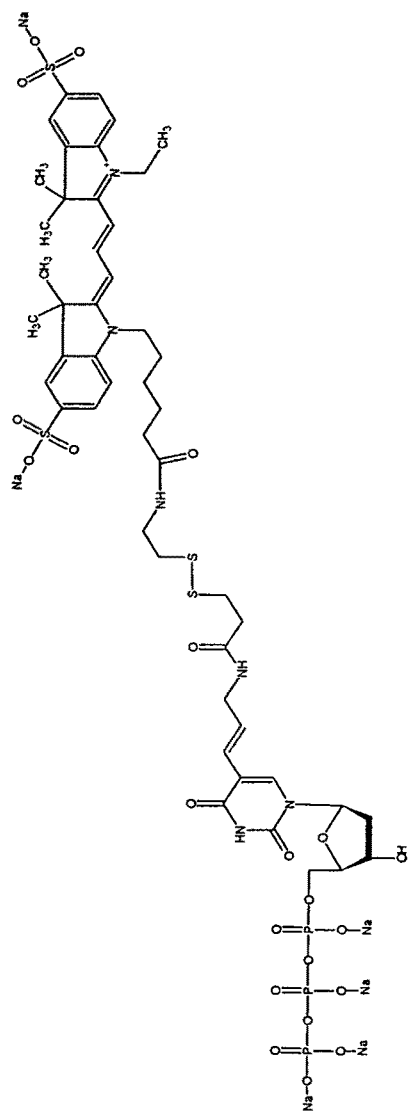
FIG. 25 depicts dUTP-AA-SS-MEA-Cy3.

Example 15 dUTP-AA-SS-MEA-Cy3, FIG. 25 dUTP-AA-PDTP (50 µl, 30 mmol/l in 50 mmol/l borate buffer, pH 9.5) was added to 100 µl, 10 mmol/l MEA-Cy3 in 50 mmol/l borate buffer, pH 9.5. After 1 hour, dUTP-AA-SS-MEA-(Cy3) was separated from MEA-Cy3, Rf. 0.9 by TLC, LM 1, Rf. 0.6. Next, dUTP-M-SS-MEA-(Cy3) was purified from dUTP-AA-PDTP on RP-18, yield 67%, UV-vis.

The resulting compound comprises a nucleotide functionality and a low-molecular-weight marker functionality. This product is a conventionally modified nucleotide by definition: the linker length is less than 30 atoms and the marker component has a low molecular weight. It can be considered as a typical conventional modified nucleotide with only one low molecular marker.

Polymerases do accept this compound as a substrate (e.g. Klenow-exo minus fragment), example 34A.

Figure 26:
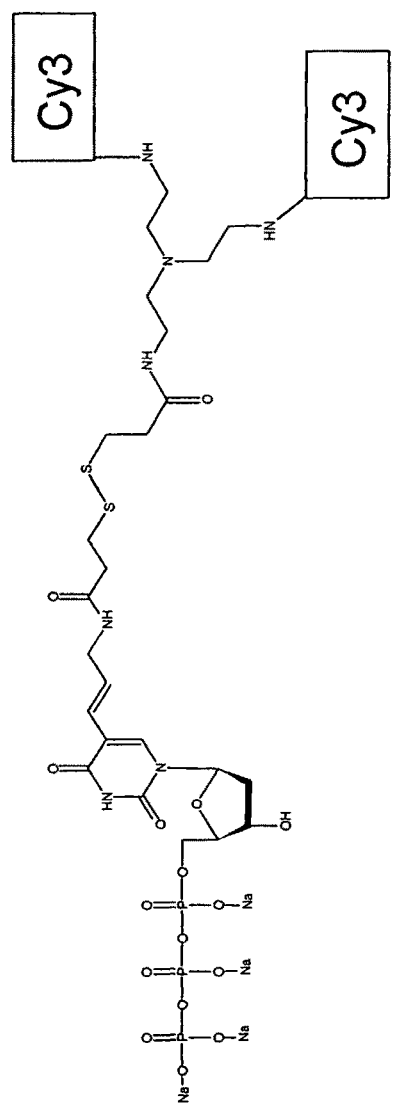
FIG. 26 depicts dUTP-AA-SS-TEAE-(Cy3)$_2$.

Example 16 dUTP-AA-SS-TEAE-(Cy3)2, FIG. 26 dUTP-AA-SS-TEAE-(Cy3)$_2$ was synthesized similarly as dUTP-AA-SS-MEA-(Cy3), example 15, except that TEAE-(Cy3)-2-propionate-SH was used instead of MEA-Cy3, yield 43%, UV-vis.

The obtained compound comprises a nucleotide functionality and two low-molecular-weight marker functionalities.

This product is a conventional nucleotide by definition: the linker length is less than 30 atoms and the marker component has a low molecular weight. This compound can be used as an example of conventional nucleotides with several low-molecular-weight marker units.

Polymerases do not accept this compound as a substrate (e.g. Klenow exo minus polymerase). The modification leads to the loss of substrate properties.

Figure 27:
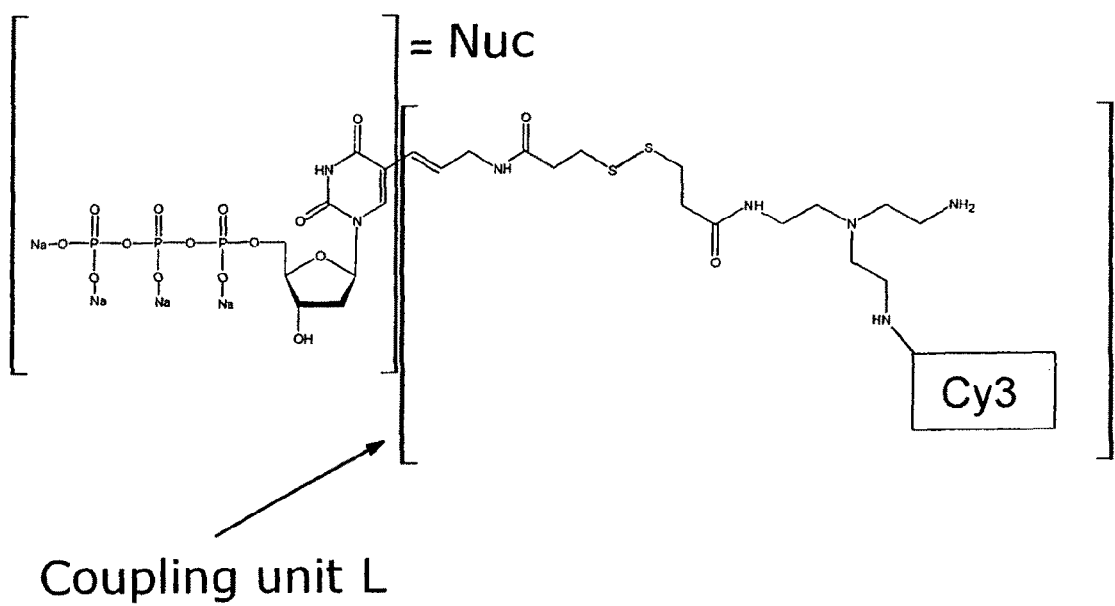
FIG. 27 depicts dUTP-AA-SS-propionate-TEAE-Cy3.

Example 17 dUTP-AA-SS-propionate-TEAE-Cy3, FIG. 27 dUTP-AA-SS-propionate-TEAE-Cy3 was synthesized similarly as dUTP-AA-SS-MEA-Cy3, example 15, except that Cy3-TEAE-propionate-SH was used instead of MEA-Cy3, yield 37%, UV-vis.

The resulting compound comprises a nucleotide functionality and a low molecular weight marker functionality. The linker comprises a free amino group that can be modified. This product is a conventionally modified nucleotide by definition: the linker length is less than 30 atoms and marker component has a low molecular weight. Polymerases can use this nucleotide as a substrate.

Example 18

(dUTP-AA-SS-propionate)m-polylysine-(Cy3)n
Educts:
dUTP-AA-PDTP
(HS-propionate)m-Polylysine-(Cy3)n, n=10-15, m 3-9, Polylysine 10,000-20,000.

An aqueous solution of dUTP-AA-PDTP (50 µl, 20 mmol/l, in 50 mmol/l borate buffer, pH 9.0) was mixed with 20 µl aqueous (HS-propionate)m-Polylysine-(Cy3)n, approximately 1 mmol/l, and the reaction was allowed to proceed at RT for 18 hours under stirring. The product was separated from low-molecular-weight substances via ultrafiltration, 30,000 MWCO.

The obtained compound comprises a nucleotide functionality and a macromolecular-marker functionality. The compound is a conventional nucleotide by definition: the linker-length is less than 30 atoms, and the marker component is macromolecular. Polymerases do not accept this compound as a substrate (e.g. Klenow exo minus polymerase or terminal transferase). The modification resulted in the loss of substrate properties.

Figure 28:
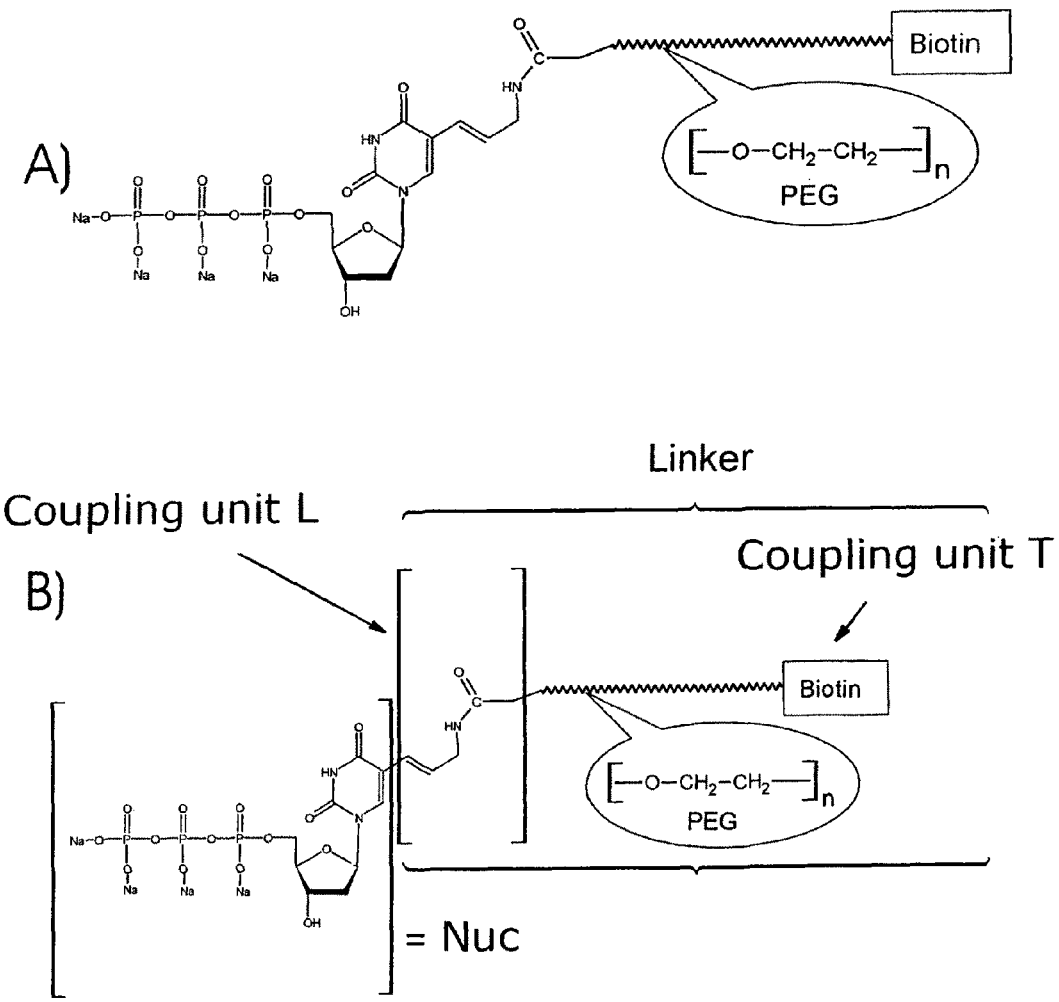
FIG. 28 is a schematic of dUTP-AA-PEG-biotin.

Example 19 dUTP-AA-PEG-biotin, FIG. 28

Biotin-PEG-NHS (10 mg) was added to 100 µl aqueous solution of dUTP-AA, 50 mmol/l, pH 8.0, and stirred at 40° C. for 18 h. Next, the unreacted nucleotide was separated by ultrafiltration, 3,000 MWCO, and the product, dUTP-AA-PEG-biotin, was thoroughly washed with water.

This compound comprises a nucleotide functionality and a macromolecular linker. Biotin represents the coupling unit (T). Macromolecular structures can be coupled to this coupling unit (T), e.g. streptavidin, without the nucleotide analogs losing their substrate properties. This nuc-macromolecule can be used as a substrate for polymerases.

Also, biotin can be considered as a low-molecular marker unit coupled to a long linker that comprises a signal-transmitting function.

Figure 29:
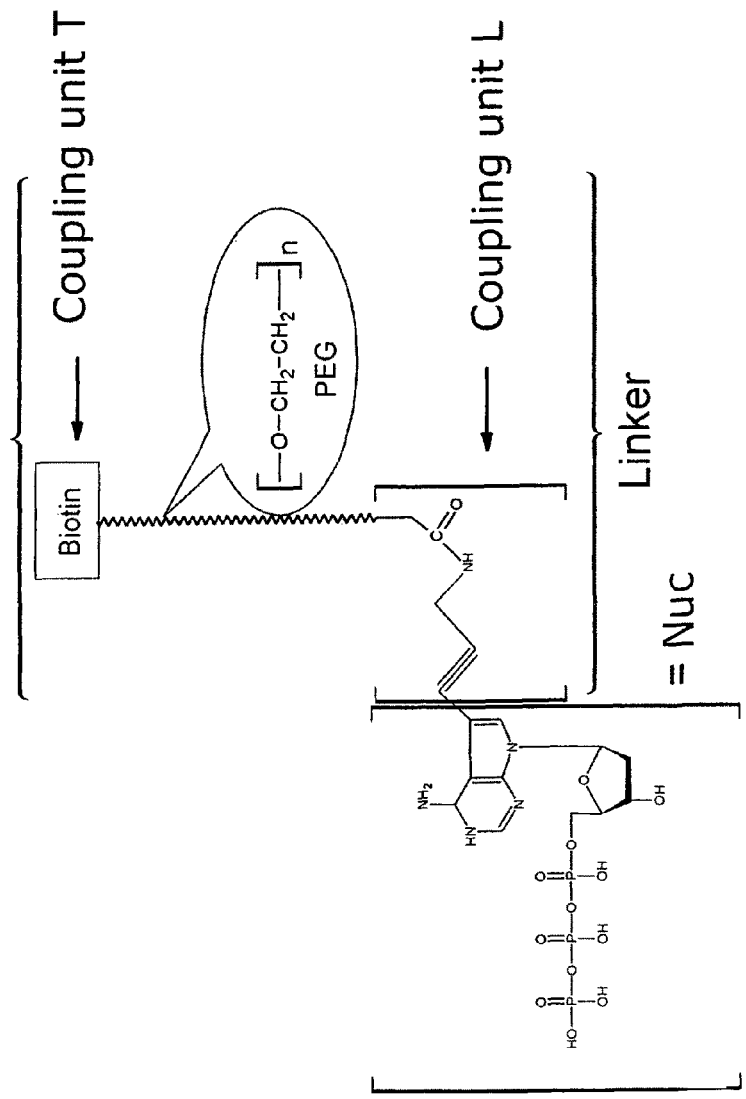
FIG. 29 is a schematic showing an intermediate compound for a nuc-macromolecule by definition wherein the linker-length is significantly longer than 30 atoms and additional macromolecules can be coupled to the coupling unit (T). This figure shows that it is generally possible to modify nucleotides by the procedure of the disclosure.

This product is an intermediate compound for a nuc-macromolecule by definition: the linker-length is significantly longer than 30 atoms and additional macromolecules can be coupled to the coupling unit (T). This example shows that it is generally possible to modify nucleotides. Other base-modified nucleotide analogs, e.g. 5-propargylamino-dCTP, 7-deaza-aminopropargyl-dGTP, 5-amino-propargyl-dUTP and 7-deaza-aminopropargyl-dATP (FIG. 29) can be modified in a manner similar to the described procedure. Ribonucleotides, 2'-deoxyribonucleotide or 2',3'-dideoxyribonucletide can be used, FIGS. 11 to 14.

Other polymers, e.g. PEG derivates, can be used as a linker in a similar way. dATP-PA-PEG-$NH_2$ constitutes one example.

Fmoc-PEG-NHS (Fmoc-protected $NH_2$-PEG-NHS), 10 mg, was added to 100 µl aqueous solution of 7-deaza-7-aminopropargyl-dATP (custom-synthesized from 7-(3-Phthalimido-1-propynyl)-2'-deoxy-7-deazaadenosine by Jena Bioscience, Germany), 50 mmol/l, pH 8.0, and stirred at 40° C. for 18 hours. Next, the pH-value was increased to 11 and the reaction mixture was stirred at RT for 2 additional hours. Next, the resulting product, dATP-PA-PEG-$NH_2$, was separated from the unreacted nucleotide by ultrafiltration, 3,000 MWCO, and washed with water several times.

This compound comprises a nucleotide functionality and a macromolecular linker. The $NH_2$ group is a coupling unit (T) for the marker component. Macromolecular structures can be coupled to this coupling unit (T), e.g. polyacrylic acid derivatives, without these nucleotide analogs losing their substrate properties. This nuc-macromolecule can be used as a substrate for polymerases.

Example 20

TTP-3'-Amino-PEG-Biotin,

The synthesis was conducted similarly as for dUTP-AA-PEG-biotin, example 19.

3'-amino-3'-deoxy-TTP and biotin-PEG-NHS were used as adducts.

This compound comprises a nucleotide functionality and a macromolecular linker and a low-molecular-weight marker unit (biotin) that has a signal-transmitting function. Signal-carrying streptavidin molecules can be coupled to the biotin.

The product represents an intermediate compound for nuc-macromolecules by definition: the linker length is significantly longer than 30 atoms and the marker component has low molecular weight. Other nucleotide analogs with an amino group at the 3'-position can also be synthesized in similar way.

Example 21 dCTP-PA-PEG-maleimide,

The synthesis was conducted as described for dUTP-M-PEG-biotin, example 19. dCTP-PA and maleimide-PEG-NHS were used as adducts.

This compound has a nucleotide functionality and a macromolecular linker. The coupling unit (T) at this linker is the maleimide group. Macromolecular signal-carrying molecules with one or more SH groups can be coupled to this maleimide functionality. This maleimide group can also be considered as a low-molecular-weight marker unit with signal-transmitting function that is coupled to a long linker.

This product is an intermediate compound for a nuc-macromolecules by definition: the linker-length is longer than 30 atoms and the marker component has low molecular weight. Other macromolecular structures can be coupled to this marker component without these analogs losing their substrate properties.

This example shows that it is generally possible to modify nucleotides. Other base-modified nucleotide analogs, e.g. 5-propargylamino-dCTP, 7-deaza-aminopropargyl-dGTP, 5-amino-propargyl-dUTP and 7-deaza-aminopropargyl-dATP can also be modified in the above way. Ribonucleotides, 2'-deoxyribonucleotides or 2', 3'-dideoxyribonucletides can be used, FIGS. 11 to 14.

Figure 30:
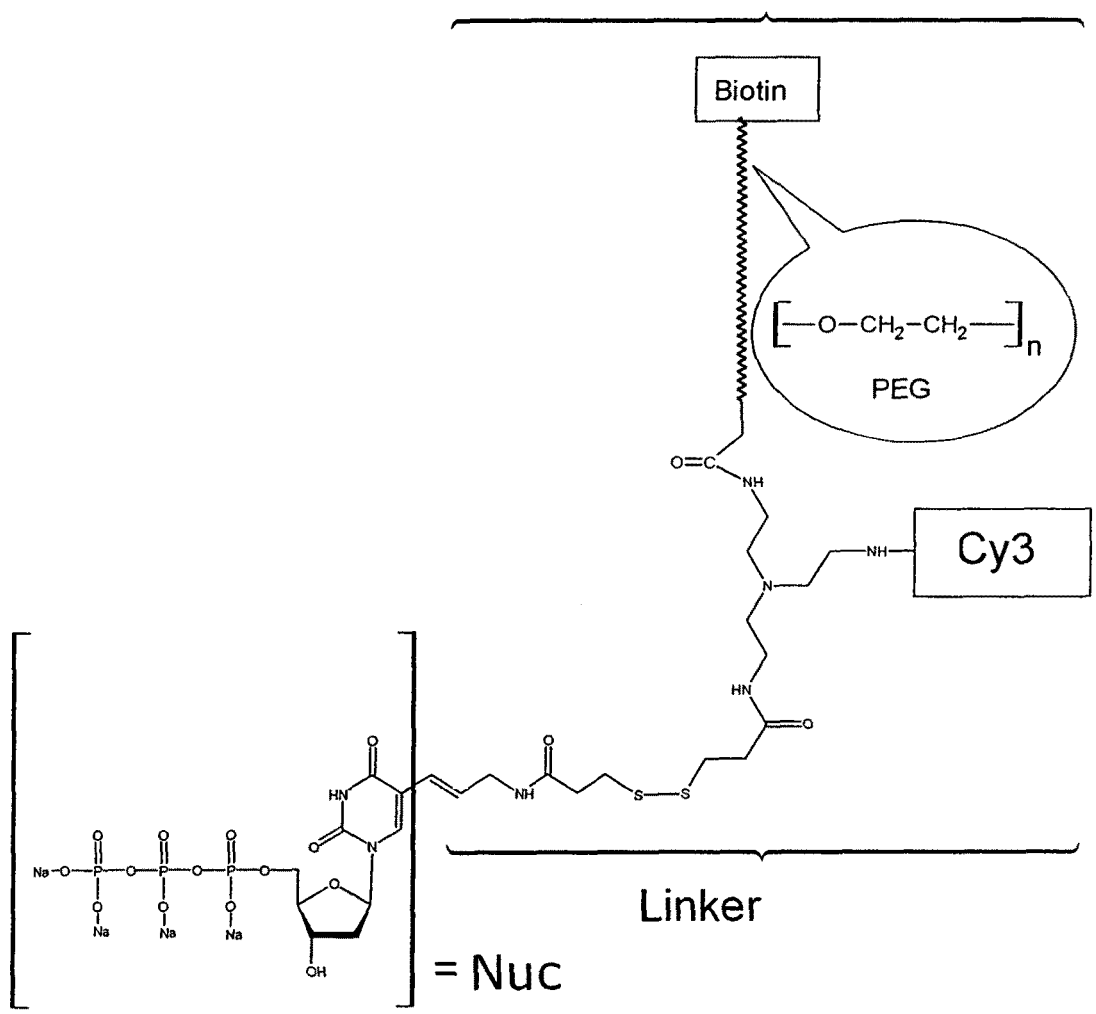
FIG. 30 depicts dUTP-AA-SS-Propionate-TEAE-(Cy3)-PEG-Biotin.

Example 22 dUTP-AA-SS-Propionate-TEAE-(Cy3)-PEG-Biotin, FIG. 30

The synthesis was conducted in a manner comparable to that described for dUTP-AA-PEG-Biotin (example 19). dUTP-AA-SS-Propionate-TEAE-Cy3 and Biotin-PEG-NHS were used as adducts. Separation of the product from non-reacted dUTP-analog was conducted by ultrafiltration, 3.000 MWCO.

This compound comprises a nucleotide functionality, a fluorescent dye, a macromolecular linker and a low molecular weight marker functionality (biotin), that has signal transmitting properties. The biotin molecule can be considered as a coupling unit (T) as well.

This product is by definition an intermediate stage of a nuc-macromolecule: the linker length is greater than 30 atoms, the biotin is a coupling unit (T). Further macromolecules can be coupled to this coupling unit (T) without loss of the substrate properties of the nucleotides. This analog acts as a substrate for polymerases.

The dye acts as a sterically demanding group, which allows for only one enzymatic incorporation of a nuc-macromolecule into the growing strand by a polymerase. Properties of such analogs are described in more detail in Tcherkassov WO 02088382.

Figure 31:
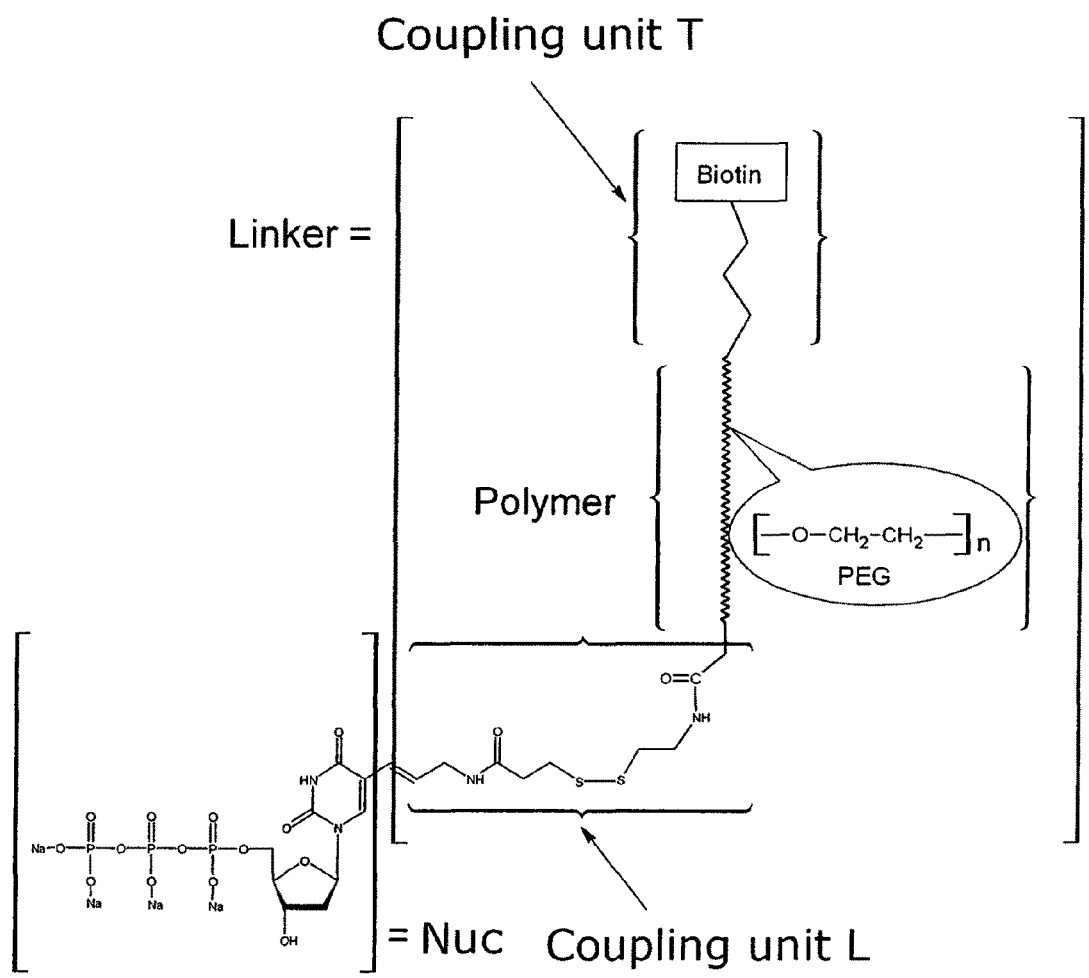
FIG. 31A depicts dUTP-AA-SS-PEG-Biotin.
FIG. 31B shows dUTP-AA-Propionate-S—CO-PEG-Biotin, which represents a further example of nuc-macromolecules with a group cleavable under mild conditions.
Figure 31:
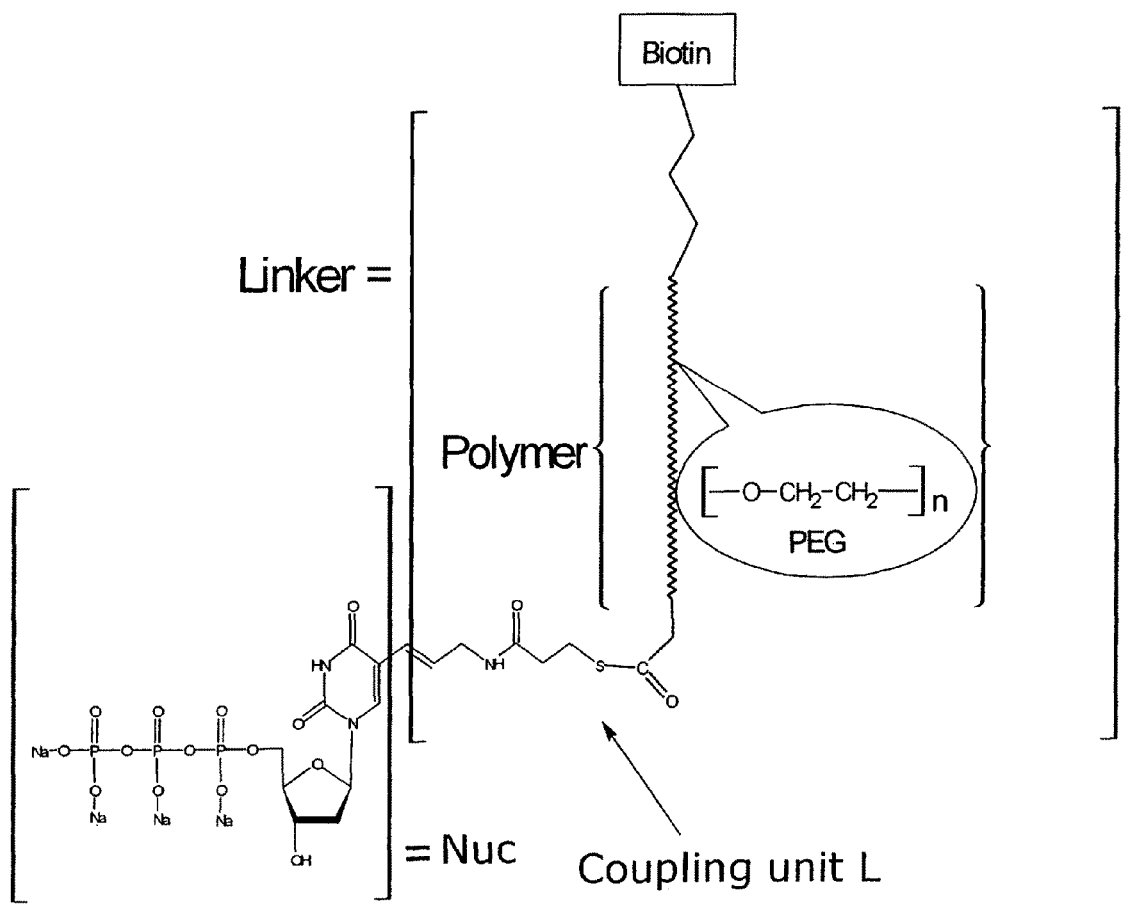

Example 23 dUTP-AA-SS-PEG-Biotin, FIG. 31A

A solution of dUTP-AA-PDTP (50 µl, 30 mmol/l in 50 mmol/l borate, pH 9.5) was added to a solution of Biotin-PEG-Ethyl-SH (100 µl, 10 mmol/l in 50 mM borate, pH 9.5). The reaction mixture was stirred for 18 hours at RT. The separation steps were conducted as described for the synthesis of dUTP-AA-PEG-Biotin (example 19).

This compound comprises a nucleotide functionality and a macromolecular linker. Biotin acts as a coupling unit (T). Macromolecular structures can be coupled to this coupling unit (T), e.g. streptavidin, without loss of the substrate properties of this analog. This nuc-macromolecule acts as a substrate for polymerases. Further macromolecules can be coupled via streptavidin, e.g. enzymes or nucleic acids.

The product is by definition an intermediate stage of a nuc-macromolecule: the linker length is significantly greater than 30 atoms.

Biotin can also be considered as a signal-transmitting marker unit with a low molecular weight.

The linker component can be cleaved off simultaneously with the marker component under mild conditions. This can be advantageous for methods like sequencing by synthesis (Balasubramanian WO 03048387, Tcherkassov WO 02088382, Quake Wool 32930, Kartalov WO02072892), where removal of the marker is necessary after each detection step.

dUTP-AA-Propionate-S—CO-PEG-Biotin (FIG. 31 B) represents a further example of nuc-macromolecules with a group cleavable under mild conditions.

For this synthesis, dUTP-AA-PDTP was freshly purified with an RP-HPLC in water-methanol gradient.

A solution of TCEP (20 µl 100 mmol/l A, pH 8) was added to an aqueous solution of dUTP-AA-PDTP (10 µl, 50 mmol/l). The reaction was allowed to proceed for 10 min at RT. The product of the reaction, dUTP-AA-Propionate-SH, was separated from other reagents on preparative TLC plates, LM 2. Under these conditions the product remains on the start line.

It was eluted from the plate with water and dried and dissolved in 50 µl 50 mmol/l borate buffer pH 8. To the solution obtained, a freshly preparated 2% (w/v) aqueous solution of Biotin-PEG-NHS (50 µl) was added. The reaction was allowed to proceed for 30 min at RT. On completion, the product of the reaction, dUTP-AA-Propionate-S—CO-PEG-Biotin, was separated from the low molecular weight compounds by ultrafiltration, MWCO 3000, and washed five times with 0.5 ml water and, after the last step, dissolved in 50 µl.

The dUTP-AA-Propionate-S—CO-PEG-Biotin obtained by these means can be used by DNA Polymerases, for instance, Klenow fragment Exo-minus or Taq polymerase, for incorporation into the growing strand of nucleic acids.

Further marker components can be coupled to the biotin via streptavidin.

The dUTP-AA-Propionate-S—CO-PEG-Biotin contains a group cleavable under mild conditions, so that the linker with the dye can be cleaved off from the nucleotide. This is of particular interest, for instance, in processes of sequencing by synthesis (Balasubramanian WO 03048387, Tcherkassov WO 02088382, Quake WO0132930, Kartalov WO02072892).

This example shows the general possibility of further nucleotide modifications. Further base-modified nucleotide analogs, e.g., 5-propargylamino-dCTP, 5-amino-propargyl-dUTP, 7-deaza-aminopropargyl-dGTP and 7-deaza-aminopropargyl-dATP can also be modified in a similar way. Ribonucleotides, 2'-deoxyribonucleotides as well as 2',3'-Dideoxyribonucletides can be used (FIGS. 11 to 14).

Example 24

TTP-O-Propionate-SS-PEG-Biotin

A solution of bis-dithio-ethyl-PEG-biotin (100 µl, 0.5 mmol/l, in water) was added to 100 µl of solution of TTP-O-Propionat-SH, 10 mmol/l, in 50 mmol/l borate buffer, pH 9.5, and stirred for 24 h at RT. The purification was done by ultrafiltration with 3,000 MWCO as in example 19.

Examples of the coupling of amino groups to the phosphate residues of nucleotides are described in D. Jameson et al. Methods in Enzymology 1997, v. 278, p. 363. To this amino group a linker component can be coupled. Examples of coupling of linkers to phosphate groups of nucleotides are shown in U.S. Pat. No. 5,981,507. To such a linker further macromolecular linkers comprising a low molecular marker or a low molecular coupling unit or a macromolecular marker can be coupled.

In one embodiment, the macromolecular linker is attached to the phosphate groups, which are coupled to the 5'position of the ribose. The coupling is done preferably to the gamma phosphate group of the nucleotide, whereby ribonucleotides, as well as 2'-deoxyribonucleotides and 2',3-'dideoxyribonucleotides can be used.

In another embodiment, the macromolecular linker is coupled to the 3'-phosphate group of a 5'-nucleoside triphosphate. Synthesis of such derivates is shown in WO 91/06678.

Coupling of Marker Components

Example 25

(dUTP-16 Biotin)4-SA

A solution of streptavidin (200 µl 1 mg/ml, in 50 mmol/l Tris-HCl, pH 8.0) was added to a solution of Biotin-16-dUTP (200 µl, 200 µmol/l, in 50 mmol/l Tris-HCl, pH 8.0). After 1 hour at RT, the (dUTP-16 Biotin)4-SA was separated from non-reacted Biotin-16-dUTP by ultrafiltration, 50,000 MWCO.

A compound was obtained which displays both a nucleotide functionality and a macromolecular marker functionality. The product of the reaction is by definition a conventionally modified nucleotide: the linker length is less than 30 atoms and the marker component is macromolecular. It can be considered as a representative example of conventionally modified nucleotides with a macromolecular marker.

This compound is not accepted by polymerases (e.g., Klenow-Exo-minus polymerase and terminal transferase) as a substrate. The modification leads to the loss of substrate properties (see example 34B).

Properties of the biotin streptavidin linkage are described in, e.g Gonzalez et al. Journal Biolog. Chem. 1997, v. 272, p. 11288.

Example 26

(dUTP-16-Biotin)4-SA-Cy2

The coupling of dUTP-16-Biotin to SA-CY2 was carried out as described for (dUTP-16 Biotin)4-SA.

This compound acts as an equivalent to the compound described in example 25, in which streptavidin has fluorescent labeling for the purpose of visualisation.

Example 27 dCTP-PA-SS-Oligo-dT30

Synthesis was conducted as described for dUTP-M-SS-MEA-Cy3. To dCTP-PA-PDTP (100 µl, 20 mmol/l), Oligo-dT30-3'-SH (MWG-Biotech) was added (final concentration 200 µmol/l) and was stirred for 18 h at RT, pH 9. Separation was accomplished by ultrafiltration with 3,000 MWCO.

The product of the reaction is by definition a conventionally modified nucleotide: the linker length is less than 30 atoms and the marker component is macromolecular. This compound is not accepted by polymerases (e.g., Klenow Exo-minus polymerase and terminal transferase) as a substrate. The modification of the nucleotide part leads to abolition of the substrate properties.

Example 28

(dUTP-M-PEG-Biotin)4-SA-Cy2 and (dUTP-M-PEG-Biotin)4-SA, FIG. 32

The coupling of dUTP-AA-PEG-Biotin to SA-CY2 or to SA was carried out as described for (dUTP-16 Biotin)4-SA. To streptavidin (200 µl, 1 µg/µl) a solution of dUTP-AA-PEG-Biotin (approx. 1 mmol/l, 10 µl) was added and stirred at RT for 1 h. Then the product was separated by ultrafiltration, 50,000 MWCO, from the non-coupled dUTP-AA-PEG-Biotin and the product was washed two times with water.

A part of the (dUTP-AA-PEG-Biotin)4-SA-Cy2 obtained was modified with Cy3-NHS: (dUTP-AA-PEG-Biotin)4-SA-Cy2 (50 µl) was dissolved in 50 mmol/l borate, pH 8.5, up to a concentration of 1.4 µg/µl, and after that Cy3-NHS was added. The final concentration of Cy3 amounted to 10 mmol/l. The reaction was carried out for 1 h at RT. The product, (dUTP-AA-PEG-Biotin)4-SA-Cy2/Cy3, was separated by ultrafiltration with 30,000 MWCO.

Thereby, a nuc-macromolecule was produced that comprises very few free amino groups on the marker part.

A compound was obtained which comprises a nucleotide functionality, a long macromolecular linker and a macromolecular marker component. The product of the reaction is by definition a nuc-macromolecule: the linker length is significantly greater than 30 atoms and the marker component is macromolecular. It can be considered as a representative example of nuc-macromolecules.

This compound is accepted by polymerases (e.g., Klenow Exo-minus polymerase and terminal transferase) as a substrate (see examples 34, 35).

Other compounds having a long linker and comprising a biotin molecule can also be used similarly in synthesis (see examples 20, 22, 23, 24).

Example 29

(dUTP-AA-PEG-Biotin)4-SA-alkaline phosphatase (FIG. 33) and (dUTP-AA-PEG-Biotin)4-SA-QDot (FIG. 34).

The coupling of dUTP-AA-PEG-Biotin to SA-AP or QDot was carried out as described for (dUTP-16 Biotin)4-SA.

In the case of QDot, nuc-linker parts are arranged on the surface of the QDots.

A compound was obtained which comprises a nucleotide functionality, a long macromolecular linker and a macromolecular marker component with an enzyme or Q-Dots.

The product of the reaction is by definition a nuc-macromolecule: the linker length is significantly greater than 30 atoms and the marker component is macromolecular. This compound is accepted by polymerases (e.g., Klenow Exominus polymerase and terminal transferase) as a substrate.

Other compounds that have a long linker and comprise a biotin molecule can also be used similarly in synthesis (see examples 20, 22, 23, 24).

Example 30

(dUTP-AA-PEG-biotin)2-(dT31-TEG-biotin)2-SA-CY2, FIG. 35A

The coupling of dUTP-AA-PEG-biotin to SA-CY2 was carried out like described for (dUTP-16-biotin)4-SA:

dT31-3'-TEG-biotin (MWG Biotech) (80 µl, 80 µmol/l) was added to 100 µl of a solution of streptavidin-Cy2 (20 µmol/l, 1.2 mg/ml, in Tris-HCl, 50 mmol/l, pH 8) and incubated for 10 min at RT. (TEG is a short linker between biotin and dT31). Then, a solution dUTP-AA-PEG-biotin (100 µl, 50 µmol/l, in 50 mmol/l Tris-HCl, pH 8.0) was added. After 10 min at RT, (dUTP-AA-PEG-biotin)2-(dT31-TEG-biotin) 2-SA-CY2 was purified by ultrafiltration, 50,000 MWCO.

The substance comprises a nucleoside triphosphate functionality and macromolecular marker functionalities (oligo-dT31). The oligo-dT31 consists of nucleoside monophosphates, which, however, are not participating in the enzymatic reaction and have only a signal-transmitting function. Complementary nucleic acids, having a signal-giving function, can be hybridized to such an oligonucleotide (FIG. 35B). (General rules for hybridization of nucleic chains are known to the person skilled in the art, Anderson "Nucleic Acid Hybridization", 1999).

The product of the reaction is, by definition, a nuc-macromolecule: the linker length is significantly longer than 30 atoms, the marker component is macromolecular. Polymerases (e.g., Klenow-exo minus polymerase and terminal transferase) accept this compound as a substrate.

This derivative can be coupled, for instance, to poly-dA or poly-A (e.g., with a medium length of 260 NTs, Amersham Bioscience) by hybridization. One single as well as several (dUTP-AA-PEG-biotin)2-(dT31-biotin)2-SA-CY2 molecules can be coupled to a poly-dA molecule, see FIG. 5. The ratio is determined by the concentration ratios. Other oligonucleotides, such as oligonucleotides labeled with dyes, can also be coupled together with (dUTP-AA-PEG-biotin)2-(dT31-biotin)2-SA-CY2 to the same strand of the poly-dA or poly-A, wherein the ratios between various molecules are variable. Thus, it is possible to produce a polyfunctional nuc-macromolecule. A major advantage of such a nuc-macromolecule consists of easily cleavable macromolecular labeling: labeled oligonucleotides hybridized to poly-dA or poly-A strands can be detached via denaturation. The Tm of these oligonucleotides can be adjusted by an appropriate choice of the length of the labeled oligonucleotides for the respective requirements of the reversible labeling. The rules for the Tm calculation are known to the person skilled in the art ("Molecular-Cloning", J. Sambrook, Vols. 1-3, 2001). For instance, $dT_{25}$-oligonucleotides labeled with a Cy3-molecule can be coupled to the poly-dA.

By using RNA, e.g. poly-A for the bonding of several (dUTP-AA-PEG-biotin)2-(dT31-biotin)2-SA, the cleavage can be accomplished by an RNase.

Because streptavidin has 4 binding sites for biotin, the result is a mixture of nuc-macromolecules in which the 4 binding sites are differently occupied. This mixture can be separated by different means. One possibility consists of isolating nuc-macromolecules that carry at least one oligo-dT31, by absorption on an anion exchanger (e.g., a DEAE cellulose column) for example. Gel electrophoresis is also suitable for separating single derivatives.

Longer nucleic acid chains comprising a biotin molecule such as poly-dA-biotin, produced by a terminal coupling of ddUTP-18-biotin in a TdT-dependent reaction ("Molecular-Cloning", J. Sambrook, Vols. 1-3, 2001) for example, can be coupled to the streptavidin in a similar manner, so that molecules with an average composition of $(dUTP-AA-PEG-biotin)_N$-$(nucleic\ acid\ chains-biotin)_M$-SA are produced. Single-stranded as well as double-stranded nucleic acid chains can be coupled. The length of the coupled nucleic acid chains can range between 10 and 100, 100 and 1000 nucleotides.

The hybridized oligonucleotides carrying a dye can also be covalently bonded to the poly-dA strand by crosslinking.

Also other compounds having a long linker and comprising a biotin molecule can similarly be used in the synthesis, see Examples 20, 22, 23, 24.

Example 31

(dUTP-AA-SS-PEG-biotin)4-SA and (dUTP-AA-SS-PEG-biotin)4-SA-Cy2, FIG. 36

The coupling of dUTP-AA-SS-PEG-biotin to SA or to SA-CY2 was carried out as described for (dUTP-AA-PEG-biotin)4-SA. Streptavidin and dUTP-AA-SS-PEG-biotin were used as educts.

The obtained compound comprises a nucleotide functionality, a long macromolecular linker and a macromolecular marker component. The linker component and the marker component can be cleaved from the nuc-component under mild conditions.

The product of the reaction is, by definition, a nuc-macromolecule: the linker length is significantly longer than 30 atoms, the marker component is macromolecular. It can be considered representative for nuc-macromolecules carrying a bond in the linker component cleavable under mild conditions.

Polymerases (e.g., Klenow-exo minus polymerase and terminal transferase) accept this compound as a substrate, see Example 34.

Example 32 dCTP-PA-PEG-maleimide-S-oligo-dT30, FIG. 37A

A solution of 3'-SH-oligo-dT30 (100 µl, 200 µmol/l, in water) was added into a solution of dCTP-PA-PEG-maleimide (100 µl, 5 mmol/l, in 50 mmol/l borate buffer, pH 9.5) and stirred at RT for 48 h. The product was cleaned by means of preparative gel electrophoresis, 12% polyacrylamide gel.

The substance comprises a nucleoside triphosphate functionality and macromolecular marker functionalities (oligo-dT30). The oligo-dT30 consists of nucleotides which do not take part, however, in the enzymatic reaction and have only a signal-transmitting function. Complementary nucleic acids having a signal-giving function can be hybridized to such an oligonucleotide (FIG. 37B). (General rules for the hybridization of nucleic acids are known to the person skilled in the art, Anderson "Nucleic Acid Hybridization", 1999).

The nucleotide is, by definition, a nuc-macromolecule: the linker length is significantly longer than 30 atoms, the marker component is macromolecular.

Polymerases (e.g., Klenow-exo minus polymerase and terminal transferase) accept this compound as a substrate.

This example shows a general possibility for making further modifications to nucleotides. Other base-modified nucleotide analogs, e.g., 5-allylamino-dUTP, 5-amino-propargyl-dUTP, 7-deaza-aminopropargyl-dGTP and 7-deaza-aminopropargyl-dATP can be also modified as described above. Ribonucleotides, 2'-deoxyribonucleotides as well as 2',3'-dideoxyribonucletides can be used, FIGS. 11 to 14.

Figure 37:
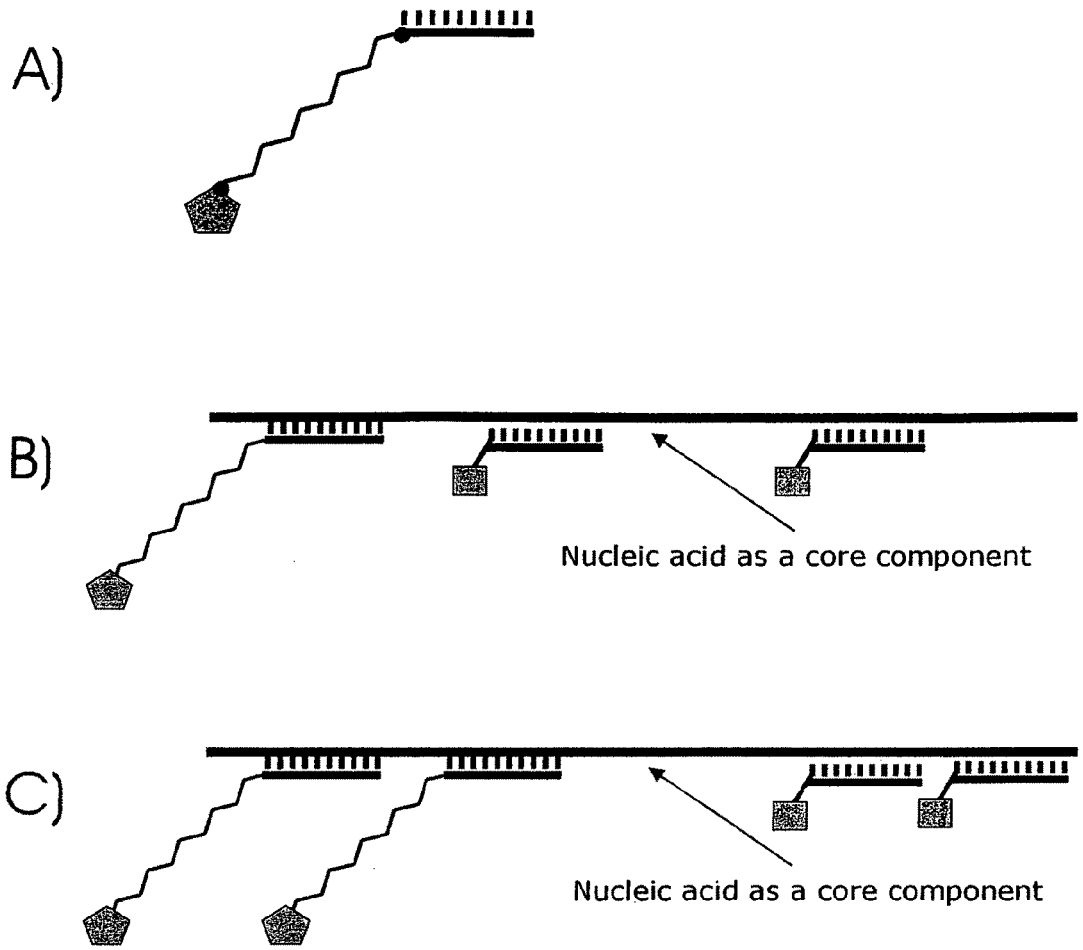
FIG. 37 C shows that a nuc-macromolecule with linearly arranged nuc-linker components is obtained by a process of the disclosure of the invention.

By adding poly-dA or poly-A, it is possible to couple several dCTP-PA-PEG-maleimide-S-oligo-dT30 molecules, e.g., 10 to 20, to one nuc-macromolecule. A nuc-macromolecule with linearly arranged nuc-linker components is thereby obtained (FIG. 37 C).

Example 33

(dCTP-PA-PEG-maleimide-S)n-polylysine-(Cy3)m
Educts: dCTP-PA-PEG-maleimide
(HS-propionate)m-polylysine-(Cy3)n, n=10 to 15, m=3 to 9, polylysine 10,000-20,000

A solution of (HS-propionate)m-polylysine-(Cy3)n (20 µl, approx. 1 mmol/l, in water) was added to a solution of dCTP-PA-PEG-maleimide (100 µl, 5 mmol/l, in 50 mmol/l borate buffer, pH 9.5) and stirred at 40° C. for 18 h. The product was purified by ultrafiltration, 30,000 MWCO.

The obtained compound comprises a nucleotide functionality, a long macromolecular linker and a macromolecular marker component. Several nuc-components are coupled per each nuc-macromolecule. The product of the reaction is, by definition, a nuc-macromolecule: the linker length is significantly longer than 30 atoms, the marker component is macromolecular.

Polymerases (e.g., Klenow-exo minus polymerase and terminal transferase) accept this compound as a substrate.

Other combinations of nuc-components, linker components and marker components are obvious to the person skilled in the art.

Comparison of Substrate Properties of Some Representatives of Nuc-macromolecules with Conventionally Modified Nucleotides.

Substrate properties of the nuc-macromolecules for polymerases and terminal deoxy-nucleotidyl-transferase (TdT) were compared to the properties of the conventionally modified nucleotides in a labeling reaction. General principles of labeling reactions are shown in "Molecular-Cloning", J. Sambrook, Vols. 1-3, 2001, ISBN 0-87969-576-5.

Example 34

Substrate Properties of Nuc-macromolecules or Conventionally Modified Nucleotides Towards Polymerases This example is not intended to limit the possible labeling reactions, but merely to point out differences in the substrate properties.

Both self-synthesized and commercially available modified nucleotides dUTP-Cy3 (Amersham) and dUTP-16 biotin (Roche) were used in the reactions. Unmodified dNTPs (dATP, dGTP, dTTP, dCTP) were purchased from Roth.

Both short oligonucleotides and poly-dA acted as templates. Primers and oligonucleotides were synthesized by MWG Biotech.

Reactions were carried out in 20 mmol/l of Tris buffer, pH 8.5, 5 mmol/l $MgCl_2$, 10% glycerin. The concentrations of the primers amounted to 1 µmol/l, of the oligonucleotides, 1 µmol/l, and the concentration of poly-dA was 0.1 µg/µl (for the concentration ratios for the solid phase, see below). Klenow exo minus was used a polymerase (Amersham) at concentration of 1 Unit/100 µl. The concentrations of nucleotides amounted to 20 µmol/l for conventionally modified nucleotides and 5 µmol/l for nuc-macromolecules. Unmodified nucleotides were used in concentrations of 50 µmol/l.

First, primers were hybridized to the respective template: The reaction mixture without polymerase was heated up to 75° C. and was cooled down to 37° C. over 5 min. Then, the polymerase was added. All reactions were carried out at 37° C. for 1 h. The reactions were stopped by adding EDTA (final concentration 10 mmol/l).

After the reaction had stopped, streptavidin was added to some reaction mixtures up to a final concentration of 1 mg/ml and the reaction mixture was incubated at 37° C. for another 10 min. The already-incorporated nucleotides comprising biotin can thereby react with streptavidin and thereby link streptavidin and oligonucleotide. These experiments are suitable as a control for the mobility properties of modified primers.

Mercaptoethanol was added to the designated reaction mixtures (up to 20 mmol/l final concentration) and the respective mixtures were incubated at 37° C. for 10 min. For some mixtures, mercaptoethanol was added during the reaction and, for others, after the reaction.

The reaction was analyzed by means of denaturing gel electrophoresis, 20% polyacrylamide-gel, 50 mmol/l Tris-HCl, pH 8.7, as described in "Gel electrophoresis of nucleic Acids", Ed. D. Rickwood, 1990. For the denaturing of the samples, a higher temperature, rather than 7 M urea, was used during the gel electrophoresis (60° C.). The electrophoresis was carried out in BioRad gel chambers (Protean 3), at 200 V, for approx. 1 h. The visualization was performed using the UV-vis gel-documentation equipment (BioRad).

Figure 38:
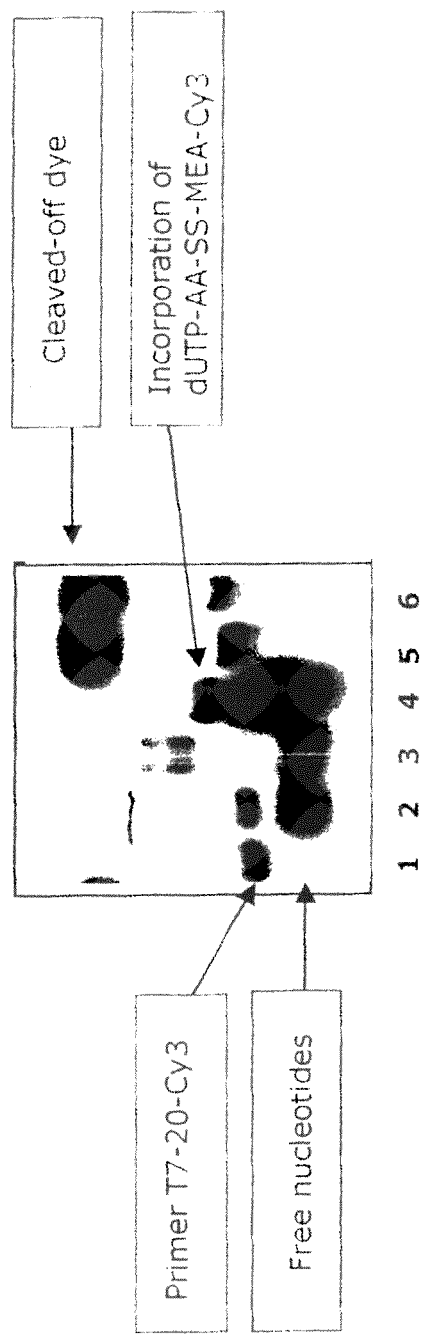
FIG. 38 illustrates the incorporation and cleavage of a conventionally modified nucleotide (dUTP-AA-SS-MEA- Cy3) and shows that even slight changes in the analog structure, for instance, doubling the number of the dyes which are coupled to a nucleotide, can change the substrate properties of the nucleotides.

Example 34A, FIG. 38

Illustration of the Incorporation and Cleavage of a Conventionally Modified Nucleotide (dUTP-AA-SS-MEA-Cy3)
Sequences:

```
Primer:
Primer-T7-20-5'-Cy3:
5'-Cy3-TAATACGACTCACTATAGGG-3'

Template:
Oligonucleotide
Oligo 1:
5'-AGTTTTAGTTTTACCCTATAGTGAGTCGTATTA-3'
```

The primer binding site is underlined.
Legend:
Traces 1-6:
1) Only PrimerT7-20-Cy3+Oligo 1
2) PrimerT7-20-Cy3+Oligo 1+dCTP-Cy3+dATP+dGTP+polymerase
3) PrimerT7-20-Cy3+Oligo 1+dCTP-Cy3+dATP+dGTP+dTTP+polymerase 4) PrimerT7-20-Cy3+Oligo 1+dUTP-AA-SS-MEA-Cy3+ polymerase
5) After 1 h, mercaptoethanol was added to an aliquot of the reaction mixture 4 and incubated for another 10 min. This resulted in a cleavage of the labeling.
6) After 10 min, dGTP was added to an aliquot of the reaction mixture 5 dATP and incubated at 37° C. for 30 min.

As can be seen, dUTP-AA-SS-MEA-Cy3 is incorporated by the polymerase (trace 4). The dye can be cleaved off from the primer (trace 5) (as can be seen, the band is shifted because of the smaller size of the oligonucleotide). Finally, other nucleotides can be incorporated (trace 6).

A reaction mixture with dUTP-M-SS-TEAE-(Cy3)2, carried out in a similar way, did not result in incorporation of the nucleotide analogs into the primer.

This example shows that the even slight changes in the analog structure, for instance, doubling the number of the dyes which are coupled to a nucleotide, can change the substrate properties of the nucleotides.

Figure 39:
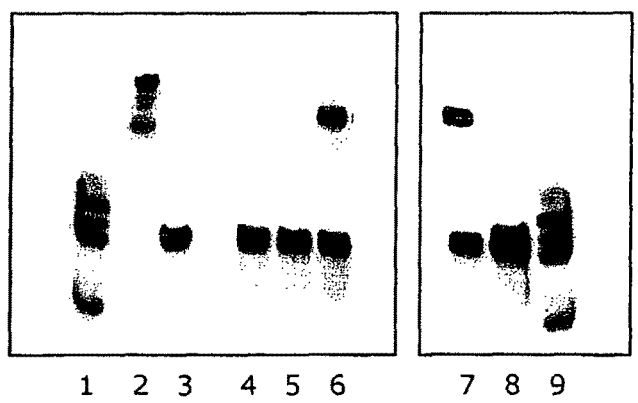
FIG. 39 shows a comparison of substrate properties of a conventionally modified nucleotide with a macromolecular marker and a nuc-macromolecule.

Example 34B, FIG. 39

Comparison of substrate properties of a conventionally modified nucleotide with a macromolecular marker and a nuc-macromolecule
Sequences:
Primer:

```
PrimerdT35-5'-Cy3 (dT35-Cy3):
5'-Cy3-TTTTTTTTTTTTTTTTTTTTTTTTTTTTTTTTTTT-3'
```

Template:
Poly-dA (Amersham), average length 270 nucleotides.
Nucleotides: (dUTP-AA-SS-PEG-biotin)4-SA, (dUTP-16-biotin)4-SA, dUTP-16-biotin
Legend:
Traces 1-9:
1) Ladder: T-7-20-Cy3, dT35-Cy3, dT40-Cy3, dT50-Cy3
2) (dUTP-AA-SS-PEG-biotin)4-SA+dT35-Cy3+poly-dA+ polymerase
3) (dUTP-M-SS-PEG-biotin)4-SA+dT35-Cy3+poly-dA
4) (dUTP-16-biotin)4-SA+dT35-Cy3+poly-dA+polymerase
5) (dUTP-16-biotin)4-SA+dT35-Cy3+poly-dA
6) (dUTP-16-biotin)4-SA-Cy3+dT35-Cy3+poly-dA
Control reaction mixture, traces 7-9:
7) dUTP-16-biotin+dT35-Cy3+poly-dA+polymerase, incubation at 37° C. for 1 h followed by +EDTA to 10 mmol/l final concentration, followed by +Streptavidin, 37° C., 10 min
8) dUTP-16-biotin+dT35-Cy3+poly-dA+polymerase, incubation at 37° C. for 1 h followed by +EDTA to 10 mmol/l final concentration,
9) Ladder: T-7-20-Cy3, dT35-Cy3, dT40-Cy3, dT50-Cy3

A nuc-macromolecule, (dUTP-AA-SS-PEG-biotin)4-SA, is incorporated into the primer (trace 2). After the nuc-macromolecule has been incorporated, the electrophoretic mobility of the labeled primer is greatly changed. Mere presence of nuc-macromolecules has no influence on the primer (trace 3).

A conventionally modified nucleotide, (dUTP-16-biotin) 4-SA, with a macromolecular marker, is not incorporate into the primer (trace 4). In spite of the presence of the polymerase in reaction 4 (trace 4), no differences can be observed between trace 4 and trace 5.

Trace 6 shows the position of the conventionally modified nucleotide with a macromolecular marker, (dUTP-16-biotin) 4-SA-Cy3 (the upper band), and the position of the labeled primer (the lower band).

Trace 7 shows the result of incorporating dUTP-16-biotin followed by a reaction with the streptavidin: Primers labeled with biotin react with streptavidin and change their mobility properties. The unmodified primers maintain their electrophoretic properties.

Trace 8 shows the result of the incorporation reaction of a conventionally modified nucleotide, dUTP-16-biotin. A widened primer band, resulting from the incorporation of dUTP-16-biotin into the primer, can be seen. The extension of primers is limited, because dUTP-16-biotin cannot be successively incorporated indefinitely; an average of approx. 3 dUTP analogs are incorporated, so that the length of primer rises on average to 38 NTs. As expected, the incorporation of conventionally modified nucleotides with a low molecular marker does not lead to a strong change in the electrophoretic mobility of the primer.

In this experiment, properties of the nuc-macromolecules, (dUTP-AA-SS-PEG-biotin)4-SA were compared to those of the conventionally modified nucleotides. It can be clearly seen that the coupling of a macromolecular marker to a commercially obtained dUTP-16-biotin leads to total loss of the substrate properties of the nucleotides. However, polymerase is quite capable of inserting dUTP-16-biotin without macromolecular marker into the primer (traces 7 and 8). The coupling of streptavidin to the biotin after the incorporation reaction leads to the mentioned changes in primer properties.

In contrast, the polymerases can incorporate nuc-macromolecules (dUTP-AA-SS-PEG-biotin)4-SA into the primer without difficulty. The inventors attribute the appearance of several bands in the gel (3 bands) to a multiple incorporation of nuc-macromolecules into the primer.

Figure 40:
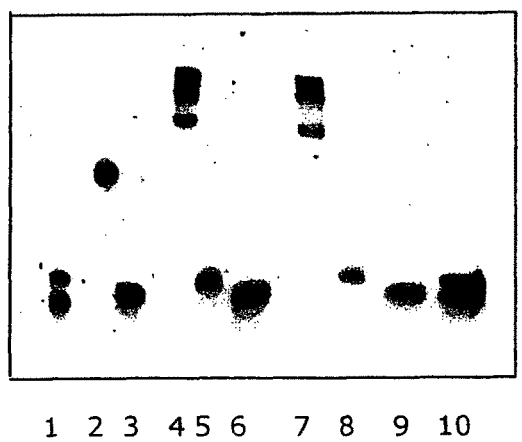
FIG. 40 shows a comparison of substrate properties of nuc-macromolecules using an incorporation reaction in solution and on a solid phase.

Example 34C, FIG. 40

Comparison of substrate properties of nuc-macromolecules, incorporation reaction in the solution and on a solid phase.
Sequences:
Primer: (dT35-Cy3)

```
Primer-dT-35-5'-Cy3:
5'Cy3-TTTTTTTTTTTTTTTTTTTTTTTTTTTTTTTTTTT-3'
```

Template:
Poly-dA (Amersham), average length 270 nucleotides.
Oligo-dA50-3-TEG-biotin (MWG Biotech)
Nucleotides: (dUTP-AA-SS-PEG-biotin)4-SA, (dU-M-PEG-biotin)4-SA
Streptavidin polystyrene particles, 2.17µ, Spherotech Inc, Preparation of Streptavidin Polystyrene Particles (Solid Phase).

Three aliquots were prepared in the same way.

A solution with beads (0.5 ml in the manufacturer's buffer) was briefly centrifuged and bead-pellet was re-suspended in 100 µl of incorporation buffer (20 mmol/l Tris, pH 8.5, 5 mmol/l MgCl$_2$). Next, oligo-dA50-3'-TEG-biotin (100 µl, 50 µmol/l) was added and stirred at RT for 1 h. Oligo-dA molecules bind to the beads during this time. Next, the beads were briefly centrifuged and washed three times with the incorporation buffer. The final volume of the solid phase amounted 100 µl. This quantity of oligo-dA50-solid-phase can hybridize primer-dT-35-Cy3 (2 µmol/l).

The hybridization of primer-dT-35-Cy3 was undertaken for 10 min at 40° C., followed by cooling to RT within 10 min.

All other steps were carried out in identical way for all aliquots.
Legend:
Traces 1-10:
1) Ladder: dT35-Cy3, dT40-Cy3,
Reactions in the Liquid Phase:
2) (dUTP-AA-PEG-biotin)4-SA+dT35-Cy3+poly-dA+ polymerase
3) (dUTP-AA-PEG-biotin)4-SA+dT35-Cy3+poly-dA
4) (dUTP-AA-SS-PEG-biotin)4-SA+dT35-Cy3+poly-dA+ polymerase, incubation at 37° C. for 1 h, then+EDTA
5) (dUTP-M-SS-PEG-biotin)4-SA+dT35-Cy3+poly-dA+ polymerase, incubation at 37° C. for 1 h, then+EDTA, followed by +Mercaptoethanol up to 200 mmol/l (final concentration) for 30 min.
6) (dUTP-AA-SS-PEG-biotin)4-SA+dT35-Cy3+Poly-dA+ EDTA
Reactions on Solid Phase:
7) (dUTP-AA-SS-PEG-biotin)4-SA+dT35-Cy3+oligo-dA50-solid-phase+polymerase, incubation at 37° C. for 1 h, then+EDTA,
8) (dUTP-AA-SS-PEG-biotin)4-SA+dT35-Cy3+oligo-dA50-solid-phase+polymerase, incubation at 37° C. for 1 h, then+EDTA, followed by +mercaptoethanol up to 200 mmol/l (final concentration) for 30 min.
9) (dUTP-AA-SS-PEG-biotin)4-SA+dT35-Cy3+oligo-dA50 solid phase, prior to electrophoresis+EDTA
10) Ladder: dT35-Cy3, dT40-Cy3, The result of the incorporation reaction of nuc-macromolecules is clearly seen in traces 2, 4, 5, 7, 8. The enzymatic labeling reaction works well both in the solution and on the solid phase.

The cleavage of linker components with the bound streptavidin from the primers takes place after mercaptoethanol is added to reactions that have been stopped with EDTA. This leads to recovery of the electrophoretic properties of the primers. The shifting of the primer bands in traces 5 and 8 can be explained by multiple incorporation of nuc-macromolecules into the primer. In fact, the primer bands appear at the level of dT40-Cy3 (see ladder) following the cleavage. This means that up to 5 nuc-macromolecules were incorporated into the primer during the reaction.

Figure 41:
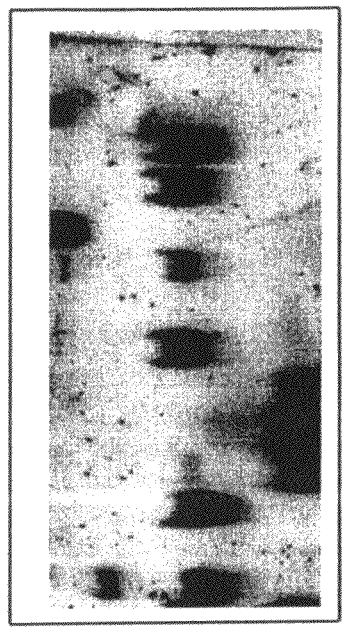
FIG. 41 shows a comparison of the substrate properties of the nuc-macromolecules of the disclosure and conventionally modified nucleotides for terminal transferase (TdT).

Example 35, FIG. 41

Substrate Properties of the Nuc-Macromolecules and Conventionally Modified Nucleotides for Terminal Transferase (TdT)

The reaction was carried out according to the instructions of the kit manufacturer (Roche): For each 50 μl volume, the following was added: 10 μl 5× reaction buffer, 1 μl TdT (25 units), 5 μl 25 mmol/l CoCl2. The primer concentration and nucleotide concentrations were same as in reactions with the polymerase. The reaction was carried out at 37° C. for 2 h.
Primer: Primer-dT$_{35}$-5'-Cy3 (dT35-Cy3), Primer-dT$_{35}$ (dT35)
Legend:
1) (dUTP-M-PEG-biotin)4-SA+dT35-Cy3+TdT
2) (dUTP-M-PEG-biotin)4-SA+dT35-Cy3
3) dUTP-Cy3 (Amersham)+dT35+TdT
4) dUTP-Cy3 (Amersham)+dT35
5) dUTP-16-biotin (Roche)+dT35-Cy3+TdT;
6) Mixture 5; after the stop+streptavidin
7) Streptavidin-Cy2
8) (dUTP-16-biotin)4-SA+dT35-Cy3+TdT
9) (dUTP-16-biotin)4-SA+dT35-Cy3
10) (dUTP-16-biotin)4-SA-Cy2

Two bands can clearly be seen in trace 1, the band in the middle corresponding to the dT35-Cy3, the upper band corresponding to the reaction product: nuc-macromolecule was incorporated into dT35 by TdT. Trace 2 is a negative control. In trace 3, it is possible to see the result of labeling dT35 with the conventional nucleotide dUTP-Cy3. Trace 4 is the negative control. In trace 5, the result of the coupling dUTP-16-biotin to the dT35-Cy3 can be poorly recognized. However in trace 6, a weak band, which corresponds to the result of the reaction of the dUTP-16-biotin-modified primer with streptavidin, can be seen in the upper area. Trace 7 shows the position of the modified streptavidin. In traces 8 and 9, only one band, which corresponds to the dT35-Cy3, can be seen in the center of the gel; in the upper area of the gel, there is no visible band, clearly indicating that TdT does not incorporate conventionally modified nucleotides with a macromolecular marker. Trace 10 shows the position of the (dUTP-16 biotin) 4-SA-Cy2 in the gel.

Figure 42:
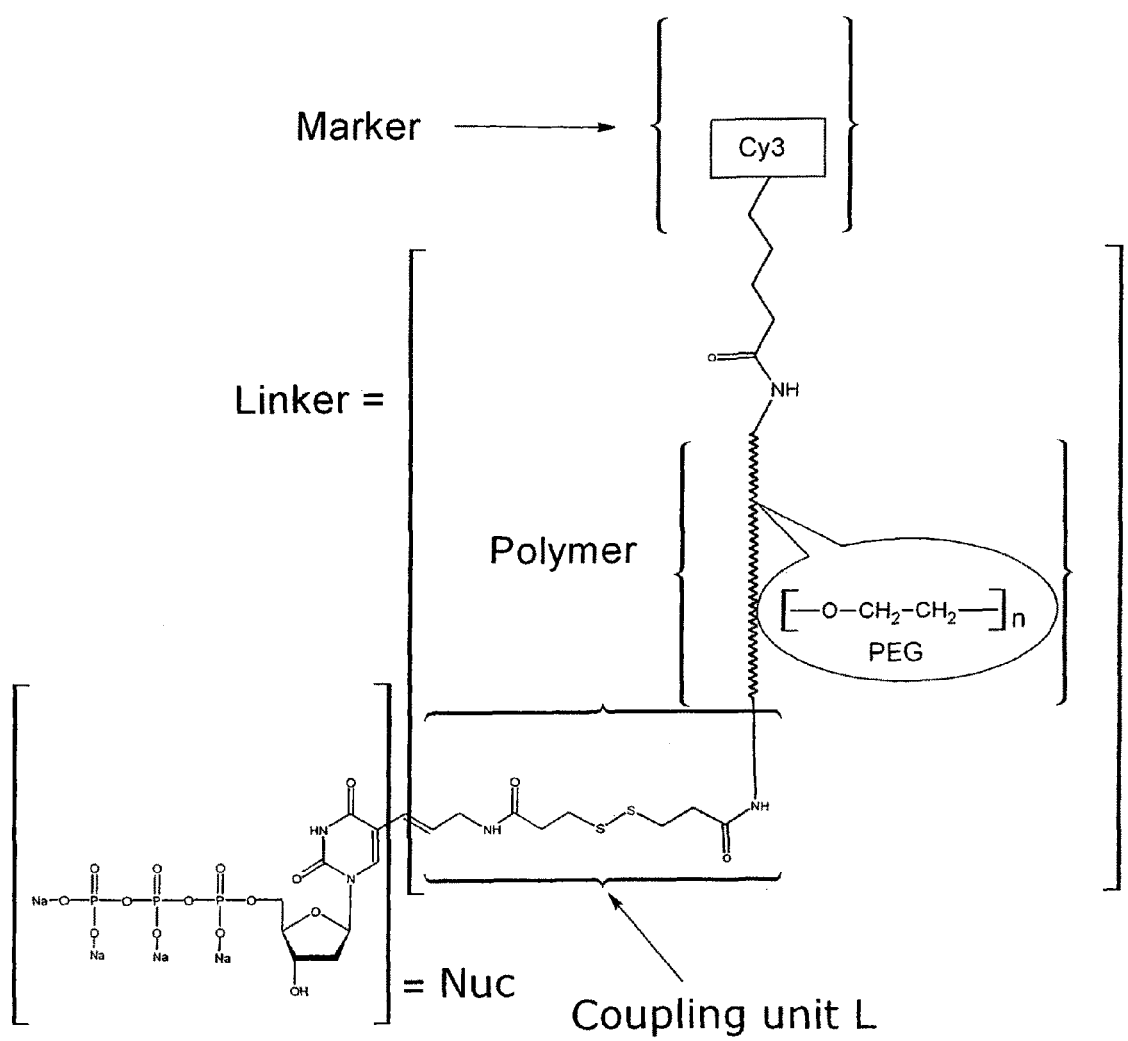
FIG. 42A is a schematic of dUTP-AA-SS-PEG-Cy3.
FIG. 42B is a schematic of $NH_2$-PEG-Cy3.
Figure 42:
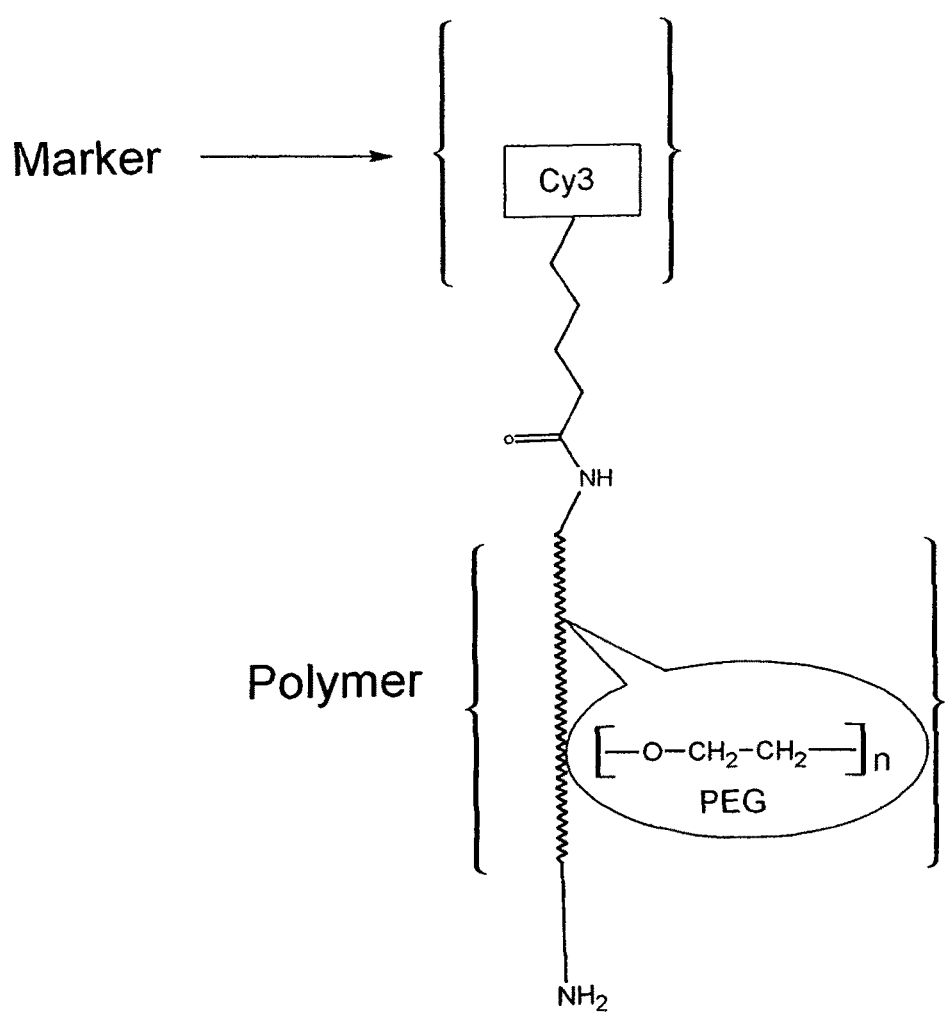

Example 36 dUTP-AA-SS-PEG-Cy3, FIG. 42 A

First, SH-PEG-Cy3 was synthesized. Cy3-NHS (Amersham-Bioscience) was added to a solution of diamine-PEG (6 kDa, Fluka) (200 μl, 10 mmol/l, in 50 mmol/l borate buffer, pH 8) up to final concentration of 15 mmol/l. The reaction was carried out at RT for 30 min. Next, NH$_2$-PEG-Cy3 (FIG. 42 B) was separated from dye residues by ultrafiltration with MWCO 3000, washed 3 times with 1 ml 50 mmol/l borate buffer, pH 8, and dissolved in 200 μl of 50 mmol/l borate buffer, pH 8.

PDTP-NHS was added to this solution up to final concentration of 50 mmol/l. The reaction was carried out at RT for 30 min. Next, a solution of NH$_4$HCO$_3$ (50 μl, 1 mol/l, pH 8), was added, and the reaction mixture was incubated for another 60 min. A solution of TCEP (100 μl, 1 mol/l, pH 8) was added to the reaction mixture to reduce the disulfide bonds. After 5 min at RT, the product of the reaction, the SH-PEG-Cy3, was separated from the low-molecular compounds by ultrafiltration with MWCO 3000, was washed 5 times with 1 ml 50 mmol/l Tris-HCl buffer, pH 7, and dissolved in 200 μl of 50 mmol/l Tris-HCl, pH 7. The pH value was adjusted to 9.0 with 1 mol/l NaOH immediately before the coupling of the nucleotide part.

Coupling of the SH-PEG-Cy3 to the nucleotide part:
A solution of SH-PEG-Cy3 (100 μl, in 50 mmol/l Tris-HCl, pH 9.0) was added to 100 μl of 20 mmol/l dUTP-M-PDTP in 50 mmol/l borate buffer, pH 9. The reaction was allowed to proceed at RT for more than 30 min. The product of the reaction was separated from low-molecular components by ultrafiltration with MWCO 3000, was washed 5 times with 1 ml of 50 mmol/l Tris-HCl buffer, pH 7, and was dissolved in 200 μl of 50 mmol/l Tris-HCl, pH 7.

The dUTP-AA-SS-PEG-Cy3 obtained in this manner can be incorporated into the growing strand of nucleic acids by polymerases, e.g. Klenow fragment exo minus or Taq-polymerase.

The dUTP-M-SS-PEG-Cy3 contains a group that is cleavable under mild conditions, so that the linker with the dye can be cleaved off from the nucleotide. This is, for instance, of particular interest for processes for sequencing by synthesis (Balasubramanian WO 03048387, Tcherkassov WO 02088382, Quake WO0132930, Kartalov WO02072892).

This example shows a general possibility for making further modifications to nucleotides. Further base-modified nucleotide analogs, e.g., 5-propargylamino-dCTP, 5-propargylamino-dUTP, 7-deaza-aminopropargyl-dGTP and 7-deaza-aminopropargyl-dATP can also be modified as described above. Ribonucleotides, 2'-deoxyribonucleotides as well as 2',3'-Dideoxyribonucletide can be used, FIGS. 11 to 14.

Figure 43:
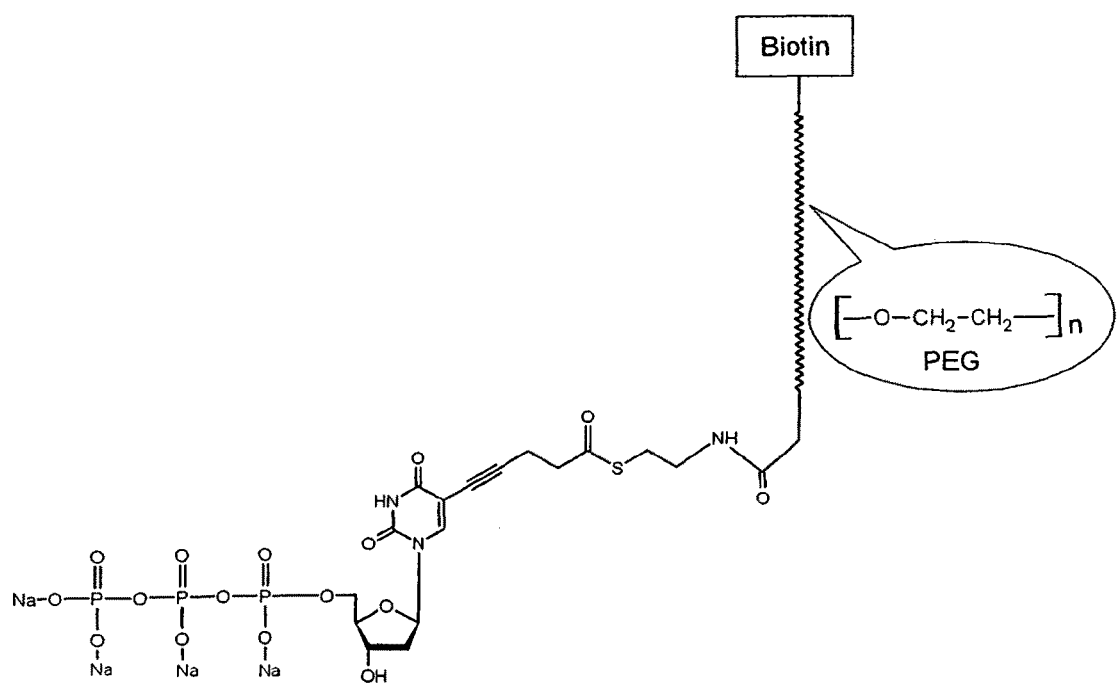
FIG. 43 is a schematic of dUTP-R—CO—S-PEG-biotin.

Example 37 dUTP-R—CO—S-PEG-biotin FIG. 43

Figure 44:
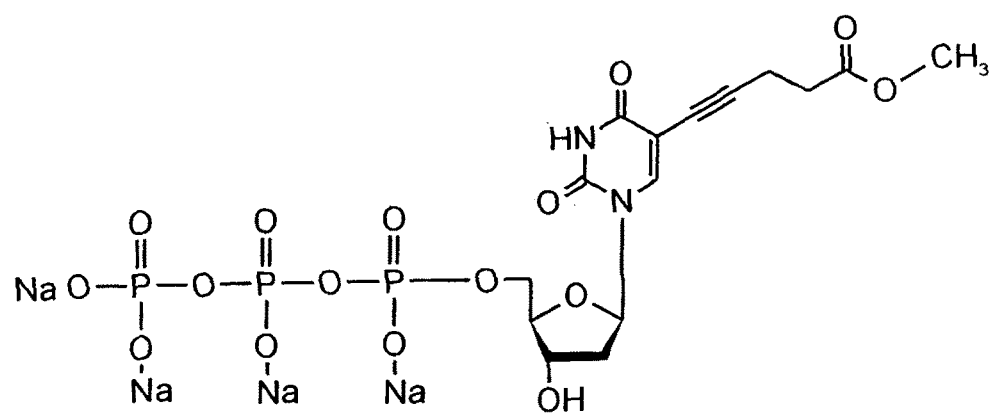
FIG. 44 depicts dUTP-R—COOCH$_3$.

The dUTP-R—COOCH$_3$ (FIG. 44) was synthesized in similar way as specified (Heike A. Held, Abhijit Roychowdhury, and Steven A. Benner, Nucleosides, Nucleotides & Nucleic Acids, v. 22, p. 391-404 (2003)). The Triphosphate synthesis was conducted according to T. Kovacs, L. Ötvös, Tetrahedron Letters, v. 29, p. 4525-4588 (1988)). 5-iodo-2'-deoxyuridine (500 mg, 1.41 mmol) was suspended in 10 ml of anhydrous DMF in a nitrogen atmosphere at RT and was stirred for 10 min. Then, tetrakis(triphenylphosphine)palladium (0) (160 mg, 0.14 mmol) was added. After another 10 min, 400 µl triethylamine, (480 mg, 4.28 mmol) pent-1-in acid methylester and copper (I) iodide (55 mg, 0.29 mmol) were added successively. After 15 h, the reaction mixture was concentrated in the rotation evaporator and the red oil obtained was separated by means of silica gel chromatography (dichloromethane:methanol=20:1). This produces 400 mg (84%) of product. After triphosphorylation, dUTP-R—COOCH$_3$, was obtained.

Other bases, like cytosine, adenosine and guanosine derivatives, can be also modified in a similar way using the Pent-1-in acid methylester (dissertation "Synthese basenmodifizierter Nukleosidtriphosphate und ihre enzymatische Polymerisation zu funktionalierter DNA", Oliver Thum, Bonn in 2002).

Figure 45:
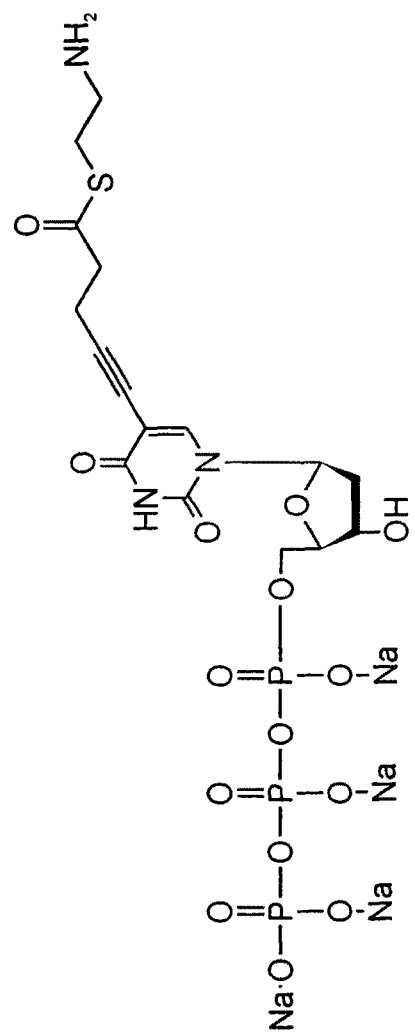
FIG. 45 depicts dUTP-R—CO—S—CH2—CH2—NH2, which has a thioester group that is cleavable under mild conditions and can be modified on the amino group of the linker.

Further modification is performed on the dUTP-R—COOCH3:

A solution of the mercaptoethanolamine (100 µl, 1 mol/l, pH 9) is added to 100 µl of a solution of dUTP-R—COOCH3 (50 mmol/l, in 50 mmol/l borate buffer, pH 9) and is stirred at 40° C. for 3 h. The product of the reaction, the dUTP-R—CO—S—CH2-CH2-NH2 (FIG. 45), is separated from the excess of mercaptoethanolamine on DEAE-cellulose in the borate buffer 10 mmol/l and eluted from the column with 0.3 mol/l of NaCl.

This nucleotide has a thioester group that is cleavable under mild conditions and can be modified on the amino group of the linker.

Figure 46:
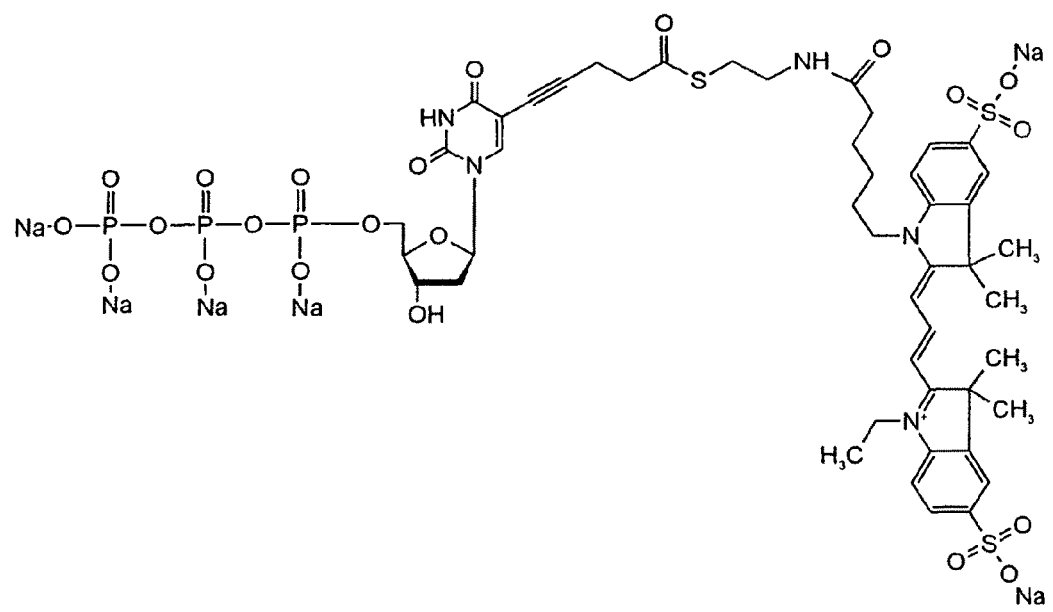
FIG. 46 depicts dUTP-R—CO—S—CH$_2$—CH$_2$—NH—R-Cy3.

Further modifications can be carried out on this amino group. For instance, a dye can be coupled to it: Synthesis of dUTP-R—CO—S—CH$_2$—CH$_2$—NH—R-Cy3 (FIG. 46)

Cy3-NHS was added to a solution of the dUTP-R—CO—S—CH$_2$—CH$_2$—NH$_2$ (100 µl, 10 mmol/l, in 50 mmol/l borate buffer, pH 9) up to a concentration of 15 mmol/l. The reaction was allowed to proceed at RT for more than 30 min. Next, the Cy3-modified nucleotide was purified on a silica gel plate and RP-18 column similarly as described in Example 15. Such a nucleotide can be used as a reversible terminator in a method for sequencing nucleic acids (Tcherkassov WO 02088382). The cleavage of the thioester bond can be accomplished, for instance, by adding 100 mmol/l of mercaptoethanol in 50 mmol/l borate buffer, pH 9.

A long linker with a low molecular marker can be also coupled to the amino group of the dUTP-R—CO—S—CH$_2$—CH$_2$—NH$_2$, similarly as in example 19. The obtained dUTP-R—CO—S—CH$_2$—CH$_2$—NH-PEG-biotin can serve as an intermediate product for a nuc-macromolecule.

Figure 47:
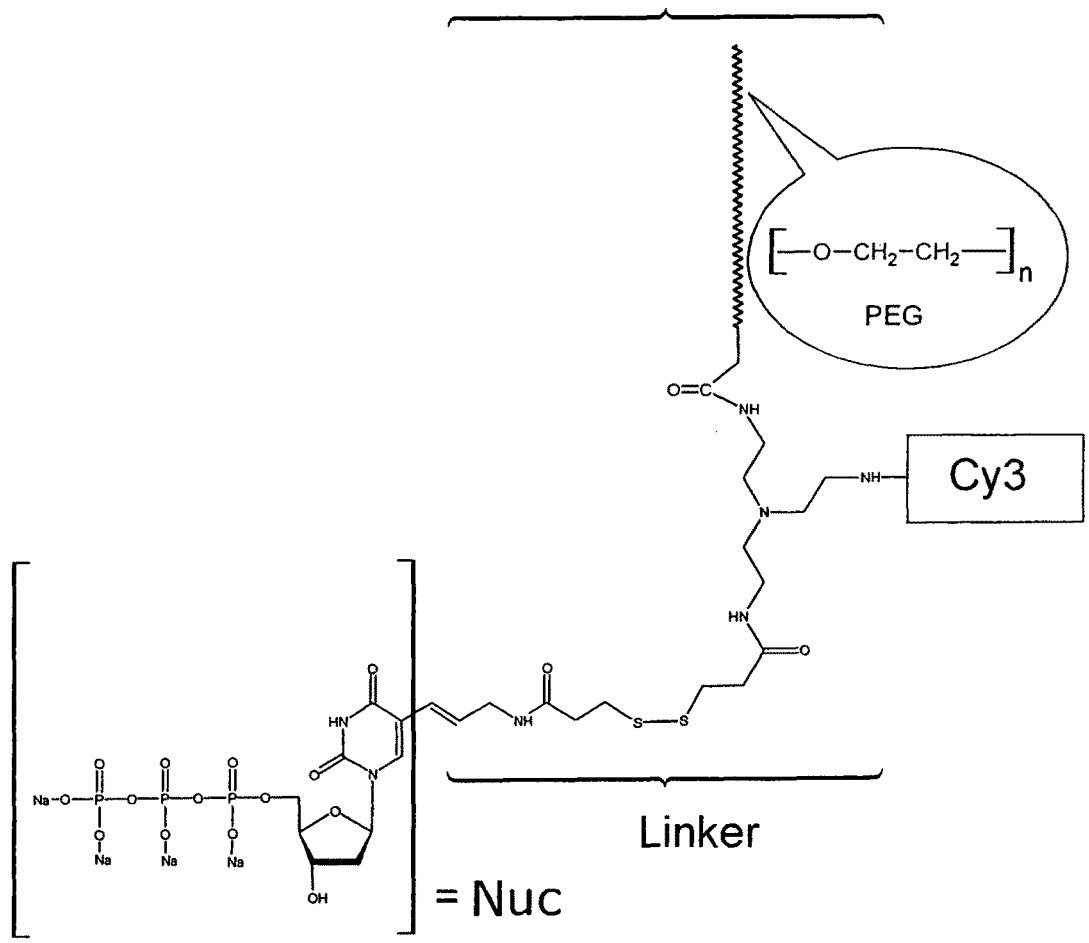
FIG. 47 depicts dUTP-AA-SS-propionate-TEAE-Cy3-PEG.

Example 38 dUTP-AA-SS-propionate-TEAE-Cy3-PEG (FIG. 47)

This derivative can be obtained from dUTP-AA-SS-propionate-TEAE-Cy3 (see example 17) by modifying the amino group in the linker with an mPEG-SPA, e.g., 5000 Da. The modification conditions are similar to those in example 19. This molecule comprises a long linker and can be used in the method according to the invention for rapid purification of the modified nucleotides prior to their use in labeling reactions. A filter with MWCO of 3000 can be used to separate labeled nucleotides from unlabeled nucleotides.

Example 39

Figure 48:
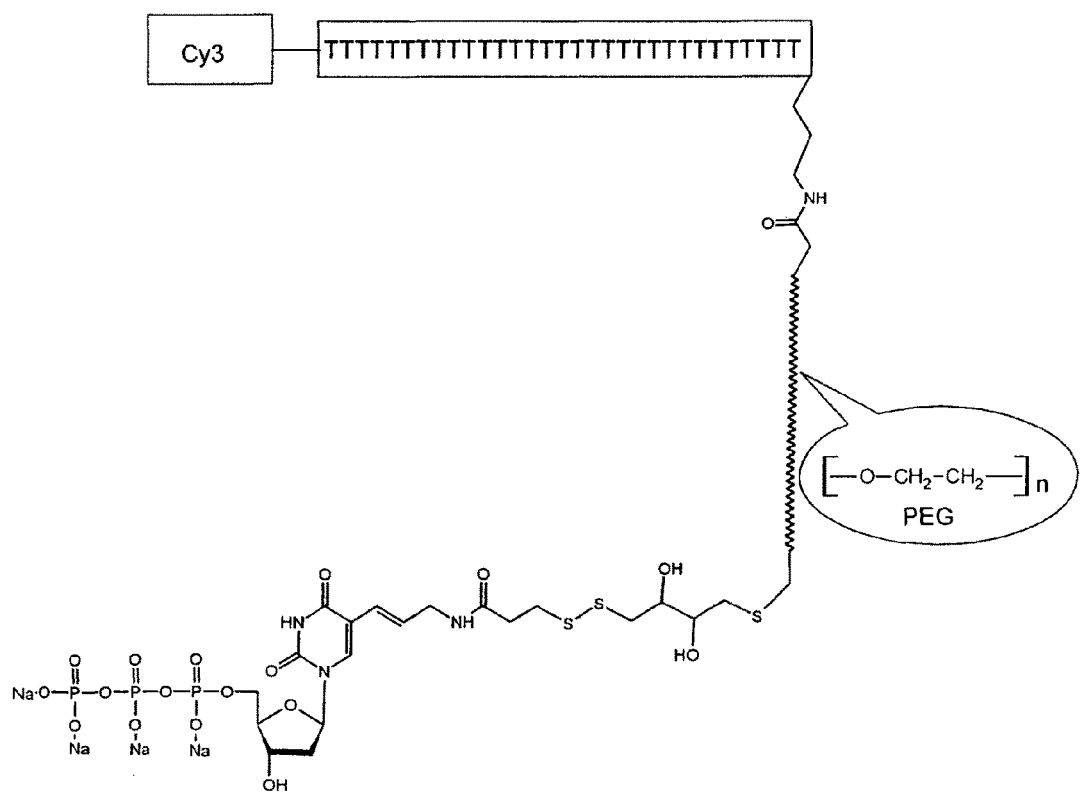
FIG. 48 depicts dUTP-AA-SS—R-PEG-oligo-dT31-Cy3.

Synthesis of dUTP-AA-SS—R-PEG-oligo-dT31-Cy3 (FIG. 48)

Figure 49:
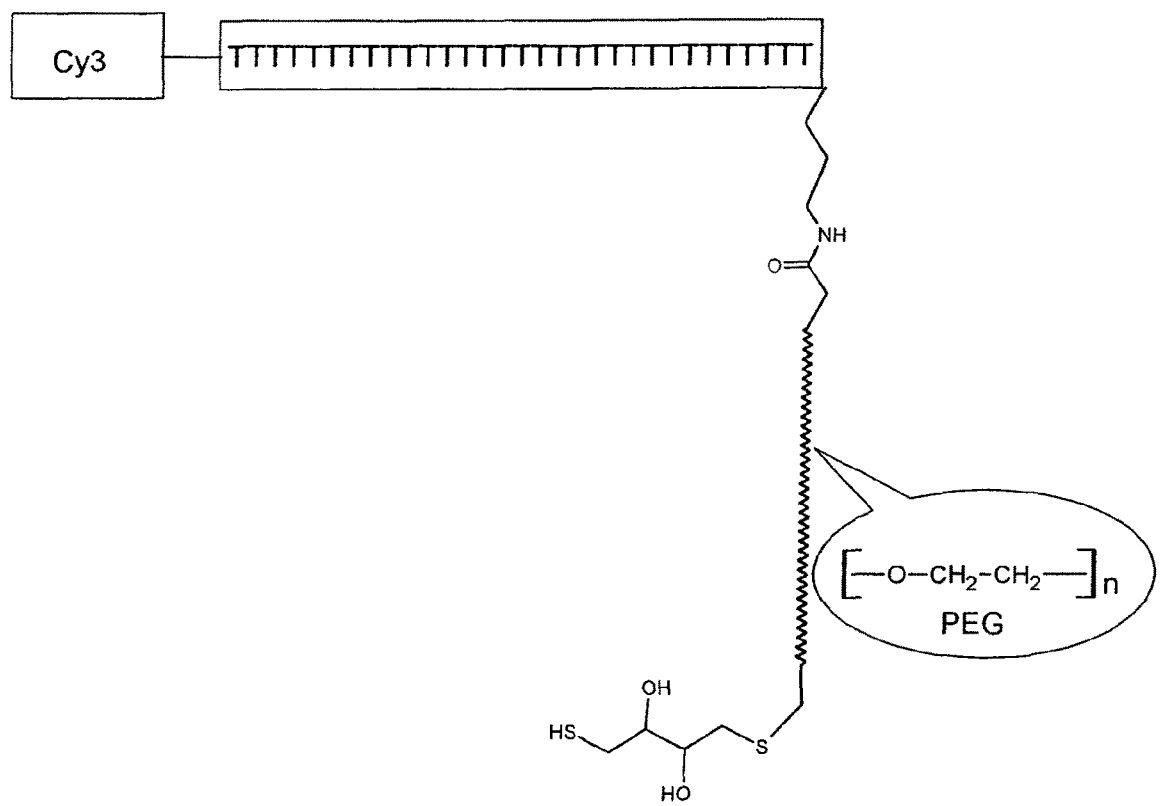
FIG. 49 depicts SH—R-PEG-Oligo-dT$_{31}$-Cy3.

Synthesis of SH—R-PEG-Oligo-dT$_{31}$-Cy3 (FIG. 49)

NHS-PEG-maleimide was added to 200 µl of 100 µmol/l solution of 3'-amino-oligo-dT$_{31}$-Cy3 in 50 mmol/l borate buffer, pH 9, until the concentration of 20% (w/v) was reached. The mixture was stirred vigorously at 40° C. for 2 h. The maleimide-PEG-oligo-dT$_{31}$-Cy3 was separated from the excess PEG derivative using DEAE-cellulose column chromatography: The reaction mixture was applied to the column in 10 mmol/l borate, pH 9, and was washed with 20 column volumes of 50 mmol/l borate, pH 9.

The maleimide-PEG-Oligo-dT$_{31}$-Cy3 was eluted from the column 1 M NaCl in 50 mmol/l borate, pH 9. The eluate was first concentrated by ultrafiltration (MWCO 3,000) and the product was rebuffered in 20 mmol/l borate buffer, pH 9.0. The maleimide-PEG-oligo-dT$_{31}$-Cy3 was separated from oligo-dT$_{31}$-Cy3 on preparative polyacrylic gel (15%) by the electrophoresis and was isolated from the gel and dissolved in 50 mmol/l borate buffer, pH 9.0. Yield: 55%.

DTT was to the solution of maleimide-PEG-Oligo-dT$_{31}$-Cy3 up to a concentration 0.5 mol/l and the mixture was stirred for 16 h at RT. SH—R-PEG-Oligo-dT$_{31}$-Cy3 is obtained from the reaction of DTT with maleimide. This substance was separated from the excess DTT on the DEAE column: The reaction mixture was applied to the column in 50 mmol/l Na-acetate, pH 6.0, and was washed with 20 column volumes of 50 mmol/l Na-acetate, pH 6.0. A solution of NaCl (1 mol/l in 50 mmol/l Na-acetate, pH 6.0) was used to elute SH—R-PEG-oligo-dT$_{31}$-Cy3 from the column. The eluate was first concentrated by ultrafiltration (MWCO 3,000) and the product, SH—R-PEG-oligo-dT$_{31}$-Cy3, was rebuffered in 50 mmol/l borate buffer, pH 9.0. The concentration of SH—R-PEG-oligo-dT$_{31}$-Cy3 amounted to 100 µmol/l.

Fifty equivalents of dUTP-AA-PDTP (synthesized as described in the example 1) were added to this solution. After 3 h at RT, separation was conducted on DEAE-cellulose: The mixture was applied to the column in 50 mmol/l Na-acetate buffer, pH 6.0, and was washed with 20 column volumes of 50 mmol/l Na-acetate, pH 6.0. The dUTP-AA-PDTP was eluted using 0.3 mol/l NaCl in 50 mmol/l Na-acetate, pH 6.0; the dUTP-AA-SS—R-PEG-oligo-dT31-Cy3 was eluted using 0.8 mol/l NaCl in 50 mmol/l Na-acetate, pH 6.0. The eluate was first concentrated by ultrafiltration (MWCO 3,000) and the product was rebuffered in 50 mmol/l Na-acetate buffer, pH 6.0.

The substance comprises a nucleoside triphosphate functionality and macromolecular marker functionalities (oligo-dT31). The Oligo-dT31 consists of nucleoside monophosphates which, however, do not take part in the enzymatic reaction and have only a signal-transmitting function. Complementary nucleic acid chains having a signal-giving function can be hybridized to such an oligonucleotide (FIG. 37B). General rules to the hybridization of nucleic acids are known to the person skilled in the art, Anderson "Nucleic Acid Hybridization", 1999.

The nucleotide is, by definition, a nuc-macromolecule: the linker length is significantly longer than 30 atoms, the marker component is macromolecular. Polymerases (e.g., Klenow-exo minus polymerase and terminal transferase) accept this compound as a substrate.

Other oligonucleotides can be also coupled to the dUTP derivative in a similar manner. In one embodiment of the invention, other homopolymer oligonucleotides, such as poly-dC, poly-dG or poly-dU or poly-dA, are suitable. In another embodiment, it is also possible to use oligonucleotides with specific sequences. By using specific sequences of oligonucleotides, it is possible to hybridize nucleic acid chains specifically to these sequences. Oligonucleotides comprising hairpin structures (stemloops) can be used for the synthesis of nuc-macromolecules.

In this example, the oligonucleotide comprises one amino group and the Cy3-fluorescence dye, the amino group acting as a coupling position for maleimide-PEG-NHS and being coupled at the 3'-end by a linker. Other coupling groups, like SH—, carboxy-, and aldehyde groups can also be used.

The position of the coupling group can be at one of the ends of the oligonucleotide, or can also be located in the middle of the sequence. Such oligonucleotides can be synthesized by MWG Biotech, Germany.

Oligonucleotides can comprise fluorescence dyes or other reporter groups, like biotin or digoxigenin, as modifications. Several modifications per oligonucleotide are also possible. For instance, FRET pairs or a fluorescence-dye/quencher-molecule pair can be introduced into an oligonucleotide.

This example shows a general possibility for making further modifications to nucleotides. Other base-modified nucleotide analogs, e.g., 5-propargylamino-dCTP, 5-aminopropargyl-dUTP, 7-deaza-aminopropargyl-dGTP and 7-deaza-aminopropargyl-dATP can be also modified in a manner similar to that described above. Ribonucleotides, 2'-deoxyribonucleotides as well as 2',3'-dideoxyribonucletide can be used, FIGS. 11 to 14. Other bases-modified nucleotides can also be used in similar way.

Several dUTP-M-SS-R-PEG-Oligo-dT31-Cy3, e.g., 10-20, can be coupled to one nuc-macromolecule by adding poly-dA or poly-A. A nuc-macromolecule with linearly arranged nuc-linker-components is thereby obtained (FIG. 37 C).

Further modifications, e.g., fluorescence labeling, can be also introduced by adding other modified oligonucleotides that can bind to poly-dA or poly-A.

Example 40

Synthesis of (dATP-PA-PEG)$_{n}$-PAS-(Cy3)$_{m}$

The synthesis of dATP-PA-PEG-NH$_2$ was described in the example 19.

EDA-Cy3 was synthesized as follows: Cy3-NHS (0.1 mg) was added to 1 ml of solution of EDA (400 mmol/l, in water, pH 8.5 adjusted by HCl). The reaction was stirred for 30 min at RT. The product was separated on RP-18 (water methanol gradient) and the volume was condensed to 0.2 ml.

PAS 100 kDa (35% solution, in water) was repeatedly co-evaporated with DMF in a rotary evaporator until a water-free DMF solution was obtained. CDI (3 mg) was added to the resulting solution of PAS (200 µl, 0.1 mmol/l, 2 mg in 200 µl DMF). Reaction was allowed to proceed for 30 min at RT. Next, a solution of EDA-Cy3 (0.2 ml, 0.7 mmol/l) and dATP-PA-PEG-NH$_2$ (0.2 ml, 0.5 mmol/l) were simultaneously added to this solution. The reaction was carried out at RT for 1 h. The product (dATP-PA-PEG)$_n$-PAS-(Cy3)$_m$ was then separated from EDA-Cy3 and dATP-PA-PEG-NH$_2$ by ultrafiltration with 100 kDa MWCO. The average number of the Cy3 derivatives amounts to five per PAS molecule and the average number of nuc-units (dATP) per PAS molecule amounts to two. A nuc-macromolecule comprising several marker units and several nuc-units was synthesized in this manner.

(dATP-PA-PEG)$_n$-PAS-(Cy3)$_m$ acts as a substrate for the DNA polymerases and can be used in the labeling reactions.

Example 41

Nuc-macromolecules as Monomer Constituents of an Oligonucleotide

For examples of the enzymatic incorporation of nuc-macromolecules into the nucleic acid, see examples 34 and 35.

Couplings of a long linker and a marker to the nucleotide monomers comprising a reactive group were described above. A nucleotide monomer that is part of a polymer, e.g., of a nucleic acid chain, and comprises a reactive group can be modified in a similar way. A long, linear, unbranched linker, like PEG, is preferably used. Nucleotide monomers with a reactive group, such as an amino group or mercapto group, can be coupled into a nucleic acid chain by means of conventional oligonucleotide synthesis. Many modifications can be introduced into an oligonucleotide by custom synthesis, by MWG Biotech for instance.

Synthesis of a Modified Oligonucleotide:

MWG Biotech synthesized an oligonucleotide with 31 dT monomers and an amino group coupled at 5' ends (5'-amino-dT31). It is possible to couple a Fmoc-PEG-NHS linker, for example, to such an oligonucleotide:

Fmoc-PEG-NHS (1 mg of Fmoc-protected NH$_2$-PEG-NHS) was added to 100 µl of a solution of 5'-amino-dT31 (0.5 mmol/l, pH 8.0, in water) and stirred at 30° C. for 8 h. The pH-value was then raised to 11 and the reaction mixture was stirred for another 2 hours at RT. Next, the modified oligonucleotide was separated from unmodified oligonucleotide by electrophoresis in a 15% of polyacrylic gel and isolated. The product of the reaction, NH$_2$-PEG-dT31, was dissolved in 50 µl of 50 mmol hydrogen carbonate buffer, pH 8.0, to a concentration of 0.3 mmol/l. It is possible to couple a macromolecular marker to the terminal amino group. It is possible to synthesize an oligonucleotide modified with a macromolecular marker using a reaction similar to that described in Example 40. EDA-Cy3 was synthesized as in Example 40. PAS 100 kDa (35% solution in water) was repeatedly co-evaporated with DMF in a rotary evaporator until a water-free solution was obtained. Next, CDI (1 mg, as concentrated solution in DMF) was added to the resulting solution of PAS (50 µl, 0.1 mmol/l, in DMF). Reaction was allowed to proceed for 30 min at RT. Next, a solution of EDA-Cy3 (50 µl, 1.5 mmol/l) and NH$_2$-PEG-dT31 (50 µl, 0.3 mmol/l) were simultaneously added to this solution. The reaction was carried out at RT for 1 h. The product (dT31-PEG)n-PAS-(Cy3)m was then separated from EDA-Cy3 and NH$_2$-PEG-dT31 by ultrafiltration with 100 kDa MWCO.

The average number of the Cy3 derivatives per PAS molecule amounts to seven, and the average number of the coupled oligonucleotides per PAS molecule amounts to 1. An oligonucleotide modified by a polymer and comprising a nuc-macromolecule was synthesized in this manner.

Example 42

Synthesis of a Nuc-macromolecule with a Linker at the Phosphate

A linker can be also coupled to phosphate groups of a nucleotide. A coupling of a reactive group, of an amino group to the terminal phosphate group for instance is already known (Jameson et al. Method in Enzymology, 1997, V. 278, p. 363-, A. Draganescu et al. J. Biol. Chem. 2000 V. 275, 4555-). It is possible to couple the linker component to the nucleotide in a manner analogous to the syntheses in other examples.

Example 43

Producing a Modified Klenow Fragment Exo Minus of the DNA Polymerase I of *E. Coli* (Hereinafter Called Klenow Fragment Exo Minus)

In one embodiment of the modification, a buffer solution (100 μl, 200 mmol/l Tris HCl buffer, pH 10.0, 60% of glycerol) is added to a buffer solution with Klenow fragment exo minus of the DNA polymerase (70 μl, 750 units-vial of Amersham Bioscience, dissolved in the manufacturer's buffer: 50 mmol/l potassium phosphate buffer, pH 7, 1.0 mmol/l DTT, 50% glycerol), the pH value of the solution with the polymerase thus amounting to 9.0. Next, a solution of iodacetamide (30 μl, 1 mol/l in water) are added. The reaction is carried out for 30 min at RT. A selective modification of the polymerase thereby occurs at the SH group of the cysteine.

In another embodiment of the modification, a solution of TCEP-NaOH (10 μl, 50 mmol/l, pH 8) is first added to a buffer solution with Klenow fragment exo minus of the DNA polymerase (70 μl, 750 units-vial of Amersham Bioscience, dissolved in the manufacturer's buffer, see above). After 10 min at RT, a buffer solution (100 μl, 200 mmol/l Tris HCl buffer, pH 10.0, 60% of glycerin) is added to the solution with polymerase. Next, a solution of iodacetamide (30 μl, 1 mol/l in water) is added. The reaction is carried out for 30 min at RT. A selective modification of the polymerase thereby occurs on the SH group.

It is possible to purify the modified polymerase, for instance, via ultrafiltration or by an ionic exchanger or dialysis.

It is possible to store the modified polymerase, for instance, in a glycerin-containing buffer. Tris-HCl, borate, and phosphate buffers are suitable as buffers, for example. The pH value of these buffers ranges, for instance, between 5 and 10. The concentration of the glycerin can range, for instance, between 10 and 70%.

It is also possible to add other reagents, for instance PEG or salts like NaCl, $NH_4Cl$, to the polymerase solution. It is preferred that no reductive agents, e.g., DTT, be added to the polymerase solution.

In one embodiment, the storage buffer additionally contains a reagent which can react with SH groups selectively, for instance, iodacetamide in a concentration between 1 mmol/l and 500 mmol/l.

A polymerase modified in this manner can be used in reactions with nuc-macromolecules instead of Klenow fragment exo minus of the DNA polymerase.

The invention claimed is:

1. Macromolecular compounds having the structure:

(nuc-linker)$_n$-marker wherein:

nuc is a nucleotide or nucleoside (nuc-component);

linker is a linker component wherein the linker links the nuc component to a marker, and the linker comprises the following parts:

a) coupling unit L, which provides linkage between the nuc and one end of a water soluble-polymer, said polymer comprising an average length between 100 and 20,000 atoms, and, b) coupling unit T which provides linkage between the marker and the water soluble polymer, wherein, the marker is a marker component comprising at least one macromolecule of at least 2000 Da, a plurality of low molecular weight marker units or a combination of at least one low molecular weight marker unit with a molecular weight below 2000 Da and at least one macromolecular marker unit with a molecular weight of at least 2000 Da; and (n) is a positive integer between 1 and 100, and wherein, the linker is covalently or non-covalently bound to the nuc and the marker.

2. The macromolecular compounds according to claim 1, wherein the nuc-component comprises the following structure:

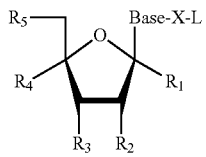

wherein:

base is selected independently from the group of adenine, or 7-deazaadenine, or guanine, or 7-deazaguanine, or thymine, or cytosine, or uracil, or their modifications, X is the coupling position of the linker to the base and L is the coupling unit of the linker (L)

$R_1$—is H, $R_2$—is selected independently from the group of H, OH, halogen, $NH_2$, SH or protected OH group, $R_3$—is selected independently from the group of H, OH, halogen, $PO_3$, SH, $N_3$, $NH_2$, O—$CH_3$, O—$CH_2$—O—$CH_3$, O—$CH_2$—CH=$CH_2$, O—$R_{3-1}$, $P(O)_m$—$R_{3-1}$ ((m) is 1 or 2), NH—$R_{3-1}$, S—$R_{3-1}$, Si—$R_{3-1}$ wherein $R_{3-1}$ is a chemically, photochemically or enzymatically cleavable group, $R_4$—is H or OH, and $R_5$—is selected independently from the group of OH, or a protected OH group, or a monophosphate group, or a diphosphate group, or a triphosphate group, or is an alpha thiotriphosphate group.

3. The macromolecular compounds according to claim 1, wherein the nuc-component comprises the following structure:

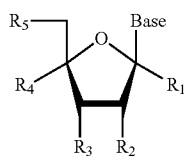

wherein:

base is selected independently from the group of adenine, or 7-deazaadenine, or guanine, or 7-deazaguanine, or thymine, or cytosine, or uracil, or their modifications capable of enzymatic reactions, $R_1$—is H, $R_2$—is selected independently from the group of H, OH, halogen, $NH_2$, SH or protected OH group, $R_3$—is selected independently from the group of O—$R_{3-2}$-L, $P(O)_m$—$R_{3-2}$-L and (m) is 1 or 2, NH—$R_{3-2}$-L, S—$R_{3-2}$-L, Si—$R_{3-2}$-L, wherein $R_{3-2}$ is the coupling position of the linker to the nucleotide and L is the coupling unit of the linker (L), $R_4$—is H or OH, and $R_5$—is selected independently from the group of OH, or a protected OH group, or a monophosphate group, or a diphosphate group, or a triphosphate group, or is an alpha-thiotriphosphate group.

4. The macromolecular compounds according to claim 1, wherein the nuc-component comprises the following structure:

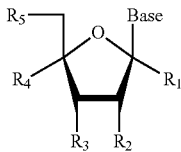

wherein:
base is selected independently from the group of adenine, or 7-deazaadenine, or guanine, or 7-deazaguanine, or thymine, or cytosine, or uracil, or their modifications capable of enzymatic reactions,
$R_1$—is H,
$R_2$—is selected independently from the group of H, OH, halogen, $NH_2$, SH or protected OH group,
$R_3$—is selected independently from the group of H, OH, halogen, $PO_3$, SH, $NH_2$, O—$R_{3-1}$, $P(O)_m$—$R_{3-1}$((m) is 1 or 2), NH—$R_{3-1}$, S—$R_{3-1}$, Si—$R_{3-1}$ wherein $R_{3-1}$ is a chemically, photochemically or enzymatically cleavable group,
$R_4$—is H or OH, and
$R_5$—is selected independently from the group of O—$R_{5-1}$-L, or P—$(O)_3$—$R_{5-1}$-L (modified monophosphate group), or P—$(O)_3$—P—$(O)_3$—$R_{5-1}$-L (modified diphosphate group) or P—$(O)_3$—P—$(O)_3$—P—$(O)_3$—$R_{5-1}$-L (modified triphosphate group), wherein $R_{5-1}$ is the coupling position of the linker to the nucleotide and L is the coupling unit of the linker (L).

5. The macromolecular compounds according to claim 1, wherein the coupling unit (L) of the linker comprises a structural element selected from the group consisting of:
$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$,
$R_6$—O—CO—$R_7$, $R_6$—CO—S—$R_7$, $R_6$—S—CO—$R_7$, $R_6$—P(O)$_2$—$R_7$, $R_6$—Si—$R_7$, $R_6$—$(CH_2)_n$—$R_7$,
$R_6$—$(CH_2)_n$—$R_7$, $R_6$-A-$(CH_2)_n$—$R_7$, $R_6$—$(CH_2)_n$—B—$R_7$,
$R_6$—(CH=CH—)$_n$—$R_7$, $R_6$-(A-CH=CH—)$_n$—$R_7$, $R_6$—(CH=CH—B—)$_n$—$R_7$,
$R_6$-A-CH=CH—$(CH_2$—)$_n$—$R_7$, $R_6$—(—CH=CH—$CH_2)_n$—B—$R_7$,
$R_6$—(C≡C—)$_n$—$R_7$, $R_6$-(A-C≡B—)$_n$—$R_7$, $R_6$—(C≡C—B—)$_n$—$R_7$, and
$R_6$-A-C≡C—$(CH_2$—)$_n$—$R_7$, $R_6$—(—C≡C—$CH_2)_n$—B—$R_7$, $R_6$—(—C≡C—$CH_2$—$CH_2$—)$_n$—B—$R_7$,
wherein $R_6$ is the nuc-component, $R_7$ is the rest of the linker, and A and B each independently comprise: —NH—, —O—, —S—, —SS—, —CO—NH—, —NH—CO—, —CO—O—, —O—CO—, —CO—S—, —S—CO—, —P(O)$_2$—, —Si—, or —$(CH_2)_n$—, wherein (n) ranges from 1 to 5, a photolabile group.

6. The macromolecular compounds according to claim 1, wherein the water soluble-polymer is independently selected from the group consisting of:
polyethylene glycol (PEG), polysaccharides, dextran, polyamides, polypeptides, polyphosphates, polyacetates, polyalkyleneglycoles, copolymers from ethyleneglycol and propyleneglycol, polyolefinic alcohols, polyvinylpyrrolidones, poly(hydroxyalkylmethacrylamides), polyhydroxyalkylmethacrylates, poly(x-hydroxy) acids, polyacrylic acid, polyacrylamide, and polyvinylalcohol.

7. The macromolecular compounds according to claim 1, wherein the average length of at least one linker component ranges between 50 to 100, 100 to 200, 200 to 500, 500 to 1000, 1000 to 2000, 2000 to 10000, 10000 to 50000 atoms (chain atoms).

8. The macromolecular compounds according to claim 1, wherein the marker component has one of the following functions: signal-giving function, signal-transmitting function, catalytic function or affine function.

9. The macromolecular compounds according to claim 1, wherein the marker component consists of at least one macromolecular structural marker unit.

10. The macromolecular compounds according to claim 1, wherein the marker component consists of a plurality of structural marker units.

11. The macromolecular compounds according to claim 10, wherein the marker component consists of at least five marker units independently selected from the group of elements consisting of biotin, hapten, radioactive isotope, rare-earth atom, dye, and fluorescent dye.

12. The macromolecular compounds according to claim 9, wherein the structural marker unit independently comprises one of the following elements: nanocrystals or their modifications, proteins or their modifications, nucleic acids or their modifications, nanoparticles or microparticles or their modifications.

13. The macromolecular compounds according to claim 12, wherein the structural marker unit comprises one of the following proteins:
enzymes or conjugates or modifications thereof,
antibodies or conjugates or modifications thereof,
streptavidin or its conjugates or modifications thereof, and
avidin or its conjugates or modifications thereof.

14. The macromolecular compounds according to claim 12, wherein a structural marker unit comprises a nucleic acid chain selected from:
DNA, RNA, and PNA, wherein the length of the nucleic acid chain ranges from 10 to 10,000 nucleotides.

15. The macromolecular compounds according to claim 10, wherein the plurality of structural marker units are bound to at least one core component of the marker and the core component independently comprises one of the following elements:
a water-soluble polyamide,
polyacrylic acid or a derivative thereof,
polyacrylamide or a derivative thereof,
polyvinylalcohol or a derivative thereof, nucleic acid or a derivative thereof,
streptavidin or avidin or a derivative thereof, and
dendrimere, wherein the element is linear or branched, and optionally is crosslinked to other core components.

16. The macromolecular compounds according to claim 15, wherein the linkage between several structural marker units and the core component is covalent or non-covalent.

17. The macromolecular compounds according to claim 15, wherein the linkage between the core component and the linker is covalent or non-covalent.

18. The macromolecular compounds according to claim 1, wherein only one nuc-component with one linker component is linked to the marker component, wherein the linker length ranges between 50 to 100, 100 to 200, 200 to 500, 500 to 1000, 1000 to 2000, 2000 to 5000 atoms.

19. The macromolecular compounds according to claim 1, wherein the linker length ranges between 50 to 100, 100 to 200, 200 to 500, 500 to 1000, 1000 to 2000, or 2000 to 5000 atoms and the linker component comprises at least one compound that is cleavable under mild conditions.

20. The macromolecular compounds according to claim 1, wherein the linker length ranges between 50 to 100, 100 to 200, 200 to 500, 500 to 1000, 1000 to 2000, or 2000 to 5000 atoms and one or several parts of the macromolecular compound are modified in such a way, that only one nuc-component can be incorporated into a growing nucleic acid chain.

21. An oligonucleotide or polynucleotide comprising at least one macromolecular compound according to claim 1 per one oligonucleotide or polynucleotide, wherein said oligonucleotide or polynucleotide is obtained by an enzymatic incorporation of the at least one macromolecular compound into the oligonucleotide or polynucleotide.

22. The oligonucleotides or polynucleotides according to claim 21, wherein oligo- or polynucleotides are RNA or DNA or PNA and their length ranges between 5 and 50,000 nucleotides.

23. A method of enzymatic modification of nucleic acid chains in an enzymatic coupling reaction comprising the steps of:
   a) providing at least one population of nucleic acid chains,
   b) incubating the at least one population of nucleic acid chains with at least one type of distinctly labeled macromolecular compound according to claim 1 wherein each type of distinctly labeled macromolecular compound is labeled on the basis of its nuc-component or marker, in a reaction solution under conditions which allow for incorporation of the macromolecular compound into the at least one population of nucleic acid chains and;
   c) detecting signals from the at least one population of nucleic acid chains which have incorporated the at least one type of macromolecular compound to thereby identify said at least one population of nucleic acid chains.

24. The method according to claim 23, wherein:
the modification is accomplished by an enzymatic coupling and wherein the reaction solution comprises at least one type of enzyme for coupling the at least one type of macromolecular compound to the at least one population of nucleic acid chains.

25. The method according to claim 24, wherein the reaction mixture further comprises at least one type of nucleoside triphosphate that is different from the nucleoside component of the macromolecular compound.

26. The method according to claim 24, wherein the enzyme is selected from the group consisting of: DNA-polymerases, RNA-polymerases, and terminal transferases.

27. The method according to claim 25, wherein the type of nucleoside triphosphate is independently selected from the group consisting of ribonucleoside tri-phosphates (ATP, GTP, UTP, CTP), 2'-deoxyribonucleoside triphosphates (dATP, dUTP, dTTP, dCTP, dGTP),2',3'-dideoxynucleoside triphosphates (ddATP, ddGTP, ddUTP, ddCTP, ddTTP), and derivatives thereof.

28. The method according to claim 27, wherein the type of nucleoside tri-phosphate is a nucleotide modified with a label, selected from the group consisting of fluorescent dye, biotin, hapten and a radioactive element and wherein the structure of the nucleoside tri-phosphate is different from the structure of the labeled macromolecular compound.

29. The method according to claim 24, wherein at least two different populations of nucleic acid chains are provided in step (a).

30. The method according to claim 29, wherein at least one of the populations of the nucleic acid chains has a primer function and at least one population of the nucleic acid chains has a template function.

31. The method according to claim 24, wherein macromolecular compounds which allow for the coupling of only a single nuc-component into the growing nucleic acid chains are used and multiple incorporations of nuc-components are prevented by modifications of the nuc-component and/or the linker component and/or the marker component of the macromolecular compound.

32. The method according to claim 31, wherein the prevention of multiple coupling is reversible.

33. The method according to claim 31, wherein the prevention of multiple coupling is irreversible.

34. The method according to claim 24 wherein multiple nuc-components are incorporated into the growing nucleic acid chains.

35. The method according to claim 24, wherein at least one population of the nucleic acid chains participating in the reaction is attached to a solid phase which has an addressable position for each population of the nucleic acid chains.

36. The method according to claim 35, wherein the said nucleic acid chains comprise a uniform population of nucleic acid chains.

37. The method according to claim 35, wherein the said population of nucleic acid chains compose two or more different populations of nucleic acid chains and the solid phase has an addressable position for each of said populations of nucleic acid chains.

38. The method according to claim 35, wherein the coupling of macromolecular compounds is conducted on the uniform population of nucleic acid molecules attached to the solid phase and the marker component of the macromolecular compound remains on the extended nucleic acid strand after the coupling and is not cleaved off.

39. The method according to claim 35, wherein coupling of the macromolecular compounds in step (b) is conducted on the uniform population of nucleic acid chains attached to the solid phase and wherein the method further comprises a step of cleaving off the marker component or its individual parts from the macromolecular compound that is incorporated into the growing nucleic acid chains with or without the linker component of the macromolecular compound, wherein the step of the cleaving-off occurs during or after the coupling of the macromolecular compound into the nucleic acid chains.

40. The method according to claim 35, wherein the coupling of macromolecular compounds in step (b) in a reaction mixture is conducted simultaneously on two or more different populations of nucleic acid chains attached to the solid phase, wherein each of the different populations has distinct addressable positions on the solid phase, and the marker component of the macromolecular compound remains on the extended nucleic acid chain after the coupling is completed and is not cleaved off.

41. The method according to claim 35, wherein the coupling of macromolecular compounds is conducted simultaneously on two or more different uniform populations of nucleic acid chains attached to the solid phase, wherein each of the populations of the nucleic acid chains has a distinct addressable position on the solid phase, and the marker component or its individual parts are cleaved off, with or without the linker component of the macromolecular compound, from the nuc-component, and wherein the step of the cleaving-off occurs during or after the coupling of the macromolecular compound to the nucleic acid chain.

42. The method according to claim 35, wherein the addressable positions having nucleic acid molecules on the solid phase are distributed as spots on a plane surface, and nucleic acid molecules are uniform on each spot.

43. The method according to the claim 35, wherein the sold phase is a bead or particle having an addressable position for a single uniform population of nucleic acid chains.

44. The method according to claim 35, wherein the addressable positions are distributed in a multivessel array and each vessel of the multivessel array comprises an addressable position for a single uniform population of nucleic acid chains.

45. A kit comprising at least one kind of macromolecular compound (macromolecular compounds) according to claim 1.

46. The method of claim 21 wherein the reaction solution comprises a polymerase, ligase, endonuclease, exonuclease, or a combination thereof.

47. The macromolecular compounds according to claim 1, wherein the coupling unit (T) of the linker comprises at least one element selected from the group consisting of:
C, O, S, N, CO, and biotin.

\* \* \* \* \*

UNITED STATES PATENT AND TRADEMARK OFFICE
CERTIFICATE OF CORRECTION

PATENT NO. : 8,637,650 B2  
APPLICATION NO. : 10/578313  
DATED : January 28, 2014  
INVENTOR(S) : Cherkasov et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2113 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Primer, example 34A, modified on 5 prime-end by
      Cy3

<400> SEQUENCE: 1
taatacgact cactataggg                                                    20

<210> SEQ ID NO 2
<211> LENGTH: 33
<212> TYPE: DNA
<213> ORGANISM: Artificial
<220> FEATURE:
<223> OTHER INFORMATION: Template, example 34A

<400> SEQUENCE: 2
agttttagtt ttaccctata gtgagtcgta tta                                     33

<210> SEQ ID NO 3
<211> LENGTH: 35
<212> TYPE: DNA
<213> ORGANISM: Artificial
<220> FEATURE:
<223> OTHER INFORMATION: Primer, example 34B, modified at 5 prime -end
      by Cy3

<400> SEQUENCE: 3
tttttttttt tttttttttt tttttttttt ttttt                                   35

<210> SEQ ID NO 4
<211> LENGTH: 40
<212> TYPE: DNA
<213> ORGANISM: Artificial
```

-continued

```
<220> FEATURE:
<223> OTHER INFORMATION: Oligonucleotide, modified at 5 prime -end by
      Cy3

<400> SEQUENCE: 4
tttttttttt tttttttttt tttttttttt tttttttttt                          40

<210> SEQ ID NO 5
<211> LENGTH: 50
<212> TYPE: DNA
<213> ORGANISM: Artificial
<220> FEATURE:
<223> OTHER INFORMATION: Oligonucleotide, example 34B, modified at 5
      prime -end by Cy3

<400> SEQUENCE: 5
tttttttttt tttttttttt tttttttttt tttttttttt tttttttttt               50

<210> SEQ ID NO 6
<211> LENGTH: 270
<212> TYPE: DNA
<213> ORGANISM: Artificial
<220> FEATURE:
<223> OTHER INFORMATION: Polynucleotide with an average length of 270
      nucleotides, example 34B

<400> SEQUENCE: 6
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa                                   270

<210> SEQ ID NO 7
<211> LENGTH: 50
<212> TYPE: DNA
<213> ORGANISM: Artificial
<220> FEATURE:
<223> OTHER INFORMATION: Oligonucleotide, example 34C, modiified at 3
      prime- end by biotin, attached via a TEG-linker

<400> SEQUENCE: 7
aaaaaaaaaa aaaaaaaaaa aaaaaaaaaa aaaaaaaaaa aaaaaaaaaa               50

<210> SEQ ID NO 8
<211> LENGTH: 35
<212> TYPE: DNA
<213> ORGANISM: Artificial
<220> FEATURE:
<223> OTHER INFORMATION: Primer, example 35

<400> SEQUENCE: 8
tttttttttt tttttttttt tttttttttt ttttt                               35

<210> SEQ ID NO 9
<211> LENGTH: 31
<212> TYPE: DNA
<213> ORGANISM: Artificial
<220> FEATURE:
<223> OTHER INFORMATION: Oligonucleotide, example 39, modified at 3
      prime- end by an amino-group, at 5 prime- end by Cy3

<400> SEQUENCE: 9
tttttttttt tttttttttt tttttttttt t                                   31
```

```
<210> SEQ ID NO 10
<211> LENGTH: 31
<212> TYPE: DNA
<213> ORGANISM: Artificial
<220> FEATURE:
<223> OTHER INFORMATION: Oligonucleotide, example 30, modified at 3
      prime- end by biotin, coupled via TEG-spacer

<400> SEQUENCE: 10
tttttttttt tttttttttt tttttttttt t                              31

<210> SEQ ID NO 11
<211> LENGTH: 30
<212> TYPE: DNA
<213> ORGANISM: Artificial
<220> FEATURE:
<223> OTHER INFORMATION: Oligonucleotide, examples 27 and 32, modified
      at 3 prime- end by SH-group

<400> SEQUENCE: 11
tttttttttt tttttttttt tttttttttt                                30
```